United States Patent
Nagy et al.

(10) Patent No.: US 7,629,318 B2
(45) Date of Patent: Dec. 8, 2009

(54) IMMUNOSUPPRESSANT COMPOUNDS, METHODS AND USES RELATED THERETO

(75) Inventors: Zoltan Nagy, Wolfratshausen (DE); Tilmann Brandstetter, München (DE)

(73) Assignee: GPC Biotech AG, Munich (DE)

( * ) Notice: Subject to any disclaimer, the term of this patent is extended or adjusted under 35 U.S.C. 154(b) by 365 days.

(21) Appl. No.: 10/508,504

(22) PCT Filed: Mar. 24, 2003

(86) PCT No.: PCT/US03/09219

§ 371 (c)(1),
(2), (4) Date: Jun. 6, 2005

(87) PCT Pub. No.: WO03/082197

PCT Pub. Date: Oct. 9, 2003

(65) Prior Publication Data

US 2006/0004077 A1    Jan. 5, 2006

Related U.S. Application Data

(60) Provisional application No. 60/367,123, filed on Mar. 22, 2002.

(51) Int. Cl.
| | |
|---|---|
| A61K 38/08 | (2006.01) |
| A61K 38/07 | (2006.01) |
| A61K 38/06 | (2006.01) |
| A61K 38/05 | (2006.01) |
| C07K 7/04 | (2006.01) |
| C07K 5/10 | (2006.01) |
| C07K 5/08 | (2006.01) |
| C07K 5/02 | (2006.01) |
| C07K 1/00 | (2006.01) |

(52) U.S. Cl. .............................. 514/16; 514/17; 514/18; 514/19; 530/329; 530/330; 530/331; 530/332; 530/333

(58) Field of Classification Search ........................ None
See application file for complete search history.

(56) References Cited

FOREIGN PATENT DOCUMENTS

| WO | WO-96/19483 A1 | 6/1996 |
|---|---|---|
| WO | WO-96/37497 A1 | 11/1996 |
| WO | WO-97/48687 A1 | 12/1997 |
| WO | WO-97/48706 A1 | 12/1997 |
| WO | WO-98/09987 A1 | 3/1998 |
| WO | WO-98/28326 A1 | 7/1998 |
| WO | WO-99/61476 A1 | 12/1999 |
| WO | WO-00/78796 A2 | 12/2000 |
| WO | WO-01/27141 A1 | 4/2001 |

OTHER PUBLICATIONS

S. Feng and S.L. Schreiber. J. Am. Chem. Soc. (1997) 119, pp. 10873-10874.*
Q. Xu et al. Biochemistry. (1999) 38, pp. 3491-3497.*
Christensen, H. N., et al., "Synthesis of Metabolism-Resistant Substrates for the Transport System for Cationic Amino Acids;Their Stimulation of the Release of Insulin and Glucagon, and of the Urinary Loss of Amino Acids Related to Cystinuria," Biochimica et Biophysica Acta,, 298:932-950 (1973).
Cunningham, B.R., et al., "SAR For MHC Class II Binding Tetrapeptides: Correlation With Potential Binding Site," Bioorganic & Medicinal Chemistry Letters, 7(1):19-24 (1997).
Falcioni, F., et al., "Peptidomimetic compounds that inhibit antigen presentation by autoimmune disease-associated class II major histocompatibility molecules," Nature Biotechnology, 17:562-567 (1999).
Hanson, G.J., et al., "Design of MHC Class II (DR4) Ligands Using Conformationally Restricted Imino Acids at p3 and p5," Bioorganic & Medicinal Chemistry Letters, 6(16):1931-1936 (1996).
Jones, A.B., et al., "Tetrapeptide Derived Inhibitors of Complexation of a Class II MHC: Fully Unnatural Ligands," Bioorganic & Medicinal Chemistry Letters, 9:2115-2118 (1999).
Jones, A.B., et al., "Tetrapeptide Derived Inhibitors of Complexation of a Class II MHC: The Peptide Backbone is not Inviolate," Bioorganic & Medicinal Chemistry Letters, 9:2109-2114 (1999).
Kent, D. R., et al., "Synthesis of 3-(3-pyrrolidinyl)alanine and its derivatives as arginine peptidomimetics for incorporation into serine protease inhibitors," Pept. Proc. Am. Pept,. Symp., 15th (1999), Meeting Date 1997, 688-689.
Plummer, J. S., et al., "Potent and Selective Bicyclic Lactam Inhibitors of Thrombin: Part 2: P1 Modifications," Bioorganic & Medicinal Chemistry Letters, 8:3409-3414 (1998).
Schmidt, M.A., et al., "Increased serum stability of neurotensin analogs containing arginine mimics," (2000) Pept. New Milennium, Proc Am Pept. Symp 634-635 (use of Gpg to stabiles neurotensin peptides).
St. Laurent, D. R., et. al., "Active Site-directed Thrombin Inhibitors—II. Studies Related to Arginine/Guanidine Bioisosteres," Bioorganic & Medicinal Chemistry, 3(8):1145-1156 (1995).
Tamura, S.Y., et al., "Guanylpiperidine Peptidomimetics: Potent and Selective bis-Cation Inhibitors of Factor Xa," Bioorganic & Medicinal Chemistry Letters, 10:745-749 (2000).

* cited by examiner

*Primary Examiner*—Andrew D Kosar
(74) *Attorney, Agent, or Firm*—Leon R. Yankwich; David G. O'Brien; Yankwich & Associates, P.C.

(57) ABSTRACT

The present invention relates to compositions and methods for suppressing an immune response, e.g., by inhibiting class II MHC-mediated activation of T cells. The subject compounds and methods may be used to treat or prevent disorders such as rheumatoid arthritis and/or multiple sclerosis.

24 Claims, 19 Drawing Sheets

```
                          SEQUENCE LISTING

<160> NUMBER OF SEQ ID NOS: 5

<210> SEQ ID NO 1
<211> LENGTH: 26
<212> TYPE: PRT
<213> ORGANISM: HIV

<400> SEQUENCE: 1

Cys Phe Ile Thr Lys Ala Leu Gly Ile Ser Tyr Gly Arg Lys Lys Arg
 1               5                  10                  15

Arg Gln Arg Arg Arg Pro Pro Gln Gly Ser
            20                  25

<210> SEQ ID NO 2
<211> LENGTH: 11
<212> TYPE: PRT
<213> ORGANISM: HIV

<400> SEQUENCE: 2

Tyr Gly Arg Lys Lys Arg Arg Gln Arg Arg Arg
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: indicator peptide

<400> SEQUENCE: 3
```

```
Tyr Ala Ala Phe Arg Ala Ala Ala Ser Ala Lys Ala Ala Ala
 1               5                  10

<210> SEQ ID NO 4
<211> LENGTH: 6
<212> TYPE: PRT
<213> ORGANISM: Artificial Sequence
<220> FEATURE:
<223> OTHER INFORMATION: enzyme activity control

<400> SEQUENCE: 4

Arg Ala Met Ala Ser Leu
 1               5

<210> SEQ ID NO 5
<211> LENGTH: 16
<212> TYPE: PRT
<213> ORGANISM: Artificial Sequence
<220> FEATURE:
<223> OTHER INFORMATION: enzyme activity control

<400> SEQUENCE: 5

Gln Tyr Ile Lys Ala Asn Ser Leu Phe Ile Gly Ile Thr Glu Leu Lys
 1               5                  10                  15
```

IMMUNOSUPPRESSANT COMPOUNDS, METHODS AND USES RELATED THERETO

This application is a national stage filing under 35 U.S.C. 371 of International Application PCT/US03/09219, filed Mar. 24, 2003, which claims priority from U.S. Provisional Application No. 60/367,123, filed Mar. 22, 2002. The entire teachings of the referenced Applications are incorporated herein by reference. International Application PCT/US03/09219 was published under PCT Article 21(2) in English.

BACKGROUND OF THE INVENTION

MHC molecules exist in two forms, class I and class II, both encoded within a single gene complex. MHC genes are highly polymorphic: most loci have up to about 100 alleles in the human population (Hansen, T. H., et al. 1993 In "Fundamental Immunology" Ed. Paul, W. E., RavenPress, New York, N.Y., p. 577).

Class I MHC molecules are 45 kD transmembrane glycoproteins, noncovalently associated with another glycoprotein, the 12 kD beta-2 microglobulin. The latter is not inserted into the cell membrane, and is encoded outside the MHC. Human class I molecules are of three different isotypes, termed HLA-A, -B, and -C, encoded in separate loci. The tissue expression of class I molecules is ubiquitous and codominant. The three-dimensional structure of several human and murine class I molecules have been resolved (Bjorkman, P. J., et al. (1987) Nature, 329, 506; Garrett, T. P. J., et al. (1989) Nature, 342, 692; Madden, D. R., et al. (1991) Nature, 353, 321; Fremont, D. H., et al. (1992) Science, 257, 919). Their first and second extracellular domains fold into a binding site consisting of a β-pleated sheet floor flanked by two parallel α-helical portions. The binding site presents 7-9 amino acid long antigenic peptides to cytotoxic effector T lymphocytes (Tc) (Madden et al. and Fremont et al., above). Most of these peptides arise from proteins synthesized inside the antigen presenting cell (APC), e.g., from proteins of viruses or other intracellular parasites, or from misfolded self proteins. The three class I isotypes, as well as their allelic forms, have different peptide binding specificities, depending on polymorphic residues within the binding site (Falk, K, et al. (1991) Nature, 351, 290; Falk, K, et al. (1992) Eur. J. Immunol., 22,277). There is an additional binding site on the third class I domain that interacts with CD8 molecules expressed selectively on Tc cells. The initial step in Tc cell activation is the simultaneous interaction of their antigen receptor (TCR) with the presented peptide and CD8 with its acceptor site on the same class I molecule.

Class II MHC molecules are noncovalently associated heterodimers of two transmembrane glycoproteins, the 35 kD α chain and the 28 kD β chain. In humans, class II molecules occur as three different isotypes, termed HLA-DP, -DQ, and -DR. Polymorphism in DR is restricted to the β chain, whereas both chains are polymorphic in the DP and DQ isotypes. Class II molecules are expressed codominantly, but in contrast to class I, exhibit a restricted tissue distribution: they are present only on the surface of cells of the immune system (constitutive expression on B lymphocytes and dendritic cells, and inducible expression on T cells and monocytes). The three-dimensional structure of three different DR molecules has been determined (Brown, J. H., et al. (1993), Nature, 364, 33; Stern, L. J., et al. (1994) Nature, 388, 215; Ghosh, P., et al. (1995) Nature, 378, 457; Dessen, A., et al. (1997) Immunity, 7, 473). Overall, their structure is very similar to that of class I molecules. The peptide binding site is composed of the first domains of α nd β chain, which, in contrast to class I, is open on both sides, allowing the binding of longer (12-24 residues long) peptides (Chicz, R. M., et al. (1992) Nature, 358, 764). An additional binding site on the second domain of β chains interacts with the CD4 molecule, expressed selectively on helper T (Th) cells. This molecule has a co-receptor function for Th cells, analogous to that of CD8 for Tc cells. During their biosynthesis and intracellular transport, class II heterodimers are chaperoned by a third, nonpolymorphic non-MHC-encoded 31 kD protein, termed invariant (Ii) chain (Cresswell, P. (1994) Annu. Rev. Immunol., 12, 259). The Ii chain shields the peptide binding site of class II molecules during their transport in the cytosol, until they reach an acidic endosomal compartment, where it is cleaved by proteases, leaving only a peptide thereof, termed CLIP, in the binding site. The exchange of CLIP with antigenic peptides is catalysed by another MHC-encoded molecule, termed HLA-DM, in the endosome (Vogt, A. B., et al. (1996) Proc. Natl. Acad. Sci. USA. 93, 9724). The antigenic peptides derive mostly from endocytosed external proteins (Germain, R. N. (1994) Cell, 76, 287).

The nature of interaction between DR molecules and peptides is largely understood. There is one major pocket in the binding site that is critical for the interaction with a hydrophobic anchor residue of the peptide, and additional minor pockets containing polymorphic β chain residues, which confer a degree of allotype-specificity to peptide binding (Stern et al., above; Hammer, J., et al. (1993) J. Exp. Med., 176, 1007; Hammer, J., et al. (1994) Cell. 74,197; Hammer, J., et al. (1994) Proc. Natl. Acad. Sci., USA 91, 4456; Hammer, J., et al. (1995) J. Exp. Med., 180, 2353). The peptide main chain also forms important hydrogen bonds with side chains of certain conserved residues in the binding site, which determine the overall conformation and side chain orientation of the bound peptide (Stern et al., above).

A large body of evidence has demonstrated that susceptibility to many diseases, in particular autoimmune diseases, is strongly associated with specific alleles of the major histocompatibility complex (reviewed in Tiwari, J., and Terasaki, P. (1985), HLA and disease association (New York; Springer Verlag)). Although some class I-associated diseases exist, most autoimmune conditions have been found to be associated with class II alleles. For example, class II alleles DRB1*0101, 0401, 0404, and 0405 occur at increased frequency among rheumatoid arthritis (RA) patients (McMichael, S. J., et al. (1977) Arthritis Rheum., 20, 1037; Stasny, P. (1978) N. Engl. J. Med., 298, 869; Ohta, N., et al. (1982) Hum. Immunol., 5, 123; Schiff, B., et al. (1982) Ann. Rheum. Dis., 41, 403), whereas DRB1*1501 is associated with multiple sclerosis (MS), and the DQ allele combination DQA1*0301/B1*0302 with insulin-dependent diabetes mellitus (IDDM). In RA, altogether >94% of rheumatoid factor positive patients carry one of the susceptibility alleles (Nepom, G. T., et al. (1989) Arthritis, Rheum., 32, 15).

The effect of DRB1 alleles on RA is manifested in different ways: first, the disease association shows ethnic-dependent preference for one or the other allele (Ohta et al., and Schiff et al., above), second, DRB1*0401 is associated with more severe forms of the disease than the other alleles (Lanchbury, J. S., et al. (1991) Hum. Immunol., 32, 56), and third, a gene dosage affect can be observed, in that homozygosity for a susceptibility allele or combinations of two susceptibility alleles confer more severe, chronic forms or juvenile onset of RA (Wordworth, P., et al. (1992) Am. J. Hum. Genet., 51, 585; Nepom, B. S. (1993) Clin. Immunol. Immunopathol., 67, 850). The latter finding indicates that the DRB1 locus can control both initiation and progression of the disease.

The DRB chains encoded by RA-linked DRB1 alleles exhibit polymorphic differences, but all share a stretch of identical, or almost identical amino acid sequence at positions 67-74, known as the "shared epitope" (Nepom et al., (1989) above; Gregersen, P. K., et al. (1987) Arthritis Rheum. 30, 1205). Residues in the shared epitope region contribute to the formation of the α helix on one side of the peptide binding groove (Brown et al., Stern et al., and Dessen et al., above), and are thus expected to influence peptide binding. Indeed, the basic residue Lys or Arg at position (p)71 of RA-associated DR allotypes imparts selectivity on peptide binding by favoring negative and disfavoring positive charge at residue p4 of the displayed peptide, whereas the RA-unlinked allotype DRB1*0402 with acidic residues Asp and Glu at p70 and 71 shows the opposite charge preference at residue p4 of the displayed peptide (Hammer, J., et al. (1995) J. Exp. Med., 181, 1847). Although the autoantigens inducing RA remain unknown, several joint cartilage proteins have peptide sequences which can selectively bind to RA-associated DR molecules due to an acidic residue at p4 (Dessen et al., Hammer et al., (1995) above). These proteins can thus be candidate antigens for an autoimmune response causing RA pathology (Rosloniec, E. F., et al. (1997) J. Exp. Med. 185, 1113). The opposite (positive) charge preference of DRB1-0402 has been shown to confer selective presentation of peptides with a basic residue at p4, derived from desmoglein 3, an autoantigen involved in the 0402-associated autoimmune disease, pemphigus vulgaris (Wucherpfennig, K. W., et al. (1995) Proc. Natl. Acad, Sci. USA, 92, 11935). These data strongly support the hypothesis that selective presentation of autoantigenic peptides by disease-linked MHC allotypes could be the mechanism underlying the genetic association between DRB1 alleles and autoimmune diseases (Todd, J. A., et al. (1988) Science, 240, 1003). The disease process itself is driven by Th cells recognizing such peptides. The activated autoreactive Th cells secrete different pro-inflammatory cytokines, which in turn attract further inflammatory cells to the site, and cause a chronic inflammation in the affected organ.

Of the two classes of MHC molecules, class II is the primary target for immunosuppressive intervention for the following reasons: First, MHC-II molecules activate T helper (Th) cells that are central to immunoregulation, and are responsible for most of the immunopathology in inflammatory diseases. Second, most autoimmune diseases are genetically associated with class II alleles. Third, under normal physiological or non-pathological conditions, MC-II molecules are expressed selectively on cells of the immune system, whereas MHC-I are present on most somatic cells.

Peptide binding to class II (e.g., DR) molecules requires the presence of defined side chains at so-called "anchor positions" of the displayed peptide, which all together form a particular binding motif; however, at non-anchor positions, a variation of side chains is permitted without influence on binding (Hammer et al., (1993, 1994, and 1995), above). This binding mechanism enables the presentation of many different peptides by a given allotype. The side chains at anchor positions interact with specific pockets within the binding site, whereas those at non-anchor positions point outward, and are available for recognition by the TCR of Th cells. It is therefore conceivable that replacement of autoantigenic peptides presented by autoimmune disease-associated MHC molecules by a compound having the same binding motif but being different at non-anchor positions could prevent the activation of autoimmune T cells, and thus interrupt the disease process. The mechanism whereby such a compound would exert its effect is competitive antagonism for the antigen-presenting site. Compounds binding selectively to class II molecules involved in a particular autoimmune disease are therefore expected to interfere specifically with that disease. Additional peptides which bind to MHC molecules and inhibit T cell activation have been disclosed in, for example, International Patent Applications WO 92/02543, WO 93/05011, and WO 95/07707.

A pharmaceutical agent targeting class II MHC molecules would offer several advantages over most available immunosuppressive drugs. First, it would represent a disease mechanism-based intervention, which is expected to interrupt the initial event in the pathogenic cascade. Second, it can be designed to be selective for only a few class II allotypes, i.e., binding with improved affinity to those allotypes associated with disease, leaving the remainder of the antigen presenting system available for protective responses against pathogens, and therefore causing fewer immunocompromising side effects than most immunosuppressive drugs. Third, the methods and compounds could be applied without any specific knowledge of the actual autoantigens causing the disease. Finally, it would be advantageous if such a pharmaceutical agent showed superior stability in certain biological environments. For example, high drug stability in mammalian plasmas such as rat, mouse or human plasma, would be desirable given that many cells of the immune system are found in the blood together with powerful peptide degrading enzymes. High drug stability in rodent plasma, especially rat plasma, is particularly advantageous since most therapeutics are initially tested for efficacy, toxicity, and/or pharmacokinetics in rodent models or systems. Drug stability against Cathepsin degradation is equally desirable since mechanism-based therapeutic intervention requires that pharmaceutical agents targeting class II MHC molecules may be endocytosed and transported within the cell using Cathepsin-containing endosomes before presentation to the MHC II molecule.

SUMMARY OF THE INVENTION

The present invention relates to compounds, pharmaceutical compositions and methods for suppressing an immune response, e.g., by inhibiting class II MHC-mediated activation of T cells. The compounds disclosed below, which include an unnatural arginine substitute in the compounds of Formula II, may exhibit increased stability in blood plasma (e.g., mouse and rat plasma) and increased binding affinity to MHC-class II molecules of interest (0401, 0101 and 0404) by as much as a factor of 1.25-3, as compared to corresponding compounds containing Arg in the position of the substitute amino acid. Further compounds disclosed below comprise a terminating group in the compounds of Formula I. Such compounds of Formulae I or II may also show increased in vivo inhibition of T-cell response by as much as a factor of 1.25-3. Such compounds may show effective immunosuppression in mouse models of certain immune disorders. The subject compounds and methods may be used to treat disorders such as rheumatoid aritis and/or multiple sclerosis.

In certain embodiments, the subject compounds are used for the preparation of a pharmaceutical composition for the treatment of an animal, such as a human, e.g., to treat or prevent a condition characterized by MHC class II-mediated activation of T cells, or by expression of MHC class II protein at a pathological site of inflammation, such as an autoimmune disease. The subject compounds and/or compositions may be used in the treatment or prevention of such diseases, including those enumerated specifically below.

DETAILED DESCRIPTION OF THE INVENTION

I. Introduction

Figure 1:
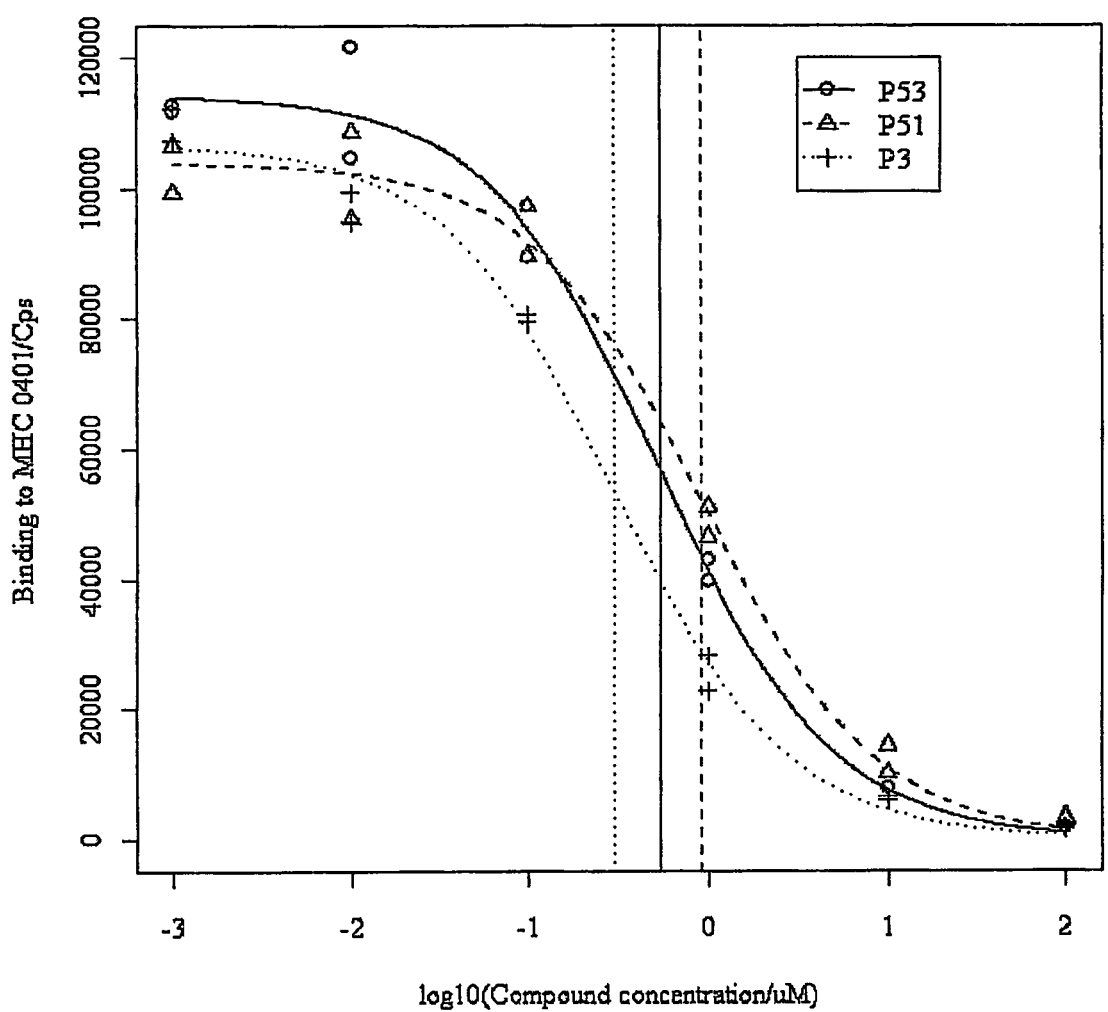
FIG. 1 Improved binding of a Gpg (guanylpiperidyl glycine)-containing heptamer compound of the invention (P53) to MHC class II protein 0401 compared to the Arg-containing equivalent (P51). A published lead peptide (P3; Falcioni et al 1999; Nature Biotech 17, 562-567) is used as a positive control. Using standard statistical software, non-linear logistic regression curves were fitted to replica data points generated according to Example 14. IC50s were estimated from the fitted curves and are represented by vertical lines of the appropriate line-type (P53 solid line, P51 dashed line, P3 dotted line) for the corresponding compound.
Figure 2:
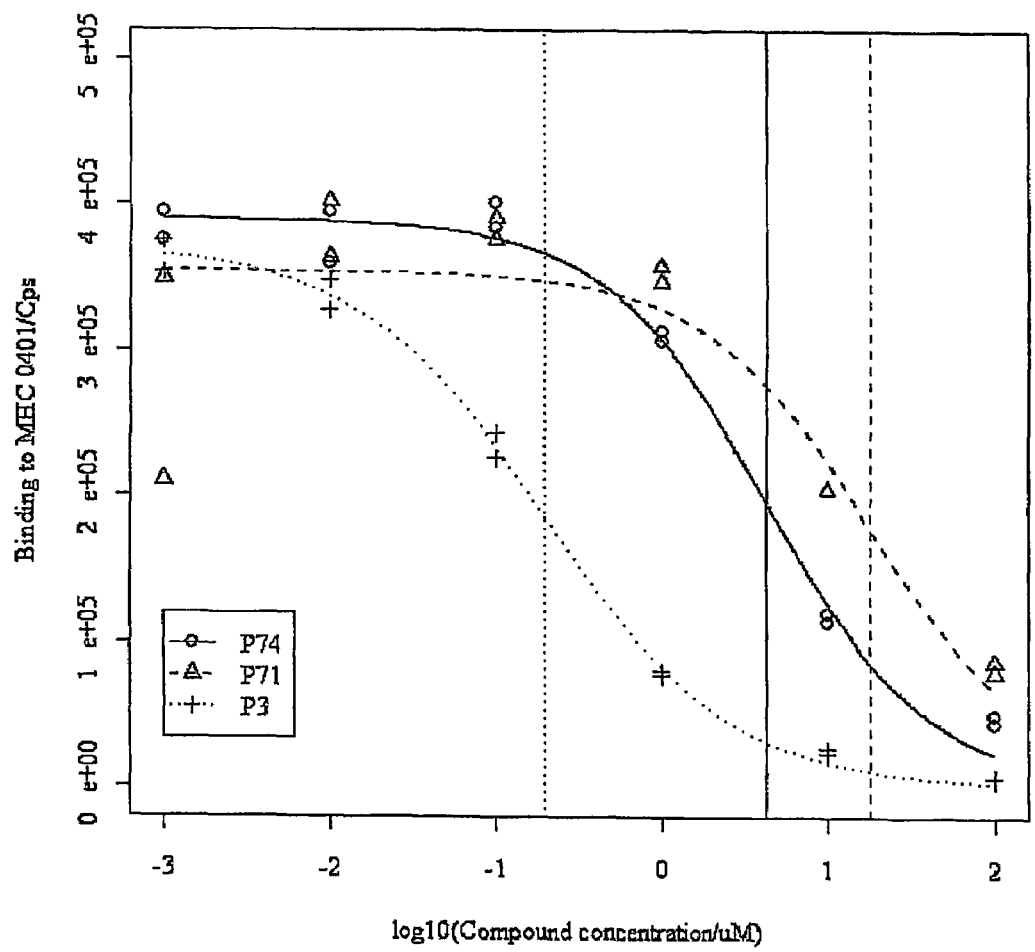
FIG. 2 Improved binding of a Gpg-containing tetramer compound of the invention (P74) to MHC class II protein 0401 compared to the Arg-containing equivalent (P71). A published lead peptide (P3; Falcioni et al 1999) is used as a positive control. Using standard statistical software, non-linear logistic regression curves were fitted to replica data points generated according to Example 14. IC50s were estimated from the fitted curves and are represented by vertical lines of the appropriate line-type (P74 solid line, P71 dashed line, P3 dotted line) for the corresponding compound.

The present invention relates to compounds, such as peptidomimetic compounds, which can be used to suppress an undesired immune activity, e.g., by inhibiting class II MHC-mediated T cell activation, such as in the treatment or prevention of autoimmune disorders. In certain embodiments, these compounds are characterized by binding to class II molecules, their ability to prevent the binding of self antigens or to displace self antigens already bound to class II molecules and/or their ability to inhibit T cell activation by modulating a class II MHC restricted immune response by an alternate mode of action. In such embodiments, compounds of the invention may be termed "inhibitors", "inhibiting agents", "subject inhibitors", "peptiodomimetics" (including "heptamer" and "tetramer" compounds), "compounds of the invention" or "inhibitors of the invention". In certain embodiments, the preferred class II molecules are DR isotypes. In preferred embodiments, such an inhibitor is a small molecule, e.g., a compound having a molecular weight less than 2000 amu, preferably less than 1000 amu, even more preferably less than 700 amu.

The compounds of the invention which inhibit class II MHC activity have therapeutic value in the prevention or treatment of various class II MHC-related diseases or disorders. The compounds of the invention may be administered to a patient for treatment of an immune disorder, for example, involving undesirable or inappropriate immune activity, or may be used to prepare a therapeutic medicament. In particular, an effective dose of an inhibitor of the invention may be therapeutically applied to ameliorate or to prevent insulin-dependent diabetes, multiple sclerosis, rheumatoid arthritis, etc. An effective dose of a compound of the invention for the treatment of a disorder involving undesirable or inappropriate MHC activity, such as an autoimmune disorder, can be determined by standard means known in the art taking into account routine safety studies, toxicity studies, dose concentration studies and method of delivery, e.g., bolus, continuous or repeated. In a particular embodiment, a dose of about 0.01 to about 500 mg/kg can be administered.

II. Definitions

As u sed herein, the term "MHC activity" refers to the ability of an MHC molecule to stimulate an immune response, e.g., by activating T cells. An inhibitor of MHC activity is capable of suppressing this activity, and thus inhibits the activation of T cells by MHC. In preferred embodiments, a subject inhibitor selectively inhibits activation by a particular class II MHC isotype or allotype. Such inhibitors may be capable of suppressing a particular undesirable MHC activity without interfering with all MHC activity in an organism, thereby selectively treating an unwanted immune response in an animal, such as a mammal, preferably a human, without compromising the animal's immune response in general. Such unwanted immune response may be one associated with a particular disease such as rheumatoid arthritis or multiple sclerosis.

The term "prodrug" is intended to encompass compounds that, under physiological conditions, are converted into the inhibitor agents of the present invention. A common method for making a prodrug is to select moieties which are hydrolyzed under physiological conditions to provide the desired biologically active drug. In other embodiments, the prodrug is converted by an enzymatic activity of the patient or alternatively of a target pathogen. "Treat", as used herein, means at least lessening the severity or ameliorating the effects of, for example, one or more symptoms, of a disorder or condition.

"Hydrophobic", as used herein when pertaining to a molecular species, means that in a partitioning experiment, the majority of the molecules of the molecular species under investigation is retained in the organic rather than the aqueous layer. Preferably, more than about 55%, 75%, 85%, or over about 95% of the molecule is retained in the organic layer. Suitable organic solvents for such a partitioning experiment will be known to a skilled artisan but include, without limitation, octanol, diethylether, dichloromethane, and chloroform. When pertaining to a functional group or residue, hydrophobic refers to the property of said functional group or residue to increase the hydrophobicity of a molecular species when added to it structurally.

"Prevent", as used herein, means to delay or preclude the onset of, for example, one or more symptoms of a disorder or condition.

The term "$IC_{50}$" means the concentration of a drug which inhibits an activity or property by 50%, e.g., by reducing the frequency of a condition, such as cell death, by 50%, by reducing binding of a competitor peptide to MHC II protein by 50% or by reducing the level of an activity, such as T-cell proliferation or IL2 secretion, by 50%.

The term "$ED_{50}$" means the dose of a drug that produces 50% of the maximum of a given response or effect. Alternatively, it may refer to the dose that produces a pre-determined response in 50% of test subjects or preparations.

The term "$LD_{50}$" means the dose of a drug that is lethal in 50% of test subjects.

The term "therapeutic index" refers to the therapeutic index of a drug defined as $LD_{50}/ED_{50}$.

The term "patient" refers to an animal, preferably a mammal, including humans as well as livestock and other veterinary subjects.

The term "structure-activity relationship" or "SAR" refers to the way in which altering the molecular structure of drugs alters their interaction with a receptor, enzyme, etc.

"Small molecule" refers to a molecule which has a molecular weight of less than about 2000 amu, or less than about 1000 amu, and even less than about 700 amu.

The term "aliphatic" refers to a linear, branched, or cyclic alkane, alkene, or alkyne. In certain embodiments, aliphatic groups in the present invention are linear or branched and have from 1 to about 20 carbon atoms.

The term "alkyl" refers to the radical of a saturated aliphatic group, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, a bout 20 or fewer. Likewise, cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN, and the like.

'Ci alkyl' is an alkyl chain having i member atoms. For example, C4 alkyls contain four carbon member atoms. C4 alkyls containing may be saturated or unsaturated with one or two double bonds (cis or trans) or one triple bond. Preferred C4 alkyls are saturated. Preferred unsaturated C4 alkyl have one double bond. C4 alkyl may be unsubstituted or substituted with one or two substituents. Preferred substituents include lower alkyl, lower heteroalkyl, cyano, halo, and haloalkyl.

'Heteroalkyl' is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkoxycarbonylphenylthio), amino (e.g., amino, mono- and di-C1-C3 alkylamino, methylphenylamino, methylbenzylamino, C1-C3 alkylamido, carbamamido, ureido, guanidino).

'Mi heteroalkyl' is a heteroalkyl chain having i member atoms. For example, M4 heteroalkyls contain one or two non-adjacent heteroatom member atoms. M4 heteroalkyls containing 1 heteroatom member atom may be saturated or unsaturated with one double bond (cis or trans) or one triple bond. Preferred M 4 heteroalkyl containing 2 heteroatom member atoms are saturated. Preferred unsaturated M4 heteroalkyl have one double bond. M4 heteroalkyl may be unsubstituted or substituted with one or two substituents. Preferred substituents include lower alkyl, lower heteroalkyl, cyano, halo, and haloalkyl.

The term "aralkyl" refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "heteroatom" refers to an atom of any element other than carbon or hydrogen. Illustrative heteroatoms include boron, nitrogen, oxygen, phosphorus, sulfur and selenium, and alternatively oxygen, nitrogen or sulfur.

The term "amino acid" refers to an organic compound bearing both a carboxylic acid group and an amino group, preferably attached to the same carbon atom or to adjacent carbon atoms, most preferably to the same carbon atom. Exemplary amino acids are those found in nature, such as amino acids that are used to synthesize proteins in cells, although unnatural amino acids such as those used in the Exemplification or otherwise known in the art are also contemplated. An "amino acid residue" refers to a derivative of an amino acid wherein either or both of the amino and carboxylic acid groups have been joined to another moiety, e.g., to form an amide, thioamide, sulfonamide, etc.

The term "amino acid analog" includes amino acid-like molecules, or residues thereof, wherein the carbonyl of the carboxylic acid group is replaced with another electrophilic moiety, such as a thiocarbonyl or sulfonyl group. The term also includes analogs of dipeptides, such as the [SΨ(oxaz)L] and [SΨ(imid)L] moieties discussed below, as well as analogs of dipeptides wherein the internal amide bond is replaced by an alkene. Other amino acid analogs suitable for use in the present invention are well known to those of skill in the art. Compounds, such as inhibitors of the invention, that comprise one or more amino acid analogs are often termed "peptidomimetic" or "mimetic" compounds.

The term "aryl" includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" refers to an aromatic or non-aromatic ring in which each atom of the ring is carbon.

The term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that may be represented by the general formulas:

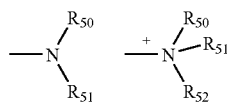

wherein $R_{50}$, $R_{51}$ and $R_{52}$ each independently represent a hydrogen, an alkyl, an alkenyl, —$(CH_2)_m$—$R_{61}$, or $R_{50}$ and $R_{51}$, taken together with the N atom to which they are attached complete a heterocycle having from 4 to 8 atoms in the ring structure; $R_{61}$, represents an aryl, a cycloalkyl, a cycloalkenyl, a heterocycle or a polycycle; and m is zero or an integer in the range of 1 to 8. In certain embodiments, only one of $R_{50}$ or $R_{51}$ may be a carbonyl, e.g., $R_{50}$, $R_{51}$ and the nitrogen together do not form an imide. In other embodiments, $R_{50}$ and $R_{51}$ (and optionally $R_{52}$) each independently represent a hydrogen, an alkyl, an alkenyl, or —$(CH_2)_m$—$R_{61}$. Thus, the term "alkylamine" includes an amine group, as defined above, having a substituted or unsubstituted alkyl attached thereto, i.e., at least one of $R_{50}$ and $R_{51}$ is an alkyl group.

The term "acylamino" is art-recognized and refers to a moiety that may be represented by the general formula:

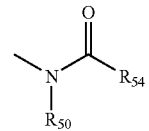

wherein $R_{50}$ is as defined above, and $R_{54}$ represents a hydrogen, an alkyl, an alkenyl or —$(CH_2)_m$—$R_{61}$, where m and $R_{61}$ are as defined above.

The term "amido" is art recognized as an amino-substituted carbonyl and includes a moiety that may be represented by the general formula:

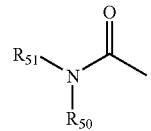

wherein $R_{50}$ and $R_{51}$ are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$13 $R_{61}$, wherein m and $R_{61}$ are defined above. Representative alkylthio groups include methylthio, ethyl thio, and the like.

The term "carbonyl" is art recognized and includes such moieties as may be represented by the general formulas:

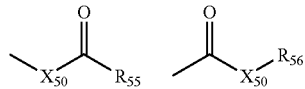

wherein $X_{50}$ is a bond or represents an oxygen or a sulfur, and $R_{55}$ represents a hydrogen, an alkyl, an alkenyl, —$(CH_2)_m$—$R_{61}$ or a pharmaceutically acceptable salt, $R_{56}$ represents a hydrogen, an alkyl, an alkenyl or —$(CH_2)_m$—$R_{61}$, where m and $R_{61}$ are defined above. Where $X_{50}$ is an oxygen and $R_{55}$ or $R_{56}$ is not hydrogen, the formula represents an "ester". Where $X_{50}$ is an oxygen, and $R_{56}$ is as defined above, the moiety is referred to herein as a carboxyl group, and particularly when $R_{56}$ is a hydrogen, the formula represents a "carboxylic acid". Where $X_{50}$ is an oxygen, and $R_{55}$ is hydrogen, the formula represents a "formate". In general, where the oxygen atom of the above formula is replaced by sulfur, the formula represents a "thiocarbonyl" group. Where $X_{50}$ is a sulfur and $R_{55}$ or $R_{56}$ is not hydrogen, the formula represents a "thioester." Where $X_{50}$ is a sulfur and $R_{56}$ is hydrogen, the formula represents a "thiocarboxylic acid." Where $X_{50}$ is a sulfur and $R_{55}$ is hydrogen, the formula represents a "thioformate." On the other hand, where $X_{50}$ is a bond, and $R_{55}$ is not hydrogen, the above formula represents a "ketone" group. Where $X_{50}$ is a bond, and $R_{55}$ is hydrogen, the above formula represents an "aldehyde" group.

The terms "alkoxyl" or "alkoxy" refers to an alkyl group, as defined above, having an oxygen radical attached thereto.

Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—$R_{61}$, where m and $R_{61}$ are described above.

The term "sulfonate" is art recognized and includes a moiety that may be represented by the general formula:

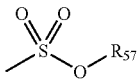

in which $R_{57}$ is an electron pair, hydrogen, alkyl, cycloalkyl, or aryl.

The term "sulfate" is art recognized and includes a moiety that may be represented by the general formula:

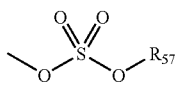

in which $R_{57}$ is as defined above.

The term "sulfonamido" is art recognized and includes a moiety that may be represented by the general formula:

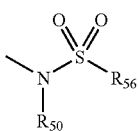

in which $R_{50}$ and $R_{56}$ are as defined above.

The term "sulfamoyl" is art-recognized and includes a moiety that may be represented by the general formula:

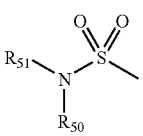

in which $R_{50}$ and $R_{51}$ are as defined above.

The term "sulfonyl" refers to a moiety that may be represented by the general formula:

in which $R_{58}$ is one of the following: hydrogen, alkyl, alkenyl, alkynyl, cycloalkyl, heterocyclyl, aryl or heteroaryl.

The term "sulfoxido" refers to a moiety that may be represented by the general formula:

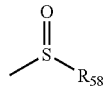

in which $R_{58}$ is defined above.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, p, etc., when it occurs more than once in any structure, is intended to be independent of its definition elsewhere in the same structure.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_{61}$, m and $R_{61}$ being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain monomeric subunits of the present invention may exist in particular geometric or stereoisomeric forms. In addition, oligomers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds that may be substituted or unsubstituted.

The phrase "protecting group" includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., *Protective Groups in Organic Synthesis* $2^{nd}$ ed., Wiley, N.Y., (1991).

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251-59, McGraw Hill Book Company, New York, (1977). The Hammett constant values are generally negative for electron donating groups ($\sigma(P)=-0.66$ for $NH_2$) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

Contemplated equivalents of the oligomers, subunits and other compositions described above include such materials which otherwise correspond thereto, and which have the same general properties thereof (e.g., biocompatible, antineoplastic), wherein one or more simple variations of substituents are made which do not adversely affect the efficacy of such molecule to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

III. Compounds of the Present Invention

The present invention provides peptidomimetic compounds that may suppress an immune response, e.g., by inhibiting class II MHC-mediated activation of T cells. For example, suitable peptidomimetics include compounds having a structure of Formula I:

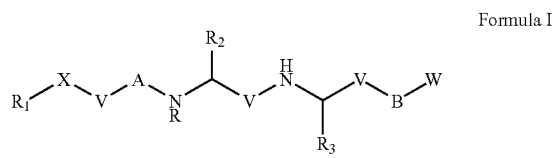

Formula I wherein, as valence and stability permit,

A is absent or represents a sequence of from one to four amino acid or amino acid analog residues, preferably is absent;

B represents a sequence of from two to eight amino acid or amino acid analog residues, preferably from two to six amino acid or amino acid analog residues;

X is absent or represents O, S, or NR;

W represents a terminating group, such as $OR_7$ or $NR_8R_9$;

V, independently for each occurrence, represents C=O, C=S, or $SO_2$;

R, independently for each occurrence, represents H or lower alkyl, preferably H;

$R_1$ represents a substituted or unsubstituted alkyl, heteroalkyl, alkenyl, alkynyl, aryl, aralkyl, heteroaryl, heteroaralkyl, cycloalkyl, cycloalkylalkyl, heterocyclyl, or heterocyclylalkyl moiety, preferably a hydrophobic moiety, most preferably comprising from 1 to 8 carbon atoms;

$R_2$ represents a substituted or unsubstituted alkyl, heteroalkyl, alkenyl, alkynyl, aryl, aralkyl, heteroaryl, heteroaralkyl, cycloalkyl, cycloalkylalkyl, heterocyclyl, or heterocyclylalkyl moiety, preferably a hydrophobic moiety, or $R_2$ and R, taken together, form a ring having from 5 to 7 members, optionally being substituted with from 1 to 5 substitutents and/or forming a polycyclic structure with one or more other rings, such as aryl, heterocyclyl, or carbocyclyl rings, e.g., a fused bicycle;

$R_3$ represents a substituted or unsubstituted alkyl, heteroalkyl, alkenyl, alkynyl, aryl, aralkyl, heteroaryl, heteroaralkyl, cycloalkyl, cycloalkylalkyl, heterocyclyl, or heterocyclylalkyl moiety, preferably including a basic nitrogen atom (e.g., that is protonated under physiological conditions and/or its conjugate acid has a pKa in aqueous solution between 6 and 12, preferably between 7 and 10); and $R_7$, $R_8$ and $R_9$ independently represent substituents selected from H and substituted or unsubstituted alkyl, heteroalkyl, aryl, aralkyl, heteroaralkyl, heteroaryl, cycloalkyl, cycloalkylalkyl, heterocyclyl, and heterocyclylalkyl, or where $R_8$ and $R_9$, taken togther, form a ring havng from 5 to 7 members, optionally being substituted with from 1 to 5 substitutents and/or forming a polycyclic structure with one or more other rings, such as aryl, heterocyclyl, or carbocyclyl rings.

The present invention provides peptidomimetic compounds that may suppress an immune response, e.g., by inhibiting class II MHC-mediated activation of T cells. For example, suitable peptidomimetics include compounds having a structure of Formula II:

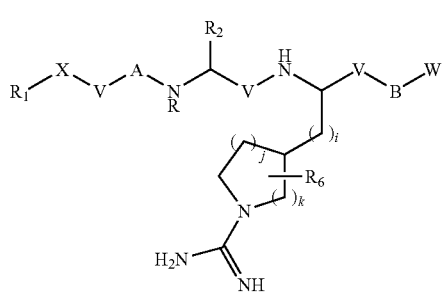

Formula II wherein, as valence and stability permit,

A is absent or represents a sequence of from one to four amino acid or amino acid analog residues, preferably is absent;

B represents a sequence of from two to eight amino acid or amino acid analog residues, preferably from two to six amino acid or amino acid analog residues;

X is absent or represents O, S, or NR;

W represents $OR_7$ or $NR_8R_9$;

V, independently for each occurrence, represents C=O, C=S, or $SO_2$;

R, independently for each occurrence, represents H or lower alkyl, preferably H;

$R_1$ represents a substituted or unsubstituted alkyl, heteroalkyl, alkenyl, alkynyl, aryl, aralkyl, heteroaryl, heteroaralkyl, cycloalkyl, cycloalkylalkyl, heterocyclyl, or heterocyclylalkyl moiety, preferably a hydrophobic moiety, most preferably comprising from 1 to 8 carbon atoms;

$R_2$ represents a substituted or unsubstituted alkyl, heteroalkyl, alkenyl, alkynyl, aryl, aralkyl, heteroaryl, heteroaralkyl, cycloalkyl, cycloalkylalkyl, heterocyclyl, or heterocyclylalkyl moiety, preferably a hydrophobic moiety, or $R_2$ and R, taken together, form a ring having from 5 to 7 members, optionally being substituted with from 1 to 5 substitutents and/or forming a polycyclic structure with one or more other rings, such as aryl, heterocyclyl, or carbocyclyl rings, e.g., a fused bicycle;

i represents an integer from 0-1, preferably 0;

j represents an integer from 1-2, preferably 1;

k represents an integer from 1-3, preferably 2;

$R_6$ is absent or represents from 1-4 substitutents on the nitrogen-containing ring to which it is attached, selected from substituted or unsubstituted lower alkyl, haloalkyl, halogen, hydroxyl, and amino; and $R_7$, $R_8$ and $R_9$ independently represent substituents selected from H and substituted or unsubstituted alkyl, heteroalkyl, aryl, aralkyl, heteroaralkyl, heteroaryl, cycloalkyl, cycloalkylalkyl, heterocyclyl, and heterocyclylalkyl, or where $R_8$ and $R_9$, taken togther, form a ring havng from 5 to 7 members, optionally being substituted with from 1 to 5 substitutents and/or forming a polycyclic structure with one or more other rings, such as aryl, heterocyclyl, or carbocyclyl rings.

In certain embodiments of Formula I, $R_3$ represents a side-chain of arginine or lysine or a side chain having the structure of

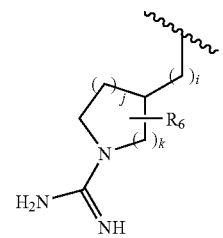

wherein i, j, k, and $R_6$ are defined as described for Formula II.

In certain embodiments of Formula I, $R_3$ includes a guanidine or guanidinium moiety, e.g., included in or attached to a ring or included in or at the terminus of a chain. In certain embodiments of Formula I, $R_3$ represents a cycloalkyl, alkyl, or an aminoalkyl group, such as a side-chain of allo-isoleucine, cyclohexylglycine, citrulline, lysine, or ornithine, including N-methyl and N,N-dimethyl variants of lysine, citrulline, and ornithine.

In certain embodiments of Formula I, B represents two amino acid or amino acid analog residues and W includes a terminating group as described in greater detail below. Preferably, the amino acid or analog residues are attached through secondary amide bonds (i.e., wherein the nitrogens bear a hydrogen substituent).

In certain embodiments of Formula II, $R_6$ is absent, and in other embodiments, $R_6$ includes a lower alkyl substituent.

In certain embodiments of Formula I and II, $R_2$ represents substituted or unsubstituted cycloalkyl, cycloalkylalkyl, aryl, aralkyl, In certain embodiments of Formulae I and II, the first residue of B (the amino acid or analog residue attached to V) has a side-chain that is H or, preferably, a C1-C8 alkyl or M1-M8 heteroalkyl (including, for example, alanine, Acm-cysteine, Prm-cysteine, acetyl-cysteine, and Nva, e.g., C1-C6 alkyl or M1-M6 heteroalkyl), or a substituted or unsubstituted aryl, aralkyl, heteroaryl, or heteroalkyl (e.g., methylphenyl or phenylmethyl) or the first residue of B is an amino acid analog comprising a 5-8-membered nitrogen-containing heterocyclyl ring bearing a C=O, C=S, or $SO_2$ group, optionally fused to a benzene ring (e.g., Tic, azaTic, Disc, Thiq, etc.). Preferred residues at this position include Tic and Disc, although any residue employed at this position in the examples of Tables 1-3 may be present at this position.

In certain embodiments of Formulae I and II, the second residue of B (the amino acid or analog residue attached to V being the first) has a side-chain that is H or, preferably, a C1-C6 alkyl, M1-M6 heteroalkyl, or cycloalkyl, even more preferably C3-C5 alkyl or M 3-M5 heteroalkyl, either branched or unbranched, or cycloalkyl. Exemplary residues include glycine, isoleucine, Nle, Chg, Met(O) (oxidized methionine), and alpha-aminoisobutyric acid. In certain embodiments, the second residue of B is a residue that is substantially isometric with a dipeptide, such as on Odapdc or Haic residue (as defined below). Preferred residues at this position include Met and Nle, although any residue employed at this position in the examples of Tables 1-3 may be present at this position.

In certain embodiments of Formulae I and II, R and $R_2$ are not taken together to form a ring. In embodiments wherein R and $R_2$ taken together form a ring, the ring is preferably a 6- or 7-membered ring, or is a substituted (e.g., bicyclic) 5-membered ring.

In certain embodiments of Formulae I and II, $R_1XV$, taken together, represent an alkanoyl, alkenoyl, aryl carbonyl, or an aminoalkanoyl group. In certain such embodiments, the acyl group is a benzoyl group, a lower alkanoyl group, or a lower aminoalkanoyl group, such as an acetyl, propanoyl, amino-propanoyl, or aminobutanoyl group.

In certain embodiments of Formulae I and II, B represents from 2 to 6 amino acid or amino acid analog residues, preferably 2 to 5 amino acid or amino acid analog residues. In certain embodiments, particularly wherein B represents four or fewer amino acid or amino acid analog residues, preferably three or fewer, W represents a terminating group. Exemplary terminating groups are depicted in Table 1 (a, b and c), and include nitrogen atoms (e.g., forming an amide with a terminal carboxyl of B) bearing substituents selected from H, substituted and unsubstituted alkyl, aryl, aralkyl, heteroaralkyl, heteroaryl, cycloalkyl, cycloalkylalkyl, heterocyclyl, and heterocyclylalkyl, preferably from H, substituted and unsubstituted alkyl, aryl, aralkyl, cycloalkyl, and cycloalkylalkyl. Suitable substituents include hydroxyl, ether, and amino substituents. Preferably, a terminating group includes at least six non-hydrogen atoms including the nitrogen attached to B, preferably at least eight non-hydrogen atoms. Preferably, a terminating group W includes a nitrogen substituted with an aralkyl or heteroaralkyl substituent, such as a benzyl or phenethyl substituent. In certain such embodiments, the nitrogen bears a second substituent selected from H, lower alkyl, hydroxy-lower alkyl, and hydroxy-lower alkyl-O-lower alkyl. In certain embodiments, a terminating group W is a nitrogen-containing heterocyclyl substituent, preferably fused with an aryl or heteroaryl ring, attached to B through the nitrogen atom of the ring. Such terminating groups include tetrahydroisoquinoline, indoline, isoindoline, morpholine, piperidine, etc.

Certain embodiments of Formulae I and II, such as by appropriate selection of $R_1$ or W, preferably $R_7$, $R_8$ or $R_9$, may provide a prodrug that is converted to an active compound of the invention under physiological conditions. For example, where W is part of an ester, the ester can be cleaved under physiological conditions.

In certain embodiments of Formulae I and II, at least one of $R_1$, $R_7$, $R_8$ or $R_9$ is a hydrophobic residue, preferably $R_8$ or $R_9$. In other embodiments, the hydrophobicity of the compound, for example as estimated using the method of Meyan et al., 1995 (J. Pharm Sci. 84:83-92), lies between a cLogP of around 2.0 to around 6.0, preferably between around 3.0 to around 6.0 most preferably between around 4.0 to around 5.5. However, compounds that possess an estimated cLogP value of outside this range are contemplated by this invention, for example compounds having a cLogP of around 3.0 to around 4.0.

In certain embodiments of Formulae I and II, A and B together include between 2 and 8, e.g., between 3 and 6 amino acid or amino acid analog residues. Preferably, A and B together include around 2 or around 5 amino acid or amino acid analog residues.

The portion of Formulae I and II flanked by (but not including) B and ($VCHR_2$) is referred to herein as an 'arginine-like' residue. In embodiments wherein i represents 0, j represents 1, and k represents 2, the arginine-like residue is referred to herein as a Gpg residue (guanylpiperidyl glycine). Such residues are known in the art, and are described in PCT publication WO 00/78796 and references cited therein. In preferred embodiments, the arginine-like residue is enriched for an S-configuration at the alpha stereocenter of the amino acid, e.g., preferably is at least 60%, 75%, 85%, 90%, or even 95% or more enriched for the S-enantiomer of this residue. In certain embodiments, subject inhibitors display increased stability, e.g., have a plasma half-life at least 1.25, 1.5, or preferably 3 times as long, preferably at least five times as long, and increased binding affinity with an MHC Class II molecule (e.g., 0401, 0101, or 0404), e.g., bind with an affinity at least 1.25, 1.5, or preferably 3 times as great, as an analogous peptidyl compound wherein the arginine-like residue is replaced by arginine.

Other references which describe arginine-like residues useful in the present invention include International Applications Nos. WO 99/61476 and WO 01/27141, Jones et al., *Bioorg. Med. Chem. Lett.* 1999, 9, 2109-2114; Cunningham et al., *Bioorg. Med. Chem. Lett.* 1997, 7, 19-24; Hanson et al., *Bioorg. Med. Chem. Lett.* 1996, 6, 1931-1936; Jones et al., *Bioorg. Med. Chem. Lett.* 1999, 9, 2115-2118, Tamura et al., *Bioorg. Med. Chem. Lett.* 2000, 10, 745-49, Falcioni et al., 1999, *Nature Biotech* 17, 562-567, and Schmidt et al., *Proc. Am. Pept. Symp.*, $16^{th}$ (2000), Meeting Date 1999, 634-635.

In certain embodiments of Formula I and Formula II, the amino acids of A and/or B include a transcellular polypeptide sequence, such as are described in U.S. Pat. No. 6,495,526. The transcellular polypeptide sequence can be an internalizing peptide, such as may be derived from a polypeptide selected from antepennepedia protein, HIV transactivating (TAT) protein, mastoparan, melittin, bombolittin, delta hemolysin, pardaxin, Pseudomonas exotoxin A, clathrin, Diphtheria toxin and C9 complement protein, or a fragment thereof.

In one embodiment, the internalizing peptide is derived from the *drosophila* antepennepedia protein, or homologs thereof. The 60 amino acid long long homeodomain of the homeo-protein antepennepedia has been demonstrated to translocate through biological membranes and can facilitate the translocation of heterologous polypeptides to which it is coupled. See for example Derossi et al. (1994) *J Biol Chem* 269:10444-10450; and Perez et al. (1992) *J Cell Sci* 102:717-722. Recently, it has been demonstrated that fragments as small as 16 amino acids long of this protein are sufficient to drive internalization. See Derossi et al. (1996) *J Biol Chem* 271:18188-18193. The present invention contemplates coupling at least a portion of the antepernepedia protein (or homolog thereof) to a peptide or peptidomimetic of Formula I or II to increase the transmembrane transport of the compound, relative to the compound alone, by a statistically significant amount.

Another example of an internalizing peptide is the HIV transactivator (TAT) protein. This protein appears to be divided into four domains (Kuppuswamy et al. (1989) *Nucl Acids Res.* 17:3551-3561). Purified TAT protein is taken up by cells in tissue culture (Frankel and Pabo, (1989) *Cell* 55:1189-1193), and peptides, such as the fragment corresponding to residues 37-62 of TAT, are rapidly taken up by cell in vitro (Green and Loewenstein, (1989) *Cell* 55:1179-1188). The highly basic region mediates internalization and targeting of the internalizing moiety to the nucleus (Ruben et al., (1989) *J. Virol.* 63:1-8). Peptides or analogs that include a sequence present in the highly basic region, such as CFIT-KALGISYGRKKRRQRRRPPQGS, or a sub sequence thereof such as YGRKKRRQRRR, can be conjugated to compounds of Formula I or II to aid in internalization and targeting those compounds to the intracellular milieu.

In certain such embodiments, the amino acid sequence of A or B is longer than defined with respect to Formula I or II to permit attachment of an amino acid sequence of sufficient length to promote internalization of the compound.

Particularly preferred compounds of the invention are set forth below as P53, P74, P101, P102 and P69, most preferably P69 (see Table 1a).

The compounds of the invention can also serve as lead compounds for the development of analog compounds. The analogs should have a stabilized electronic configuration and molecular conformation that allows key functional groups to be presented to for example MHC class II protein in substantially the same way as the lead compound. In particular, the analog compounds have spatial electronic properties which are comparable to the binding region, but can be larger or smaller molecules than the lead compound. Identification of analog compounds can be performed through use of techniques such as self-consistent field (SCF) analysis, configuration interaction (CI) analysis, and normal mode dynamics analysis. Thus, the compounds of the present invention can be further modified as a lead compound to achieve (h) modified site of action, spectrum of activity, organ specificity, and/or
(i) improved potency, and/or
(j) decreased toxicity (improved therapeutic index), and/or
(k) decreased side effects, and/or
(l) modified onset of therapeutic action, duration of effect, and/or
(m) modified pharmakinetic parameters (resorption, distribution, metabolism and excretion), and/or
(n) modified physico-chemical parameters (solubility, hygroscopicity, color, taste, odor, stability, state), and/or
(O) improved general specificity, organ/tissue specificity, and/or
(p) optimized application form and route by
(q) esterification of carboxyl groups, or
(r) esterification of hydroxyl groups with carbon acids, or
(s) esterification of hydroxyl groups to, e.g. phosphates, pyrophosphates or sulfates or hemi succinates, or
(t) formation of pharmaceutically acceptable salts, or
(u) formation of pharmaceutically acceptable complexes, or
(v) synthesis of pharmacologically active polymers, or
(w) introduction of hydrophylic moieties, or
(x) introduction/exchange of substituents on aromates or side chains, change of substituent pattern, or
(y) modification by introduction of isosteric or bioisosteric moieties, or
(z) synthesis of homologous compounds, or
(aa) introduction of branched side chains, or
(bb) conversion of alkyl substituents to cyclic analogues, or
(cc) derivatisation of hydroxyl group to ketales, acetales, or
(dd) N-acetylation to amides, phenylcarbamates, or
(ee) synthesis of Mannich bases, imines, or
(ff) transformation of ketones or aldehydes to Schiff's bases, oximes, acetales, ketales, enolesters, oxazolidines, thiozolidines or combinations of any one thereof. The various steps recited above are generally known in the art. For example, computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, N.Y., N.Y. 10010 U.S.A. and Organic Synthesis, Wiley, New York, USA. Furthermore, peptide mimetics and/or computer aided design of appropriate derivatives and analogues can be used, for example, according to the methods described above. Methods for the lead generation in drug discovery also include using proteins and detection methods such as mass spectrometry (Cheng et al. J. Am. Chem. Soc. 117 (1995), 8859-8860) and some nuclear magnetic resonance (NMR) methods (Fejzo et al., Chem. Biol. 6 (1999), 755-769; Lin et al., J. Org. Chem. 62 (1997), 8930-8931). They may also include or rely on quantitative structure-action relationship (QSAR) analyses (Kubinyi, J. Med. Chem. 41 (1993), 2553-2564, Kubinyi, Pharm. Unserer Zeit 23 (1994), 281-290) combinatorial biochemistry, classical chemistry and others (see, for example, Holzgrabe and Bechtold, Pharm. Acta Helv. 74 (2000), 149-155).

The present invention further relates to therapeutic preparations comprising a subject compound and an excipient, such as a pharmaceutically acceptable or sterile excipient. The invention further relates to a method for treating or preventing a condition characterized by MHC-II-mediated activation of T cells, comprising administering to an animal, such as a human, a composition comprising a compound as set forth above. The invention further relates to uses of a subject compound for the preparation of a pharmaceutical composition. Such pharmaceutical composition may be suitable for the treatment or prevention of a condition characterized by MHC-II-mediated activation of T cells. In certain embodiments, the condition is an autoimmune disorder, e.g., rheumatoid arthritis or multiple sclerosis.

In certain embodiments, a subject inhibitor is selective for one therapeutic isotype or allotype, such as HLA-DR or DRB1*0101, over a second isotype or allotype, or over most other isotypes or allotypes. Thus, a subject inhibitor may have an $ED_{50}$ at least 5 or 10 times lower for one isotype or allotype, preferably at least 100 times lower, even more preferably at least 1000 times lower, over one or more other HLA isotypes or allotypes. Similarly, a subject inhibitor may have an $IC_{50}$ at least 5 or 10 times lower for one isotype or allotype, preferably at least 100 times lower, even more preferably at least 1000 times lower, over one or more other HLA isotypes or allotypes.

In certain embodiments, the invention provides a method of conducting a pharmaceutical business by selecting one or more compounds as disclosed herein for their ability to bind to MHC class II protein, conducting therapeutic profiling of said compound for efficacy and toxicity in animals, preparing a package insert describing the use of said compound for suppressing an immune response, and marketing the multivalent composition for suppressing an immune response. The invention also provides a kit comprising a compound as disclosed herein and instructions for administering the compound to suppress an immune response.

In another embodiment, the invention provides a method of conducting a life science business by selecting one or more compounds as described herein for their ability to bind to MEC class II protein, and licensing, jointly developing, or selling to a third party, the rights for manufacturing, marketing, selling or using said compound for suppressing an immune response.

IV. Therapeutic Applications

The subject compounds can be utilized for a wide range of medical treatments. For example, subject compounds may be employed in conjunction with solid organ transplants. Preferably, the organ is selected from the group consisting of heart, liver, kidney, adrenal cortex, lung, intestine, pancreas, cornea and skin. Most preferably, the target organ is selected from the group consisting of heart, kidney, liver, cornea, and skin. For example, a patient may be treated with a subject compound before or after receiving a transplant or allograft to prevent or ameliorate immune reactions that might lead to rejection of the transplant or graft vs. host disease. Sustained releases of the subject compounds, e.g., from a biodegradable polymer implant, or from biodegradable polymeric microparticles or nanoparticles, are also contemplated.

The compounds of the invention are also useful in treating diseases of the immune system characterized by unwanted, dysfunctional, or aberrant activation of T cells by MHC class II polypeptides. Such immune diseases include, but are not limited to, rheumatoid arthritis, juvenile arthritis, multiple sclerosis, Grave's disease, insulin-dependent diabetes, narcolepsy, psoriasis, systemic lupus erythematosus, ankylosing spondylitis, allograft rejection, Hashimoto's disease, myasthenia gravis, pemphigus vulgaris, thyroiditis, glomerulonephritis, insulitis, irritable bowel disease, pancreatitis, and primary biliary cirrhosis. Other disorders for which the compounds of the invention may be employed to relieve the symptoms of, treat or prevent the occurrence or reoccurrence of include, for example, Sjogren syndrome, scleroderma, polymyositis, dermatomyositis, bullous pemphigoid, Goodpasture's syndrome, autoimmune hemolytic anemia, pernicious anemia, idiopathic thrombocytopenic purpura, and Addison's disease, and the like. For such treatments, the compounds described herein may be administered in an amount sufficient to inhibit MHC-II mediated T cell activation by a therapeutically acceptable amount.

Specific autoimmune dysfunctions are often correlated with specific MHC types. DQ/DR haplotypes in humans and their associations with autoimmune diseases are well known, as described in U.S. Pat. No. 6,045,796. In certain embodiments, it may be advantageous to determine the genotype and/or phenotype of a patient to be treated with a subject inhibitor, e.g., to select a drug suitable for treating a disease or condition associated with the patient's haplotype, or to determine a patient's genotype and/or phenotype, as appropriate, for the selection and/or prescription of a particular drug. In a preferred embodiment, the association between a disease and specific MHC types is so strong that determining the genotype and/or phenotype of a patient may not be required. Methods for determining the haplotype of an animal, such as a human, are well known in the art, and any suitable technique may be used to make such a determination, for example, by analyzing DNA restriction fragment length polymorphism (RFLP) using DNA probes that are specific for the MHC locus being examined. Methods of preparing probes for the MHC loci are known to those skilled in the art. See, for example, Gregersen et al., (1986), Proc. Natl. Acad. Sci. U.S.A. 79:5966, which is incorporated herein by reference. The patient's haplotype may then be compared with haplotypes with known disease associations. As an example, over 90% of rheumatoid arthritis patients have a haplotype of DR4(Dw4), DR4(Dw14), or DR1. In particular, juvenile rheumatoid arthritis (e.g., pauciarticular juvenile rheumatoid arthritis) is associated with HLA-DPB2.1 (Begovich et al., 1989, PNAS 86:9489-9493). Approximately 70% of patients with insulin-dependent diabetes mellitus express HLA-DQ3.2B, DQA1, or DQB1, and susceptibility to the autoimmune dermatologic disease pemphigus vulgaris is linked to expression of HLA-DQB1.3 (Scharf et al., 1989, PNAS 86:6215-6219). Allergic reactions to ragweed are known to be associated with DR2 alleles. Marsh et al., (1989) Cold Spring Harb Symp Quant Biol 54:459-70, which is incorporated herein by reference.

Methods for In Vitro Testing

The biological activity of the inhibitor, e.g., the ability to inhibit antigen-specific T cell activation, may be assayed in a variety of systems. In one method, purified class II MHC molecules are incorporated into phospholipid vesicles by detergent dialysis. The resultant vesicles are then allowed to fuse to clean glass cover slips to produce on each a planar lipid bilayer containing MHC molecules (Brian and McConnell, Proc. Natl. Acad. Sci. USA (1984) 81: 6159). The inhibitors to be tested are detectably labeled and then incubated on the plates with purified MHC proteins which have been formulated into lipid membrane bilayers. Inhibitors that bind to the MHC molecules are identified by detecting label bound to the plate.

In a second exemplary protocol, an excess of inhibitor is incubated with an antigen-presenting cell expressing an MHC allotype of interest, (e.g., a DR of interest) and a T cell clone which recognizes a selected peptide (e.g., tetanus toxin 830-843) and MHC molecule (e.g., the DR of interest), and the antigenic peptide itself. The assay culture is incubated for a sufficient time for T cell proliferation, such as four days, and proliferation is then measured using standard procedures, such as pulsing with tritiated thymidine during the last 18 hours of incubation. The percent inhibition, compared to controls which received no inhibitor, is then calculated.

A third protocol is described in U.S. Pat. No. 5,736,507. In that disclosure, the peptide binding studies were performed using an improved version of a semi-quantitative binding assay described previously (Joosten et al., Int. Immunol. 6:751, 1994). Adapted for the present invention, purified MHC molecules (0.5-500 nM) may be incubated at pH=5.0 with 50 nM biotinylated indicator peptide and a concentration range of inhibitor in a final volume of 25 µl binding buffer (e.g., PBS, 1 mM AEBSF, 1 mM N-ethyl maleimide, 8 mM EDTA, 10 µM pepstatin A, 0.01% $NaN_3$, 0.05% NP-40 and 5% DMSO) may be employed.

After approximately 45 hours incubation at room temperature, bound and unbound indicator peptides may be separated either by SDS-PAGE in combination with blotting on a nitrocellulose filter (BioRad) or by vacuum DOT blotting using a nitrocellulose filter (BioRad) and 96 wells Hybry Dot equipment (BRL). Blots may be blocked with 0.5% DNA blocking reagent (Boehringer Mannheim, Germany) in 0.1 M maleic acid pH=7.5, 150 mM NaCl. After ½ hour, blots are washed in PBS, 0.02% Tween 20 (Sigma, St. Louis, USA) and incubated with Streptavidin-HRPO (Southern Biotechnology) in a 1:40,000 or 1:5,000 dilution respectively. DR-bound, biotinylated indicator peptide is detected by enhanced chemoluminescence using a Western Blot ECL kit (Amersham, U.K.) according to the manufacturer's instructions. Preflashed films (hyperfilm-ECL, Amersham, U.K.) are exposed for 10 minutes. The relative binding affinity of a given peptide is related to competition with the indicator peptide. This relative affinity is defined as the inhibitor concentration at which the signal is reduced to 50% ($^R IC_{50}$).

A similar protocol, detailed in the Exemplification below, is based on the protocol taught by Siklodi et al., Human Immunology, 59 (1998) 463-471, and employs competitive binding of subject inhibitors. Any suitable MHC-II allotype may be employed in such assays, and, as described below, the method is suitable for screening libraries of compounds for their ability to bind MHC-II molecules.

Other suitable methods to determine the in-vitro biological activity of an inhibitor may be taken from the examples below.

Model Systems for In Vivo Testing

The capacity of compounds to inhibit antigen presentation in an in vitro assay has been correlated to the capacity of the compounds to inhibit an immune response in vivo. In vivo activity may be determined in animal models, for example, by administering an antigen known to be restricted to the particular MHC molecule of interest, together with a test inhibitor of the present invention. T lymphocytes are subsequently removed from the animal and cultured with a dose range of antigen. Inhibition of stimulation is measured by conventional means, e.g., pulsing with $^3$H-thymidine, and comparing to appropriate controls. Preferably, as described in the Exemplification below, an animal model will be genetically modified to express a human MHC class II allotype of interest in place of endogenous MHC class II molecules. Certain experimental details will of course be apparent to the skilled artisan. See also, Adorini, et al., Nature 334:623-625 (1988), and Ito et al. (1996) J. Exp. Med. 183:2635-2644, both incorporated herein by reference.

The following are exemplary model systems for diseases of the immune system, which can be used to evaluate the effects of the compounds of the invention on these conditions. A skilled artisan would be able, with no more than routine experimentation or research, to identify other models suitable for testing compounds of the invention against these and other diseases of the immune system.

Experimental autoimmune encephalomyelitis (EAE) is a model for multiple sclerosis (MS) that induced by immunization with a myelin protein, e.g., myelin basic protein (MBP), proteolipid protein (PP) or mouse oligodendrocyte glycoprotein (MOG), in mice transgenic for an MS-associated human class II allotype and deficient of mouse class II molecules as described by Ito et al. (1996).

Collagen induced arthritis (CIA) is a model for rheumatoid arthritis (RA), induced by immunization with type II collagen in mice transgenic for an RA-associated human class II molecule (Rosloniec et al., J. Exp. Med. 185: 1113 (1997), & J. Immunol. 160: 2573-2578, (1998)).

V. Pharmaceutical Compositions

In another aspect, the present invention provides pharmaceutically acceptable compositions which comprise a therapeutically effective amount of one or more compounds of the subject invention, such as described above, formulated together with one or more pharmaceutically acceptable carriers (additives) and/or diluents for use in the treatment of aberrant T cell activation or an autoimmune disease, for example, rheumatoid arthritis or multiple sclerosis. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, capsules, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream, foam, or suppository. In certain embodiments, the pharmaceutical preparations may be non-pyrogenic, i.e., do not elevate the body temperature of a patient.

The phrase "therapeutically effective amount" as used herein means that amount of a compound, material, or composition comprising an inhibitor of the subject invention which is effective for producing some desired therapeutic effect. Such therapeutic effect may result from, for example, inhibition of unwanted T cell activation.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present subject compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of such inhibitors of MHC activity. These salts can be prepared in situ during the final isolation and purification of the compounds of the present invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of an inhibitor of an MHC activity such as T cell activation. These salts can likewise be prepared in situ during the final isolation and purification of the compounds of the present invention, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of inhibitor which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association an inhibitor of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An inhibitor of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulations so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract such as the small or large intestines, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active inhibitor(s) of the present invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active inhibitor.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active inhibitor, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the inhibitor of the present invention in the proper medium. Absorption enhancers can also be used to increase the flux of the drug across the skin. The rate of such flux can be controlled by either providing a rate controlling membrane or dispersing the compound of the present invention in a polymer matrix or gel.

Opthalmic formulations, eye ointments, powders, solutions and the like, are also contemplated as being within the scope of this invention.

Pharmaceutical compositions of this invention suitable for parenteral administration comprise one or more inhibitors of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and other antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the therapeutic effect of an inhibitor, it is desirable to slow the absorption of the inhibitor from subcutaneous or intramuscular injection. This may be accomplished by the use of a liquid suspension of crystalline or amorphous material having poor water solubility. The rate of absorption of the inhibitor then depends upon its rate of dissolution which, in turn, may depend upon crystal size and crystalline form. Alternatively, delayed absorption of a parenterally administered inhibitor form is accomplished by dissolving or suspending the inhibitor in an oil vehicle.

Injectable depot forms are made by forming microencapsuled matrices of the subject inhibitors in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

In certain embodiments, a compound as described herein is administered conjointly with another therapeutic agent, e.g., another immunosuppressant agent, an agent or substance that triggers an unwanted immune response (for example, transplanted cells), or an agent that acts together with the immunosuppressant to achieve a desired therapeutic effect, such as an antiiflammatory agent. For example, the compound and agent or substance can be administered in a single composition such as a tablet, in separate compositions simultaneously, or in separate compositions at different times as part of a therapeutic regimen, etc.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the inhibitors useful in the subject method may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response, e.g., amelioration of symptoms of rheumatoid arthritis or multiple sclerosis, for a particular patient, composition, and mode of administration, without being toxic to the patient.

The selected dosage level will depend upon a variety of factors including the activity of the particular inhibitor employed, or the ester, salt or derivative thereof, the route of administration, the time of administration, the rate of excretion of the particular compound being employed, the duration of the treatment, other drugs, compounds and/or materials used in combination with the particular inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a potent inhibitor, e.g., having an $EC_{50}$ in the range of 1 mM to sub-nanomolar, will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated effects, will range from about 0.0001 to about 1000 mg per kilogram of body weight per day, though preferably 0.5 to 300 mg per kilogram.

If desired, the effective daily dose of the active inhibitor may be administered as two, three, four, five, six or more sub-doses administered separately at appropriate intervals throughout the day, optionally, in unit dosage forms.

In a preferred embodiment, the inhibitor agent is formulated for oral administration, as for example in the form of a solid tablet, pill, capsule, caplet or the like (collectively hereinafter "tablet") or an aqueous solution or suspension. In a preferred embodiment of the tablet form of the inhibitor agent, the tablets are preferably formulated such that the amount of inhibitor agent (or inhibitor agents) provided in 20 tablets, if taken together, would provide a dose of at least the median effective dose ($ED_{50}$), e.g., the dose at which at least 50% of individuals exhibited a therapeutic affect. For example, for an inhibitor agent, the therapeutic effect would be a quantal effect of inhibition of MHC class II molecule-mediated T cell activation (e.g., a statistically significant reduction in inflammation). More preferably, the tablets are formulated such that the total amount of inhibitor agent (or inhibitor agents) provided in 10, 5, 2 or 1 tablets would provide at least an $ED_{50}$ dose to a patient (human or non-human mammal). In other embodiments, the amount of inhibitor agent (or inhibitor agents) provided in 20, 10, 5 or 2 tablets taken in a 24 hour time period would provide a dosage regimen providing, on average, a mean plasma level of the inhibitor agent(s) of at least the $ED_{50}$ concentration (the concentration for 50% of maximal effect of, e.g., inhibiting an MHC activity), though preferably less than 100 times the $ED_{50}$, and even more preferably less than 10 or 5 times the $ED_{50}$. In preferred embodiments, a single dose of tablets (1-20 tablets) provides about 0.25 mg to 1250 mg of an inhibitor agent(s).

Likewise, the inhibitor agents can be formulated for parenteral administration, as for example, for subcutaneous, intramuscular or intravenous injection, e.g., the inhibitor agent can be provided in a sterile solution or suspension (collectively hereinafter "injectable solution"). The injectable solution is preferably formulated such that the amount of inhibitor agent (or agents) provided in a 200 cc bolus injection would provide a dose of at least the median effective dose, though preferably less than 100 times the $ED_{50}$, and even more preferably less than 10 or 5 times the $ED_{50}$. More preferably, the injectable solution is formulated such that the total amount of inhibitor agent (or agents) provided in 100, 50, 25, 10, 5, 2.5, or 1 cc injections would provide an $ED_{50}$ dose to a patient, and preferably less than 100 times the $ED_{50}$, and even more preferably less than 10 or 5 times the $ED_{50}$. In other embodiments, the amount of inhibitor agent (or inhibitor agents) provided in a total volume of 100 cc, 50, 25, 5 or 2 cc to be injected at least twice in a 24 hour time period would provide a dosage regimen providing, on average, a mean plasma level of the inhibitor agent(s) of at least the $ED_{50}$ concentration, though preferably less than 100 times the $ED_{50}$, and even more preferably less than 10 or 5 times the $ED_{50}$. In preferred embodiments, a single dose injection provides about 0.25 mg to 1250 mg of inhibitor agent.

For continuous intravenous infusion, e.g., drip or push, the inhibitor agent may be provided in a sterile dilute solution or suspension (collectively hereinafter "i.v. injectable solution"). The i.v. injectable solution is preferably formulated such that the amount of inhibitor agent (or inhibitor agents) provided in a 1 L solution would provide a dose, if administered over 15 minutes or less, of at least the median effective dose, though preferably less than 100 times the $ED_{50}$, and even more preferably less than 10 or 5 times the $ED_{50}$. More preferably, the i.v. injectable solution is formulated such that the total amount of inhibitor agent (or inhibitor agents) provided in 1 L solution administered over 60, 90, 120 or 240 minutes would provide an $ED_{50}$ dose to a patient, though preferably less than 100 times the $ED_{50}$, and even more preferably less than 10 or 5 times the $ED_{50}$. In preferred embodiments, a single i.v. "bag" provides about 0.25 mg to 5000 mg of inhibitor agent per liter i.v. solution, more preferably 0.25 mg to 2500 mg, and even more preferably 0.25 mg to 1250 mg.

An $ED_{50}$ dose, for a human, is based on a body weight of from 2 Kg to 125 Kg, though more preferably for an adult in the range of 50 to 125 Kg.

Potential inhibitors may be assessed for $ED_{50}$ values for any inhibition, including for example therapeutic activity towards rheumatoid arthritis or multiple sclerosis, using any of a number of well known techniques in the art, such as those described above.

VI. Combinatorial Synthesis of Subject Inhibitors

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g., a variegated library of compounds represented by formula I or II above, can be screened rapidly in high throughput assays in order to identify potential lead compounds, as well as to refine the specificity, toxicity, and/or cytotoxic-kinetic profile of a lead compound, e.g., by using one of the assays described herein.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject inhibitors. See, for example, Blondelle et al. (1995) *Trends Anal. Chem.* 14:83; the Affymax U.S. Pat. Nos. 5,359,115 and 5,362,899: the Ellman U.S. Pat. No. 5,288, 514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject inhibitors can be synthesized and screened for particular activity or property.

A) Direct Characterization

A growing trend in the field of combinatorial chemistry is to exploit the sensitivity of techniques such as mass spectrometry (MS), for example, which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811-5814; Valerio et al. (1991) *Anal Biochem* 197:168-177; Bray et al. (1991) *Tetrahedron Lett* 32:6163-6166).

C) Divide-Couple-Recombine

In yet another embodiment, a variegated library of compounds can be provided on a set of beads utilizing the strategy of divide-couple-recombine (see, for example, Houghten (1985) *PNAS* 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Spatially Addressable Parallel Chemical Synthesis

A scheme of combinatorial synthesis in which the identity of a compound is given by its locations on a synthesis substrate is termed a spatially addressable synthesis. In one embodiment, the combinatorial process is carried out by controlling the addition of a chemical reagent to specific locations on a solid support. For example, a preferred method for the combinatorial synthesis of compounds of the invention, for example analogues of those shown in Tables 1 and 2, is the SPOT technology described in EP0651762 with improvements and applications described in WO 00/12575, WO 01/18545 and Reinehe et al 2001 (Current Opinions in Biotech 12: 59-64). Another preferred method is provided by the use of microchannels to create combinatorial arrays of candidate or variant compounds, for example as described in WO 99/67024 and WO 99/56878.

Alternatively, combinatorial libraries in a spatially addressable form may be generated by light-directed synthesis (Dower et al. (1991) *Annu Rep Med Chem* 26:271-280; Fodor, S. P. A. (1991) Science 251:767; Pirrung et al. (1992) U.S. Pat. No. 5,143,854; Jacobs et al. (1994) *Trends Biotechnol* 12:19-26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381-5383), and an example of such a library appeared the following year (Needles et al. (1993) PNAS 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr et al. (1993) JACS 115:2529-2531), orthogonality in synthesis is achieved by employing acid-labile protection for the coding strand and base-labile protection for the compound strand.

In an alternative approach (Nikolaiev et al. (1993) Pept Res 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) PNAS 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723-4724). This orthogonal attachment strategy permits the selective detachment of library members for assay in solution and subsequent decoding by ECGC after oxidative detachment of the tag sets.

Although several a mide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: First, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

The peptidomimetic compounds of the present invention may be synthesized using techniques such as those described above to provide a large, highly diverse library of candidate inhibitors, because compounds of the invention can be readily prepared by successively forming a series of carbon-heteroatom bonds, such as amide or urea bonds, under mild conditions. Thus, from a discrete set of subunits, such as amino acids and subunits which incorporate a bicyclic aryl-1,2-diazacyclohexane subunit, a wide range of combinations and permutations of these subunits may be rapidly and easily synthesized and tested for biological activity.

EXEMPLIFICATION

The present invention will now be illustrated by reference to the following examples, which set forth particularly advantageous embodiments. However, it should be noted that these embodiments are illustrative and are not to be construed as restricting the invention in any way.

Example 1

Preparation of Peptidomimetic Compounds

Peptidomimetic compounds were prepared by assembly of building blocks using standard solid phase peptide chemistry (R. B. Merrifield, J. Am. Chem. Soc. 85, 2149-2154 (1963), G. Barany, R. B. Merrifield in The Peptides, Vol. 2 (eds. E. Gross, J. Meienhofer) 1-284 (Academic, New York; 1980)) in a peptide synthesizer (ACT90, Advanced ChemTech) and purified by high performance liquid chromatography (HPLC).

HPLC was conducted on a Vision Chromatograph (PerSeptive Biosystems). Analytical HPLC was performed in reverse phase mode using waters μBondapak $C_{18}$ columns (0.46×25 cm, 5μ or 0.39×30 cm, 10 μ) or Nucleosil $C_{18}$ columns (0.46×25 cm, 5μ or 0.4×30 cm, 10μ) from CS-Chromatographie Service, Langerwehe, Germany. Preparative HPLC was performed in reversed phase mode using Waters μBondapak $C_{18}$ columns (1.9×30 cm, 10μ) or Nucleosil $C_{18}$ columns (2.0×30 cm, 10μ) from CS-Chromatographie Service. Flash chromatography was performed on Merck Kieselgel 60 (0.063-0.200 mm, Art No. 1.07734) obtained from Merck Darmstadt, Germany. T. L. C. was performed on aluminium sheets Silica gel 60 $F_{254}$ (Art No. 1.05554) obtained from Merck Darmstadt, Germany. $^1$H-NMR-Spectra were determined at 200 MHz using tetramethylsilane as internal standard, and are expressed as chemical shift (δ) values in parts per million relative to tetramethylsilane and assigned using s=singlet; m=multiplet; d=doublet; t=triplet; q=quartet, sp=septet, br=broad.

The following abbreviations are used: Boc=tert-butoxycarbonyl, Fmoc=9-fluorenylmethoxycarbonyl, Acm=acetamidomethyl, Prm=propylamidomethyl, DCM=dichloromethane; DMF=N,N-dimethylformamide, DMAP=4-dimethylamino pyridine, HOBt=1-hydroxybenzotriazole; DIC=diisopropylcarbodiimide, TBTU=2-(1-H-benzotriazole-1-yl)-1,1,3,3-tetramethyluronium tetrafluoroborate, THF=tetrahydrofuran, DIPEA=diisopropylethylamine, TFA=trifluoroacetic acid, Me=methyl, Ac=acetyl, tBu=tert-butyl, Bn=benzyl, Ph=phenyl, h=hour(s), min=minute(s), aq.=aqueous, r.t.=room temperature (18-26° C.), Pmc=2,2,5,7,8-pentamethylchromane-6-sulfonyl, PyBOP=benzotriazole-1-yl-oxytris-pyrrolidino-phosphonium hexafluorophosphate, Z=benzyloxycarbonyl, EDCI=1-ethyl-3(3'-dimethylaminopropyl)carbodiimide, DBU=1,8-diazabicyclo[5.4.0]undec-7-ene, Cit=(L) citrullinyl, Cha=(L)-cyclohexylalaninyl, Gpg=(L)-N-amidino-4-piperidinylglycinyl, βPhPro=2-(S)-3-(R)-3-phenylprolinyl, Tic=(L)-tetrahydroisoquinoline-3-carbonyl, azaTic=3,4-dihydro-1H-phthalazine-2-carbonyl, Disc=(D,L) 1,2-dihydro-2H-isoindole carbonyl, Thiq=(L)-tetrahydroisoquinoline-1-carbonyl, Hbc (D,L)-2,3,4,5-tetrahydro-1H-benzo[d]azepine-2-carbonyl, Haic=(2S, 5S)-5-amino-1,2,3,4,5,6,7-hexahydro-azepino [3,2,1-h,i] indole-4-one-2-carbonyl, Odapdc=(1S, 9S)-9-aminooctahydro-6,10-dioxo-6H-pyridazino-[1,2-a][1,2]diazepine-1-carbonyl, [SΨ(oxaz)L]=oxazole mimetic of S-L, [SΨ(imid)L]=imidazole mimetic of S-L, A=Ala=(L)-alaninyl, R=Arg=(L)-argininyl, C=Cys=(L)-cysteinyl, F=Phe=(L)-phenylalaninyl, V=Val=(L)-valinyl, Met=(L)-methioninyl, Nle=(L)-norleucinyl, S=Ser=(L)-serinyl, L=Leu=(L)-leucinyl, alle=(L)-alloisoleucinyl, Nva=(L)-norvalinyl, Pya=(L)-pyridylalaninyl, Orn=(L)-omithinyl, Chg=(L)-cyclohexylglycinyl, Hfe=(L)-homophenylalaninyl, Thi=(L)-2-thienylalaninyl, Coa=(L)-cyclooctylalaninyl, Nba=(L)-norbornylalaninyl, N-(2-phenylethyl)ethanolamine was prepared from 2-phenylethyl chloride and ethanolamine according to literature procedure (J. Barbiere, Bull. Soc. Chim. Fr. 5, 7, 1940, 621). Commercially available Fmoc amino acids, HOBt, TBTU and PyBOP were purchased from Advanced ChemTech, Novabiochem, Bachem, Neosystems or RSP Amino Acid Analogues. All other chemicals and solvents were purchased from Merck Darmstadt or Sigma-Aldrich-Fluka and used without further purification. DMF was dried over molecular sieves 4 Å for at least 4 weeks, stirred over acidic aluminium oxide for 20 minutes to remove traces of amines, and filtered through a 0.2 μm filter prior use.

Table 1 (a, b and c) lists certain compounds according to Formulae I and II that are exemplary of the invention. Table 2 lists other compounds examined for their immunomodulatory and other properties using the assays described herein. As will be apparent to a person skilled in the art after reading this disclosure, peptidomimetics shorter than the heptamers set forth in Table 1 are useful for certain applications. As such, shorter peptidomimetics also form part of this invention. Preferred lengths of these shorter peptides are tetra- or pentamers.

Example 2

Preparation of Ac-Cha-Gpg-Tic-Nle-βPhPro-[SΨ(oxaz)L]NMe$_2$ (P53)

2.1 Preparation of Fmoc-βPhPro-OH

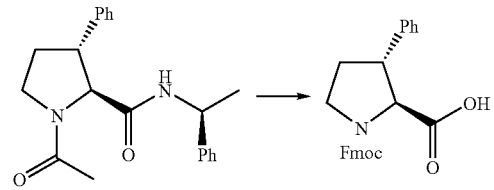

44.61 g N-Acetyl-trans-3(R)-phenyl-(S)-proline-1-(S)-phenylethyl amide (J. Y. L. Chung, J. T. Wasicak, W. A.

Arnold, C. S. May, A. N. Nadzan, M. W. Holladay, J. Org. Chem. 1990, 55, 270-275) was dissolved in 730 ml 8 N HCl and 360 ml acetic acid. The resulting solution was heated to 140° C. for 16 h. After cooling to r.t. the solution was evaporated to dryness. The residue was taken up in 1000 ml of water. The aq. solution was washed with ethyl acetate (3×200 ml) and concentrated under reduced pressure to a final volume of 300 ml. 400 ml aq. 10% $Na_2CO_3$-solution were added and the aq. layer was washed with ethyl acetate (4×200 ml). 200 ml aq. 10% $Na_2CO_3$-solution were added and the solution was cooled to 0° C. A solution of 51.22 g FmocCl in 300 ml dioxane was added dropwise over 1.5 h and the resulting suspension was stirred at r.t. for 18 h. The precipitate was removed by decantation. The aq. solution was washed with diethyl ether (1×200 ml) acidified with 1 N HCl to pH 3 and extracted with D CM (2×300 ml). The precipitate was dissolved in ethyl acetate. The resulting solution was extracted with saturated aq. $NaHCO_3$ solution. The aq. layer was acidified with conc. HCl to pH 3 and extracted with DCM. The combined DCM layers were dried over $Na_2SO_4$, filtered and evaporated to dryness. The residue was preabsorbed onto silica and purified by flash chromatography using ethyl acetate/hexane/acetic acid 150:50:1 as eluent. The fractions containing the desired product (checked by T. L. C.) were combined and evaporated. The resulting residue was recrystallized from $CHCl_3$/hexane 1:2 to give a total yield of 24.92 g (55%).

$^1$H-NMR ($CDCl_3$): 1.95-2.15 (m, 1H, FmocNCH$_2$CH$\underline{H}$, 2.24-2.47 (m, 1H, FmocNCH$_2$C$\underline{H}$H), 3.43-3.85 (m, 3H), 4.06-4.58 (m, 4H), 6.2 (br s, 1H, COOH) 7.11-7.82 (m, 13H, arom. Hs).

2.2 Preparation of H[S(OtBu)Ψ(oxaz)L]NMe$_2$ 2.2.1 Preparation of Dipeptide I:

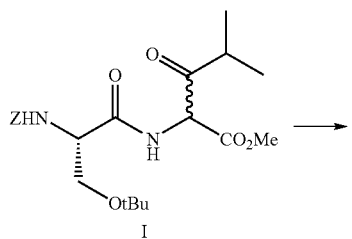

10.0 g Methyl N-(diphenylmethylen)glycinate (M. J. O'Donnell, R. L. Polt, J. Org. Chem. 1982, 47, 2663-2666) were added to a solution of 4.87 g KOtBu in 100 ml dry THF at −5° C. and the resulting solution was stirred at 0° C. for 15 min. This solution was added over 3.5 h to a solution of 7.1 ml isobutyric acid chloride in 300 ml dry THF at −78° C. After addition was completed the orange reaction mixture was allowed to reach r.t. The resulting yellow solution was treated with 200 ml 1 N HCl and the mixture was stirred at r.t. for 15 min. The organic solvent was evaporated under reduced pressure. The aq. layer was washed with ethyl acetate (4×100 ml) and evaporated to dryness to give 10.2 g residue.

11.66 g Z-Ser(tBu)OH was dissolved in 200 ml dry THF under an atmosphere of Ar and the solution was cooled to −18° C. 5.48 ml Triethylamine were added followed by 5.2 ml isobutyl chloroformate. The suspension was stirred at −18° C. for 15 min. The above residue was added and a solution of 5.48 ml triethylamine in 80 ml dry THF was added dropwise over 1 h. After addition was completed the suspension was stirred at −18° C. for additional 1.5 h and then allowed to reach r.t. Saturated aq. NaCl solution (200 ml) was added and the mixture was stirred for 15 min. The aq. layer was separated and extracted with diethyl ether (3×100 ml). The combined organic layers were washed with pH 7 phosphate buffer (1×50 ml), dried over $Na_2SO_4$, filtered and evaporated to dryness. The residue was purified by flash chromatography using ethyl acetate/hexane (1:3-1:2) as eluent to give 14.4 g (84%) of the desired compound as a mixture of diastereomers. $^1$H-NMR ($CDCl_3$): 1.09-1.28 (m 15H, CHM̈ë$_2$, tBu), 3.05 (sp, 1H, C$\underline{H}$Me$_2$), 3.38-3.45 (m, 1H, C$\underline{H}$HOtBu), 3.78, 3.79 (2 s, 3 H, OMe), 3.75-3.88 (br s, 1 H, CH$\underline{H}$OtBu), 5.05-5.18 (m, 2 H, C$\underline{H}_2$Ph), 5.38 (d, J=6.8 Hz, 1H, COCHCO), 5.70 (br s, 1H, carbamate-NH), 7.25-7.42 (m, 5H, Ph), 7.95 (br s, 1 H, amide-NH).

2.2.2 Preparation of Z[S(OtBu)Ψ(oxaz)L]OMe

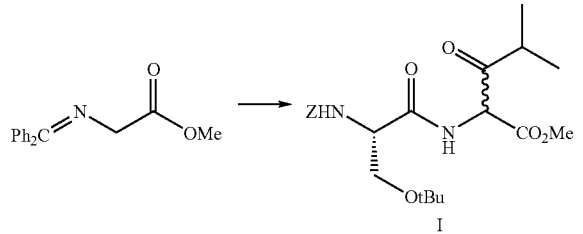

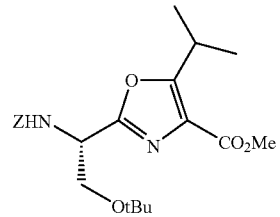

55.0 g Triphenylphosphineoxide and 31.3 ml DBU were added to a solution of 30.5 g of the dipeptide I in 38 ml dry carbontetrachloride, 38 ml dry acetonitrile and 38 ml dry pyridine at 0° C. The resulting mixture was stirred at r.t. for 20 h. The solvents were removed under reduced pressure and the residue was coevaporated with toluene (4×150 ml). The resulting residue was dissolved in 900 ml DCM. The solution was washed with aq. 5% $KHSO_4$-solution (5×200 ml) and pH 7 phosphate buffer (2×150 ml), dried over $Na_2SO_4$, filtered and evaporated to dryness. The residue was taken up in 450 ml ethyl acetate and the suspension was sonicated and filtered. The filtrate was concentrated to a final volume of 100 ml. 300 ml hexane were added and the resulting suspension was again sonicated and filtered. The filtrate was evaporated to dryness and the residue was purified by flash chromatography using ethyl acetate/hexane (1:3) as eluent to give 24.7 g (85%) of the title compound as a slightly yellow oil. $^1$H-NMR ($CDCl_3$): 1.07 (s, 9H, tBu), 1.23-1.28 (m, 6 H, CHM$\underline{e}_2$), 3.64 (dd, J3=, 1 H, 4.0, 9.2 Hz, 1H, C$\underline{H}$HOtBu), 3.68-3.85 (m, 2 H, C$\underline{H}$Me$_2$, CH$\underline{H}$OtBu), 3.90 (s, 3 H, OMe), 5.00-5.11 (br m, 1 H, C $\underline{H}$NHCO), 5.13 (s, 2 H, CH$_2$Ph), 5.79 (br d, J=7.4 Hz, 1 H, NH), 7.25-7.41 (m, 5H, Ph).

2.2.3 Preparation of Z[S(OtBu)Ψ(oxaz)L]NMe₂

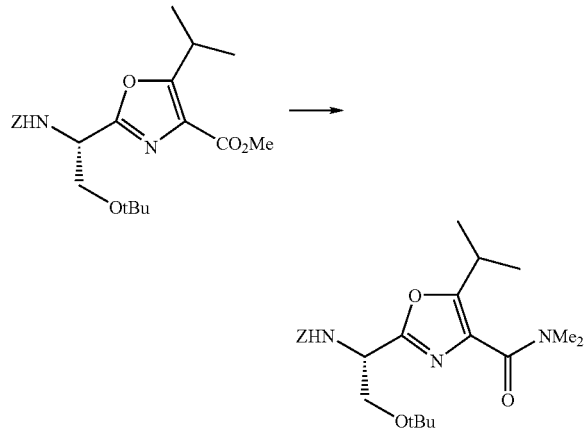

24.71 g Z[S(OtBu)Ψ(oxaz)L]OMe was dissolved in 200 ml methanol and the solution was cooled to 0° C. A solution of 1.84 g LiOH in 80 ml water was added dropwise over 35 min. The mixture was stirred at 0° C. for 1.5 h and at r.t. for 16 h. The solution was neutralized with 1 N HCl and methanol was evaporated under reduced pressure. The resulting aq. solution was acidified to pH 4 with 1 N HCl and extracted with DCM (4×100 ml). The combined organic layers were dried over Na₂SO₄, filtered and evaporated. The residue was dissolved in 250 ml dry DMF and the solution was cooled to 0° C. After addition of 11.3 g HOBt, 14.1 g EDCI, 7.6 ml triethylamine, 13.8 g dimethylamine hydrochloride and another 15.7 ml triethylamine the mixture was stirred for 17 h at r.t. The solution was evaporated under reduced pressure and the resulting residue was coevaporated with toluene (1×100 ml). The residue was taken up in 400 ml ethyl acetate, the resulting suspension was filtered and the filtrate was washed with aq. 5% KHSO₄ solution (3×100 ml), aq. saturated NaHCO₃ solution (2×100 ml) and pH 7 phosphate buffer (2×100 ml). The organic layer was dried over Na₂SO₄, filtered and evaporated. The residue was purified by flash chromatography using ethyl acetate/hexane (2:3) as eluent to give 23.3 g (92%) of the title compound as an oil. ¹H-NMR (CDCl₃): 1.07 (s, 9 H, tBu), 1.22-1.26 (m, 6 H, CH$\underline{Me}$₂), 3.03, 3.18 (2 s, 2×3H, NMe₂), 3.51 (sp, J3=7.0 Hz, 1H, C$\underline{H}$Me₂), 3.65 (dd, J=4.0, 8.8 Hz, 1 H, C$\underline{H}$HOtBu), 3.78 (br m, 1 H. CH$\underline{H}$OtBu), 4.98-5.09 (br m, 1 H, C$\underline{H}$NHCO), 5.10-5.21 (m, 2 H, C$\underline{H}$₂Ph), 5.70 (br d, J=7.3 Hz, 1 H, NH), 7.21-7.45 (m, 5 H, Ph).

2.2.4 Preparation of H[S(OtBu)Ψ(oxaz)L]NMe₂

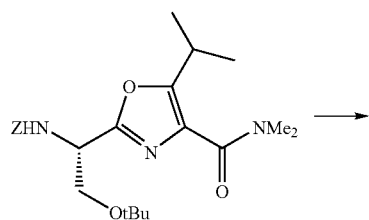

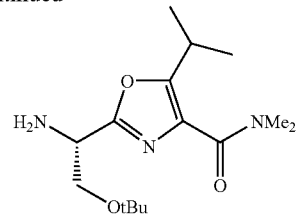

A solution of 23.3 g Z[S(OtBu)Ψ(oxaz)L]NMe₂ in 100 ml ethanol was added to a suspension of 2.35 g Pd/C (10%) under an atmosphere of hydrogen and the mixture was stirred at r.t. for 18 h. The suspension was filtered through Celite and the filtrate was evaporated to dryness to give 14.5 g (90%) of the title compound. ¹H-NMR (CDCl₃): 1.15 (s, 9 H, tBu), 1.27 (d, J=7.0 Hz, 6 H, CH$\underline{Me}$₂), 2.04 (s, 2H, NH₂), 3.04, 3.23 (2 s, 2×3 H, NMe₂), 3.50 (sp, J=7.0 Hz, 1 H, C$\underline{H}$Me₂), 3.60 (dd, J=6.5, 8.8 Hz, 1 H, C$\underline{H}$HOtBu), 3.69 (dd, J=4.4, 8.8 Hz, 1H, CH$\underline{H}$OtBu), 4.14 (dd, J=4.4, 6.5 Hz, 1 H, C$\underline{H}$NH₂).

2.3 Preparation of HβPhPro-2-chlorotrityl Resin

A solution of 7.4 g Fmoc-βPhPro-OH in 120 ml dry DCM was added to 12.0 g 2-chlorotrityl chloride resin (0.83 mmol/g, Novabiochem). DIPEA (3.0 ml) was added and the mixture was shaken for 10 min. Additional 4.5 ml DIPEA were added and shaking was continued for 145 min. Methanol (10 ml) was added the mixture was shaken for another 25 min. The resin was filtered off, washed with DCM (5×100 ml), methanol (2×100 ml) and DCM (4×100 ml). A small sample was dried carefully and deprotected with DCM/piperidine (1:1) for 30 min. Photometric determination of the resulting Fmoc-piperidine adduct (absorption at 301 nm) gave a resin loading of 0.54 mmol/g. The remaining resin was treated with 100 ml DCM and 80 ml piperidine at r.t. for 160 min, washed with DCM (10×100 ml) and diethyl ether (4×80 ml) and dried in vacuo to give 14.37 g HβPhPro-2-chlorotrityl resin.

2.4. Preparation of Ac-Cha-Gpg-Tic-Nle-βPhPro-[SΨ(oxaz)L]NMe₂ (P53)

The peptididomimetic was prepared by Fmoc solid phase synthesis starting with HβPhPro-2-chlorotrityl chloride resin (2416 mg, 1.3 mmol) in a 50 ml reaction vessel fitted with a frit in the bottom (Advanced ChemTech ACT90).

Resin swelling was carried out by treating the resin with DMF (4×1 min.). The resin was deprotected using a 20% solution of piperidine in DMF (1×3 min, 1×7 min, 20 ml each) and subsequently washed with DMF (10×20 ml). Acylation was carried out by addition of FmocNleOH (1380 mg, 3.9 mmol), DMF (8.2 ml), HOBt (600 mg, 3.9 mmol), and DIC (0.61 ml, 3.9 mmol). The coupling was left for 18 h, washed with DMF (7×20 ml). A small portion was checked for completion of acylation using the Chloranil test (J. Blake, C. H. Li, Int. J. Peptide Protein Res., 1975, 7, 495). The resin was capped using a solution of acetic anhydride (2 M) and DMAP (0.1 M) in DMF (20 ml, 1×10 min) and subsequently washed with DMF (12×20 ml). The resin was deprotected, washed, capped and washed as above and coupled with FmocTicOH (1.56 g, 3.9 mmol), TBTU (1.26 g, 3.9 mmol) and DIPEA (0.71 ml, 4.16 mmol) in 8 ml DMF for 75 min.

The resin was deprotected, washed, capped and washed as above and coupled with FmocGpg(Pmc)OH (1.35 g, 1.95 mmol), HOBt (0.3 g, 1.95 mmol) and DIC (0.305 ml, 1.95 mmol) in 7 ml DMF for 16 h.

The resin was deprotected, washed, capped and washed as above and coupled with FmocChaOH (1.54 g, 3.9 mmol), HOBt (0.6 g, 3.9 mmol) and DIC (0.61 ml, 3.9 mmol) in 8 ml DMF for 3 h.

Deprotection and washing was carried out as above and capping was performed by treatment with acetic anhydride (2 M) and DMAP (0.1 M) in 20 ml DMF for 3×20 min. The resin was washed with DMF (12×20 ml), MeOH (3×50 ml), Et$_2$O (3×40 ml) and dried in vacuo.

The resin was treated with 33 ml DCM/trifluoroethanol/acetic acid (8:1:1) at r.t. for 45 min, filtered and washed with 65 ml DCM/trifluoroethanol/acetic acid (8:1:1) and 100 ml DCM. 250 ml n-Hexane were added to the filtrate, the resulting suspension was evaporated to dryness and the residue was coevaporated with n-hexane (3×100 ml) to give 1.188 g of crude Ac-Cha-Gpg(Pmc)-Tic-Nle-βPhPro-OH. The residue was dissolved in 5 ml dry DMF and cooled to 0° C. After addition of 332 mg HOBt, 642 mg H[S(OtBu)Ψ(oxaz)L]NMe$_2$ and 415 mg EDCI, the solution was stirred for 1.5 h at 0° C. and another 16 h at r.t. The solvent was removed under reduced pressure and the residue was dissolved in 80 ml ethyl acetate. The solution was washed with aq. 5% KHSO$_4$ solution (1×40 ml), saturated aq. NaHCO$_3$ solution and pH 7 phosphate buffer, dried over Na$_2$SO$_4$, filtered and evaporated to dryness. The residue was treated with 20 ml of TFA/water/thioanisole/1,2-ethanedithiol/triethylsilane 85.5:5:5:2.5:2 for 3.7 h at r.t. The product was precipitated by adding 550 ml of chilled diethyl ether to the solution. The suspension was centrifuged at 3300 rpm for 10 min, the supernatant was discarded, the precipitate was resuspended in chilled ether, centrifuged again and the supernatant was once again discarded. The precipitate was dissolved in acetonitrile and 0.1% aq TFA. The organic solvents were evaporated under reduced pressure and the aq. solution was freeze dried. The crude product (931 mg) was purified by HPLC using a gradient of acetonitrile in 0.1% aq TFA to yield 584 mg pure Ac-Cha-Gpg-Tic-Nle-βPhPro-[SΨ(oxaz)L]NMe$_2$×TFA. The product was characterized by mass spectrometry, MALDI-TOF MS: M/Z=1064.57, (MH+), 1102.53 (MK+).

Example 3

Preparation of Ac-Cha-Arg-Tic-Nle-βPhPro-[SΨ(oxaz)L]NMe$_2$ (P51)

This peptiodomimetic was prepared using similar methodology to that described for Example 2.4 but on a smaller scale using less resin, a 25 ml reaction vessel and 7 ml solvent portions for swelling, washing, capping, deprotection and coupling during solid phase synthesis. Coupling on βPhPro was performed using FmocNleOH, HOBt, DIC (3 equivalents each) for 16 h, coupling on Nle was done using FmocTicOH (3eq), TBTU (3 eq) and DIPEA (3.2 eq) for 1.5 h, coupling on Tic was done using FmocArg(Pmc)OH, HOBt, DIC (3 eq each) for 16 h, coupling on Arg was done using FmocChaOH, HOBt, DIC (3 eq each) for 3 h. The solution coupling was carried out using H[S(OtBu)Ψ(oxaz)L]NMe$_2$ (2 eq), PyBOP (2 eq) and 4-methylmorpholine (4 eq) in DMF at 0° C. for 1 h and at r.t. for 16 h. The resulting mixture was evaporated to dryness and the residue was treated with TFA/water/thioanisole/1,2-ethanedithiol/triethylsilane 85.5:5:5:2.5:2 for 3.5 h at r.t. The product was precipitated by adding 200 ml of chilled diethyl ether. The suspension was kept at 0° C. for 1 h and than treated as described in example 2.4. The crude product was purified by HPLC using a gradient of acetonitrile in 0.1% aq TFA. MALDI-TOF MS: M/Z=1038.70 (MH+), 1060.36 (MNa+), 1076.61 (MK+).

Example 4

Preparation of Ac-Cha-Arg-Tic-Met-βPhPro-[SΨ(oxaz)L]NMe$_2$ (P33) & Ac-Cha-Gpg-Tic-Met-βPhPro-[SΨ(oxaz)L]NMe$_2$ (P60)

Peptiodomimetic P33 (Arg) was prepared as described in Example 3, except that the resin was coupled in coupling step 1 with FmocMetOH instead of FmocNleOH. MALDI-TOF MS: M/Z=1057.00 (MH+), 1079.01 (MNa+), 1094.98 (MK+).

Peptiodomimetic P60 (Gpg) was prepared as described in Example 3, except that the resin was coupled in coupling step 1 with FmocMetOH instead of FmocNleOH, and in coupling step 3 with FmocGpg(Pmc)OH, HOBt, DIC (1.5 eq each) instead of FmocArg(Pmc)OH, HOBt and DIC (3 eq each). MALDI-TOF MS: M/Z=1082.54 (MH+), 1120.51 (MK+).

Example 5

Preparation of Ac-Cha-Arg-Tic-Met(O)-βPhPro-[SΨ(oxaz)L]NMe$_2$ (P43) & Ac-Cha-Gpg-Tic-Met(O)-βPhPro-[SΨ(oxaz)L]NMe$_2$ (P47)

Peptiodomimetic P43 (Arg) was prepared as described in Example 3, except that the resin was coupled in coupling step 1 with FmocMet(O)OH instead of FmocNleOH. MALDI-TOF MS: M/Z=1072.57 (MH+).

Peptiodomimetic P47 (Gpg) was prepared as described in Example 3, except that the resin was coupled in coupling step 1 with FmocMet(O)OH instead of FmocNleOH, and in coupling step 3 with FmocGpg(Pmc)OH, HOBt, DIC (1.5 eq each) instead of FmocArg(Pmc)OH, HOBt, DIC (3 eq each). MALDI-TOF MS: M(Z=1098.73 (MH+), 1120.70 (MNa+), 1136.68 (MK+).

Example 6

Preparation of Ac-Cha-Arg-Disc-Met-βPhPro-[SΨ(oxaz)L]NMe$_2$ (P40) & Ac-Cha-Gpg-Disc-Met-βPhPro-[SΨ(oxaz)L]NMe$_2$ (P41)

Peptiodomimetic P40 (Arg) was made as P33 in Example 4 except for that the resin was coupled in coupling step 2 with racemic FmocDiscOH instead of FmocTicOH. The resulting two diastereomers were separated at the final HPLC step using a gradient of acetonitrile in 0.1% aq TFA. Each stereoisomer was isolated and denoted as either the "fast" fraction (suffixed-1 in the compound names) or the "slow" fraction (suffixed-2 in the compound names), and tested separately in the subsequent biological assays. MALDI-TOF MS (P40-1): M/Z=1042.67 (MH+), 1058.66 (MNa+), 1080.63 (MK+). MALDI-TOF MS (P40-2): M/Z=1042.69 (MH+), 1058.66 (MNa+), 1080.62 (MK+).

Peptiodomimetic P41 (Gpg) was prepared as P60 in Example 4 except for that the resin was coupled in coupling step 2 with racemic FmocDiscOH instead of FmocTicOH. The resulting two diastereomers were separated at the final HPLC step using a gradient of acetonitrile in 0.1% aq TFA. Each stereoisomer was isolated and denoted as either the "fast" fraction (suffixed-1 in the compound names) or the "slow" fraction (suffixed-2 in the compound names), and tested separately in the subsequent biological assays.

MALDI-TaOF MS (P41-1): M/Z=1068.43 (MH+), 1106.38 (MK+). MALDI-TOF MS (P41-2): M/Z=1068.42 (MH+), 1106.36 (MK+).

Example 7

Preparation of Ac-Cha-Gpg-Tic-Nle-NHCH$_2$CH$_2$Ph (P69) & Ac-Cha-Arg-Tic-Nle-NHCH$_2$CH$_2$Ph (P82)

7.1 Preparation of HNle-2-chlorotrityl Resin

The resin was prepared using similar methodology to that described in Example 2 step 2.3 from FmocNleOH (4.37 g) and 2-chlorotrityl chloride resin (7.45 g, 0.83 mmol/g, Novabiochem) to yield 7.77 g HNle-2-chlorotrityl resin (loading: 0.50 mmol/g).

7.2 Preparation of Ac-Cha-Gpg(Pmc)-Tic-Nle-OH

The peptidomimetics were prepared using similar methodology to that described for Example 1.4 by deprotection and coupling using HNle-2-chlorotrityl resin (2.52 g). Coupling on Nle was performed using TBTU (1.09 g, 1.35 mmol), DIPEA (0.62 ml, 1.44 mmol) and FmocTicOH (1.36 g, 1.35 mmol) in 7 ml DMF with a coupling time of 2.5 h. Coupling on Tic was carried out using FmocGpg(Pmc)OH (1.17 g, 0.68 mmol), HOBt (0.26 g, 0.68 mmol) and DIC (0.27 ml, 0.68 mmol) in 6 ml DMF over 17 h and coupling on Gpg was done with FmocChaOH (1.34 g, 1.35 mmol), HOBt (0.52 g, 1.35 mmol) and DIC (0.53 ml, 1.35 mmol) in 6 ml DMF over 2.5 h. Completion of coupling was checked by Kaiser test or Chloroanil test, respectively (E. Kaiser, et al. (1970) Anal. Biochem. 34, 595; J. Blake, C. H. Li, Int. J. Peptide Protein Res., 1975, 7, 495). After final acetylation, resin cleavage and evaporation (analog to example 1.4) 1.59 g crude Ac-Cha-Gpg(Pmc)-Tic-Nle-OH was isolated.

7.3 Preparation of Ac-Cha-Gpg-Tic-Nle-NHCH$_2$CH$_2$Ph (P69)

A solution of Ac-Cha-Gpg(Pmc)-Tic-Nle-OH (730 mg, 0.78 mmol) in 5 ml dry DMF was treated with HOBt (239 mg, 1.56 mmol), PyBOP (812 mg, 1.56 mmol) and 2-Phenylethylamine (0.45 ml, 3.65 mmol) at 0° C. The reaction was stirred at 0° C. for 1.5 h and at r.t. for 13 h. The solvent was evaporated under reduced pressure and the residue was treated with 10 ml of TFA/water/thioanisole/1,2-ethanedithiol/triethylsilane 85.5:5:5:2.5:2 for 4 h at r.t. The product was precipitated by adding 500 ml of chilled diethyl ether to the solution. The suspension was centrifuged at 3300 rpm for 10 min, the supernatant was discarded, the precipitate was resuspended in chilled ether, centrifuged again and the supernatant was once again discarded. The precipitate was dissolved in acetonitrile and 0.1% aq TFA. The organic solvents were evaporated under reduced pressure and the aq. solution was freeze dried. The crude product (767 mg) was purified by HPLC using a gradient of acetonitrile in 0.1% aq. TFA to yield 256 mg pure Ac-Cha-Gpg-Tic-Nle-NHCH$_2$CH$_2$Ph. The product was characterized by mass spectrometry, MALDI-TOF MS: M/Z=771.310, (MH+), 793.286 (MNa+), 809.257 (MK+).

Peptiodomimetic P82 was prepared using similar methodology to that described for Example 3 but using HNle-2-chlorotrityl resin (Example 7.1) instead of HβPhPro-2-chlorotrityl chloride resin. Coupling on Nle was done using FmocTicOH (3 eq), TBTU (3 eq) and DIPEA (3.2 eq) for 1.5 h, coupling on Tic was done using FmocArg(Pmc)OH, HOBt, DIC (3 eq each) for 14 h, coupling on Arg was done using FmocChaOH, HOBt, DIC (3 eq each) for 3 h. The solution coupling was carried out using N-(2-Phenylethyl)amine (4 eq), HOBt (2 eq) and PyBOP (2 eq) in DMF at 0° C. for 1 h and at r.t. for 15 h. The resulting mixture was treated as described in Example 3. The crude product was purified by HPLC using a gradient of acetonitrile in 0.1% aq TFA. MALDI-TOF MS: M/Z=745.61 (MH+), 767.56 (MNa+).

Example 8

Preparation of Ac-Cha-Arg-Tic-Nle-N(Me)Bn (P71) & Ac-Cha-Gpg-Tic-Nle-N(Me)Bin (P74)

Peptiodomimetic P71 (Gpg) was prepared as P82 in Example 7 except for that crude Ac-Cha-Arg(Pmc)-Tic-Nle-OH was reacted with N-methylbenzylamine (4 eq) instead of N-(2-phenylethyl)amine. HPLC using a gradient of acetonitrile in 0.1% aq TFA yielded the desired product. MALDI-TOF MS: M/Z=745.56 (MH+), 783.49 (MK+).

Peptiodomimetic P74 (Gpg) was prepared as P69 in Example 7 except for that crude Ac-Cha-Gpg(Pmc)-Tic-Nle-OH was reacted with N-methylbenzylamine (4 eq) instead of 2-phenylethylamine. HPLC using a gradient of acetonitrile in 0.1% aq TFA yielded the desired product. MALDI-TOF MS (P41-1): M/Z=771.63 (MH+), 793.63 (MNa+).

Example 9

Preparation of Ac-Cha-Arg-Disc-Nle-N(Me)Bn (P72) & Ac-Cha-Gpg-Disc-Nle-N(Me)Bn (P76)

Peptiodomimetic P72 was prepared using similar methodology to that described for P71 in Example 8, except for using racemic FmocDiscOH instead of FmocTicOH in coupling step 1. The resulting two diastereomers were separated at the final HPLC step using a gradient of acetonitrile in 0.1% aq TFA and denoted as described in Example 6. MALDI-TOF MS (P72-1): M/Z=731.57 (MH+), 753.55 (MNa+), 769.52 (MK+). MALDI-TOF MS (P72-2): M/Z=731.56 (MH+), 753.55 (MNa+), 769.52 (MK+).

Peptiodomimetic P76 was prepared using similar methodology to that described for P72 in Example 9, except for using FmocGpg(Pmc)OH, HOBt, DIC (1.5 eq each) instead of FmocArg(Pmc)OH, HOBt, DIC (3 eq each) in coupling step 2. The resulting two diastereomers were separated at the final HPLC step using a gradient of acetonitrile in 0.1% aq TFA and denoted as described in Example 6.1. MALDI-TOF MS (P76-1): M/Z=757.31 (MH+), 779.27 (MNa+), 795.24 (MK+). MALDI-TOF MS (P76-2): M/Z=757.37 (MH+), 779.34 (MNa+), 795.31 (MK+).

Example 10

Preparation of Ac-Cha-Arg-Tic-Met-NH$_2$ (P1) & Ac-Cha-Gpg-Tic-Met-NA$_2$ (P67)

10.1 Preparation of FmocMet-Rinkamide Resin:

FmocMet-Rinkamide resin was prepared by Fmoc solid phase synthesis starting with 3.65 g Fmoc-Rinkamide resin (0.59 mmol/g, Novabiochem) in a 50 ml reaction vessel fitted with a frit in the bottom (Advanced ChemTech ACT90).

Resin swelling was carried out by treating the resin with DMF (4×1 min.).

The resin was deprotected using a 20% solution of piperidine in DMF (1×3 min, 1×7 min, 20 ml each) and subsequently washed with DMF (1×20 ml). Acylation was carried out by addition of FmocMetOH (2.4 g, 3 eq), DMF (10 ml), HOBt (990 mg, 3 eq), and DIC (1.01 ml, 3 eq) and DMAP (260 mg, 0.1 eq). The coupling was left for 4 h and the resin was washed with DMF (7×20 ml). A small sample was dried carefully and deprotected with DCM/piperidine (1:1) for 30 min. Photometric determination of the resulting Fmoc-piperidine adduct (absorption at 301 nm) gave a resin loading of 0.43 m mol/g. The remaining resin was capped using a solution of acetic anhydride (2 M) and DMAP (0.1 M) in DMF (20 ml, 1×10 min) and subsequently washed with DMF (12×20 ml), methanol (3×40 ml) and diethyl ether (3×40 ml), and dried in vacuo to yield 3.9 g FmocMet-Rinkamide resin.

10.2 Preparation of Ac-Cha-Arg-Tic-Met-NH$_2$ (P1) & Ac-Cha-Gpg-Tic-Met-NH$_2$ (P67)

Peptidomimetic P1 was prepared using Fmoc solid phase synthesis starting with FmocMet-Rinkamide resin using the same protocol as described for P51 in Example 3, but starting with a deprotection step. Coupling on Met was performed using FmocTicOH (3 eq), TBTU (3 eq) and DIPEA (3.2 eq) for 1.5 h, coupling on Tic was done using FmocArg(Pmc)OH, HOBt, DIC (3 eq each) for 16 h, coupling on Arg was done using FmocChaOH, HOBt, DIC (3 eq each) for 3 h. After the final acetylation of Cha the resin was washed with DMF (12×7 ml), MeOH (3×20 ml), Et$_2$O (3×20 ml), dried in vacuo and treated with TFA/water/thioanisole/1,2-ethanedithiol/triethylsilane 85.5:5:5:2.5:2 for 3.5 h at r.t. The resin was filtered off, washed with TFA and the product was precipitated from the filtrate by adding 200 ml of chilled diethyl ether. The suspension was kept at 0° C. for 1 h and than treated as described in example 2.4. The crude product was purified by HPLC using a gradient of acetonitrile in 0.1% aq TFA. MALDI-TOF MS: M/Z=659 (MH+), 681 (MNa+), 697 (MK+).

Peptidomimetic P67 was prepared as P1 in Example 10 except for that the resin was coupled in coupling step 2 with FmocGpg(Pmc)OH, HOBt, DIC (1.5 eq each) instead of FmocArg(Pmc)OH, HOBt, DIC (3 eq each). MALDI-TOF MS: M/Z=685.29 (MH+), 707.23 (MNa+), 723.23 (MK+).

Example 11

Preparation of Ac-Cha-Arg-Disc-Met-NH$_2$ (P12) & Ac-Cha-Gpg-Disc-Met-NH$_2$ (P66)

Peptiodomimetic P12 was prepared as described for P1 in Example 10, except for using racemic FmocDiscOH instead of FmocTicOH in coupling step 1. The resulting two diastereomers were separated at the final HPLC step using a gradient of acetonitrile in 0.1% aq TFA and denoted as described in Example 6. MALDI-TOF MS (P12-1): M/Z=645 (MH+), 667 (MNa+). MALDI-TOF MS (P12-2): M/Z=645 (MH+), 667 (MNa+).

Peptiodomimetic P66 was prepared as described for P1 in Example 10, except for using racemic FmocDiscOH instead of FmocTicOH in coupling step 1 and using FmocGpg(Pmc)OH, HOBt, DIC (1.5 eq each) instead of FmocArg(Pmc)OH, HOBt, DIC (3 eq each) in coupling step 2. The resulting two diastereomers were separated at the final HPLC step using a gradient of acetonitrile in 0.1% aq TFA and denoted as described in Example 6. MALDI-TOF MS (P66-1): M/Z=671.25 (MH+). MALDI-TOF MS (P66-2): M/Z=671.29 (MH+).

Example 12

Preparation of Ac-Cha-Arg-Tic-Met-βPhPro-NH$_2$ (P31) & Ac-Cha-Gpg-Tic-Met-βPhPro-NH$_2$ (P80)

12.1 Preparation of Fmoc-βPhPro-Rinkamide Resin

FmocβPhPro-Rinkamide resin was prepared by Fmoc solid phase synthesis as described for FmocMet-Rinkamide resin in Example 10.1 except for using FmocβPhProOH instead of FmocMetOH in coupling step 1.

12.2. Preparation of Ac-Cha-Arg-Tic-Met-βPhPro-NH$_2$ (P31) & Ac-Cha-Gpg-Tic-Met-βPhProNH$_2$ (P80)

Peptidomimetic P31 was prepared using Fmoc solid phase synthesis starting with Fmoc-βPhPro-Rinkamide resin using the same protocol as described for P51 in Example 3, but starting with a deprotection step. Coupling on βPhPro was done using FmocMetOH, HOBt, DIC (3 eq each) for 14 h, coupling on Met was performed using FmocTicOH (3 eq), TBTU (3 eq) and DIPEA (3.2 eq) for 1.5 h, coupling on Tic was done using FmocArg(Pmc)OH, HOBt, DIC (3 eq each) for 16 h, coupling on Arg was done using FmocChaOH, HOBt, DIC (3 eq each) for 3 h. After the final acetylation of Cha the resin was treated as described in Example 10.2. The crude product was purified by HPLC using a gradient of acetonitrile in 0.1% aq TFA. MALDI-TOF MS: M/Z=832.64 (MH+).

Peptidomimetic P80 was prepared as P31 except for using FmocGpg(Pmc)OH, HOBt, DIC (1.5 eq each) instead of FmocArg(Pmc)OH, HOBt, DIC (3 eq each) in coupling step 3. MALDI-TOF MS: M/Z=859.19 (MH+), 896.14 (MK+).

Example 13

Preparation of Ac-Cha-Arg-Tic-Nle-N(Bn) CH2CH2OCH2CH2OH (P98) & Ac-Cha-Gpg-Tic-Nle-N(Bn)CH2CH2OCH2CH2OH (P101)

13.1: Preparation of 2-(2-Benzyl-[2-(2-hydroxyethoxy)ethyl]-carbamic acid 9H-fluoren-9-ylmethyl-ester

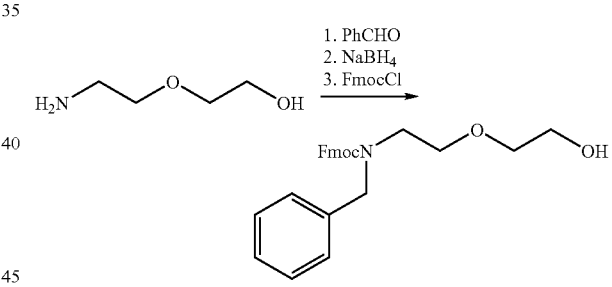

2-(2-Aminoethoxy)-ethanol (10 ml, 100 mmol) was dissolved in dry THF (80 ml). Benzaldehyde (10.5 ml, 103 mmol) was added followed by MS 4 Å and the mixture was stirred at r.t. for 3.5 h. The resulting solution was filtered and concentrated under reduced pressure to yield 17.41 g oily residue (89 mmol). This residue was dissolved in dry THF (180 ml) and the solution was cooled to 0° C. NaBH$_4$ (98 mmol) was added and the mixture was stirred at r.t for 3 h. The reaction was quenched by addition of 5 N aq. HCl (70 ml). The pH was adjusted to 11 by addition of Na$_2$CO$_3$ and the mixture was extracted with CH$_2$Cl$_2$ (4×). The combined organic extracts were dried over K$_2$CO$_3$, filtered and concentrated under reduced pressure to yield 15.3 g 2-(2-Benzylaminoethoxy)-ethanol, pure enough for further reaction.

Crude 2-(2-Benzylaminoethoxy)-ethanol (5.27 g, 27.0 mmol) was dissolved in dioxane (25 ml). Na$_2$CO$_3$ (10% in water, 35 ml) was added and the mixture was cooled to 0° C. After addition of FmocCl (7.81 g; 30.2 mmol) the mixture was stirred for 3.25 h. The mixture was concentrated under reduced pressure to remove dioxane. The resulting aq. mixture was extracted with CH$_2$Cl$_2$ (3×75 ml). The combined org. extracts were dried over Na$_2$SO$_4$, filtered and concentrated under reduced pressure. The residue was purified by flash chromatography using ethyl acetate/hexane (1:1) as eluent to give 9.1 g of the title compound as an oil. $^1$H-NMR (CDCl$_3$): 3.05-3.35 (m, 3 H), 3.45-3.75 (m, 5 H), 4.20-4.30 (m, 1 H), 4.45-4.55 (m, 3H), 4.69-4.68 (m, 1 H), 7.00-7.45 (m, 10H), 7.55-7.80 (m, 3 H).

13.2: Preparation of FmocN(Bn) CH$_2$CH$_2$OCH$_2$CH$_2$O-2-chlorotrityl Resin THF (15 ml) was added to 2-Chlorotrityl chloride resin (4.0 g, 1.2 mmol/g) and the mixture was agitated for 25 min. FmocN(Bn)CH$_2$CH$_2$OCH$_2$CH$_2$OH (6.1 g, 14.7 mmol) in THF (25 ml) was added followed by pyridine (850 μl, 10.5 mmol) and the mixture was heated to 65° C. for 15 h. MeOH (5 ml) was added and heating was continued for 35 min. The resin was filtered, washed with DMF (3×), CH$_2$Cl$_2$ (3×). MeOH (3×) and Et$_2$O (3×) to give 5.0 g. A small sample was dried carefully and deprotected with DCM/piperidine (1:1) for 30 min. Photometric determination of the resulting Fmoc-piperidine adduct (absorption at 301 nm) gave a resin loading of 0.45 mmol/g.

The peptidomimetic P98 was prepared using similar methodology to that described for Example 2.4 by deprotection and coupling using FmocN(Bn)CH$_2$CH$_2$OCH$_2$CH$_2$O-2-chlorotrityl resin (4.93 g, 2.2 mmol), starting with a deprotection step. Coupling on HN(Bn)CH$_2$CH$_2$OCH$_2$CH$_2$O-2-chlorotrityl resin was performed using HOBt (2.5 eq) DIC (2.5 eq) and FmocNleOH (2.5 eq) for 21 h. Coupling on Nle was performed using TBTU (3 eq), DIPEA (3.2 eq) and FmocTicOH (3 eq) in 12 ml DMF with a coupling time of 1.5 h. Coupling on Tic was carried out using FmocArg(Pmc)OH (3 eq), HOBt (3 eq) and DIC (3 eq) in 15 ml DMF over 20 h and coupling on Arg was done with FmocChaOH (3 eq), TBTU (3 eq) and DIPEA (3.2 eq) in 15 ml DMF over 1.5 h. After final acetylation, resin was washed with DMF (3×), MeOH (3×) and Et$_2$O (3×) to give 6.67 g. The resin was treated with 50 ml of TFA/water/thioanisole/1,2-ethanedithiol/triethylsilane 85.5:5:5:2,5:2 for 3.5 h at r.t. The resin was filtered off, washed with TFA and the filtrate was concentrated under reduced pressure. The product was precipitated by adding 450 ml of chilled diethyl ether to the residue. The suspension was centrifuged at 3300 rpm for 10 min, the supernatant was discarded, the precipitate was resuspended in chilled ether, centrifuged again and the supernatant was once again discarded. The precipitate was dissolved in acetonitrile and 0.1% aq TFA. The organic solvents were evaporated under reduced pressure and the aq. solution was freeze dried to give 1.38 g of crude product. Of this product 300 mg were purified by HPLC using a gradient of acetonitrile in 0.1% aq TFA to yield 209 mg pure P98. MALDI-TOF MS: M(Z=819.29 (MH+).

Peptidomimetic P101 was prepared as P98 except for using FmocGpg(Pmc)OH, HOBt, DIC (1.5 eq each) instead of FmocArg(Pmc)OH, HOBt, DIC (3 eq each) in coupling step 3. MALDI-TOF MS: M/Z=845.39 (MH+), 867.38 (MNa+), 883.36 (MK+).

Example 14

Competitive Binding of Compounds to MHC-II proteins DR4Dw4 and DR1

Competitive binding of the peptidomimetic compounds (1 n M-100 μM) was tested on DR4Dw4 (DRA1*0101 DRB1*0401), DR1 (DRA1*0101 DRB1*0101) and DR4Dw14 (DRA1*0101 DRB1*0404) using 6-(biotinamido)-hexanoyl-YAAFRAAASAKAAA-NH$_2$ as indicator peptide following the general protocol by Ito et al. (Exp. Med. 1996; 183: 2635-2644), and Siklodi et al. (Human Immunology 1998; 59: 463471) with some modifications.

A 10 fold dilution series of compounds (4 nM-400 μM) in 25% (v/v) DMSO/50 mM sodium phosphate, 150 mM sodium chloride, pH 7.5 (PBS) was prepared in a 96 well polypropylene plate blocked with 1% BSA/PBS for 1 hours at room temperature. The MHC-compound interaction mixtures were prepared in a similarly blocked 96 well polypropylene plate as follows; to 40 μl 2× buffer (PBS, 50 mM, pH 7.5, 2% (w/v) NP-40, 3.2 mM EDTA, 6.25% protease inhibitor cocktail: 0.32 g/l of Chymostatin, Antipain, Pepstatin A, Soybean trypsin inhibitor and Leupeptin each) were given 10 μl 0.8 μM indicator peptide, 20 μl compound solution of the appropriate dilution and 10 μl MHC-II DRA1*0101 DRB1*0401 (0.06 g/l), DRA1*0101 DRB1*0101 (0.03 g/l) or DRA1*0101 DRB1*0404 (0.015 g/l) in 0.5% (w/v) NP-40/PBS. Interaction mixtures lacking the peptidomimetic compound and both peptide mimetic compound and MHC-II were used as positive and negative controls, respectively. All interaction mixtures were set up in duplicates and were incubated for 16 hours at room temperature.

High binding capacity black FIA plates (Greiner, capture plates) were previously coated with 100 μl/well mAb LB3.1 (0.01 g/l) in PBS overnight at 4° C., and subsequently blocked with 200 μl/well 1% (w/v) BSA/PBS for 1 h at room temperature. After washing with PBS, 60 μl of the MHC-II-compound interaction mixtures were transferred from the interaction plate to the appropriate wells of the capture plate and incubated for 2 h at 4° C. The wells were washed six times with 200 μl/well of cooled (4 to 8° C.) 1×DELFIA wash (Wallac-ADL-GmbH, Freiburg), incubated with 100 μl of cooled Europium-streptavidin conjugate (Wallac-ADL-GmbH, Freiburg; diluted 1/1000 with DELFIA assay buffer) for 30 minutes at 4° C., again washed six times with cooled 1×DELFIA wash and, finally, incubated with 200 μl cooled DELFIA enhancement solution (Wallac-ADL-GmbH, Freiburg) for one hour at room temperature before reading the time-resolved europium fluorescence at $\lambda_{ex}$ Eu$^{3+}$: 340 nm and $\lambda_{em}$ Eu$^{3+}$: 613 (615) nm (Wallac Victor$^2$ 1420 Multilabel Counter, Wallac-ADL-GmbH, Freiburg).

Figure 3:
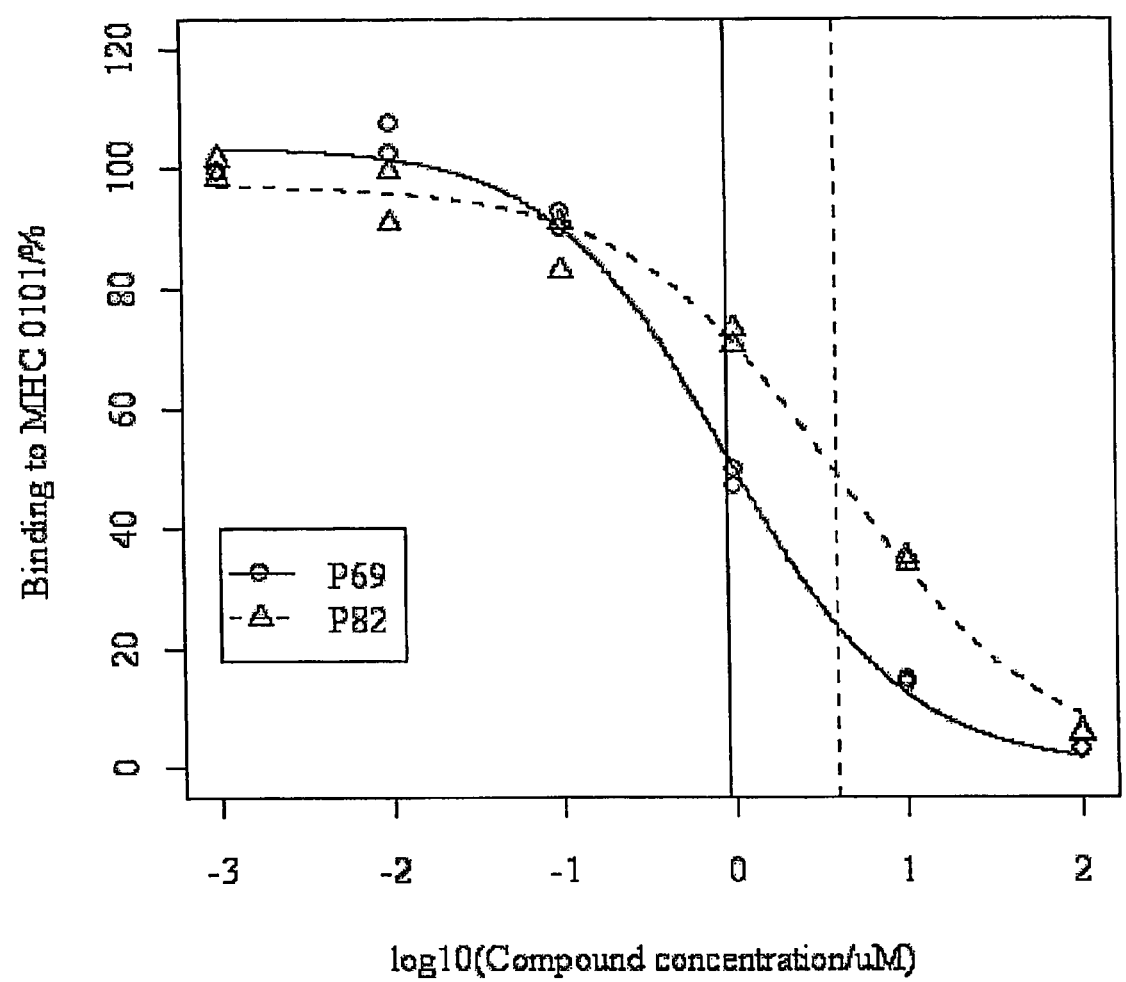
FIG. 3 Improved binding of a preferred Gpg (guanylpiperidyl glycine)-containing tetramer compound of the invention (P69) to MHC class II protein 0101 compared to the Arg-containing equivalent (P82). Using standard statistical software, non-linear logistic regression curves were fitted to replica data points generated according to Example 14. IC50s were estimated from the fitted curves and are represented by vertical lines of the appropriate line-type (P69 solid line, P82 dashed line) for the corresponding compound.
Figure 4:
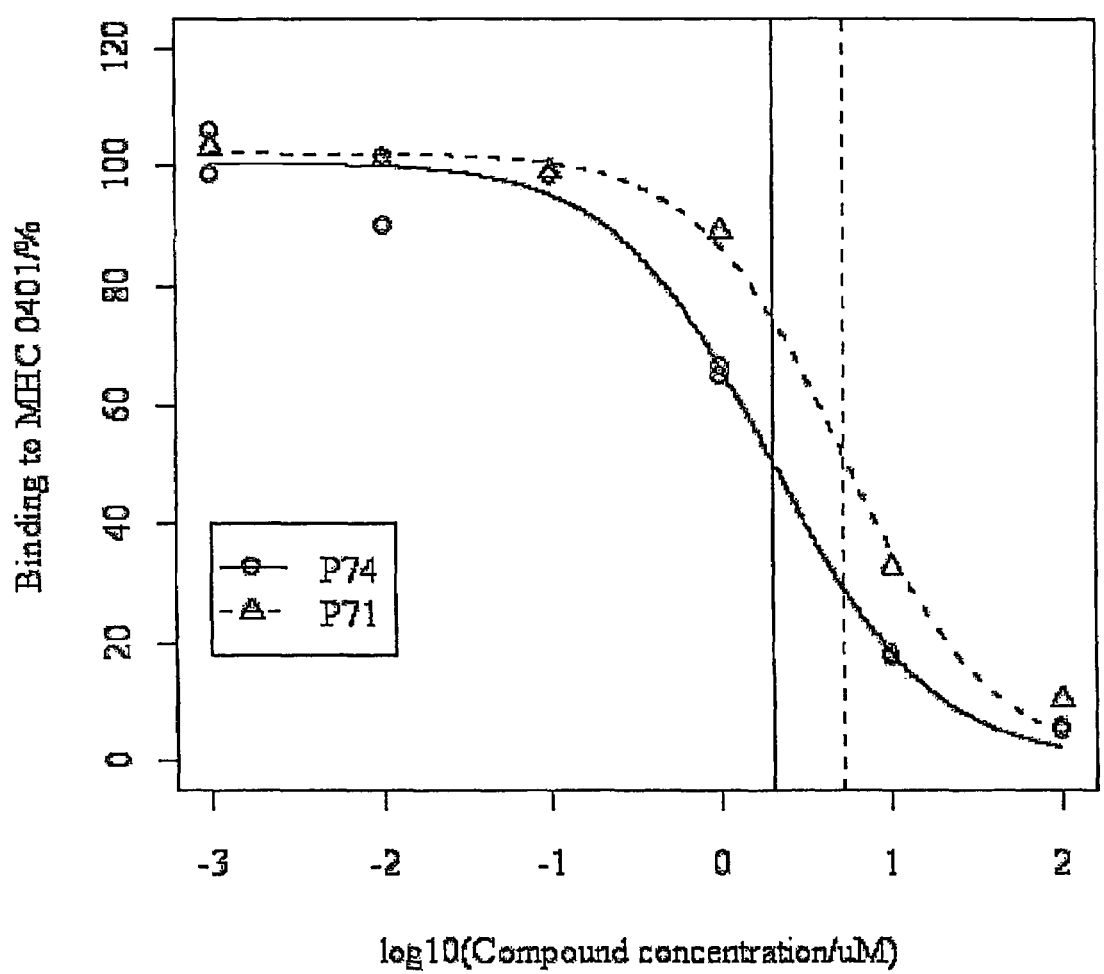
FIG. 4 Improved binding of a preferred Gpg (guanylpiperidyl glycine)-containing tetramer compound of the invention (P74) to MHC class II protein 0401 compared to the Arg-containing equivalent (P71). Using standard statistical software, non-linear logistic regression curves were fitted to replica data points generated according to Example 14. IC50s were estimated from the fitted curves and are represented by vertical lines of the appropriate line-type (P74 solid line, P71 dashed line) for the corresponding compound.
Figure 5:
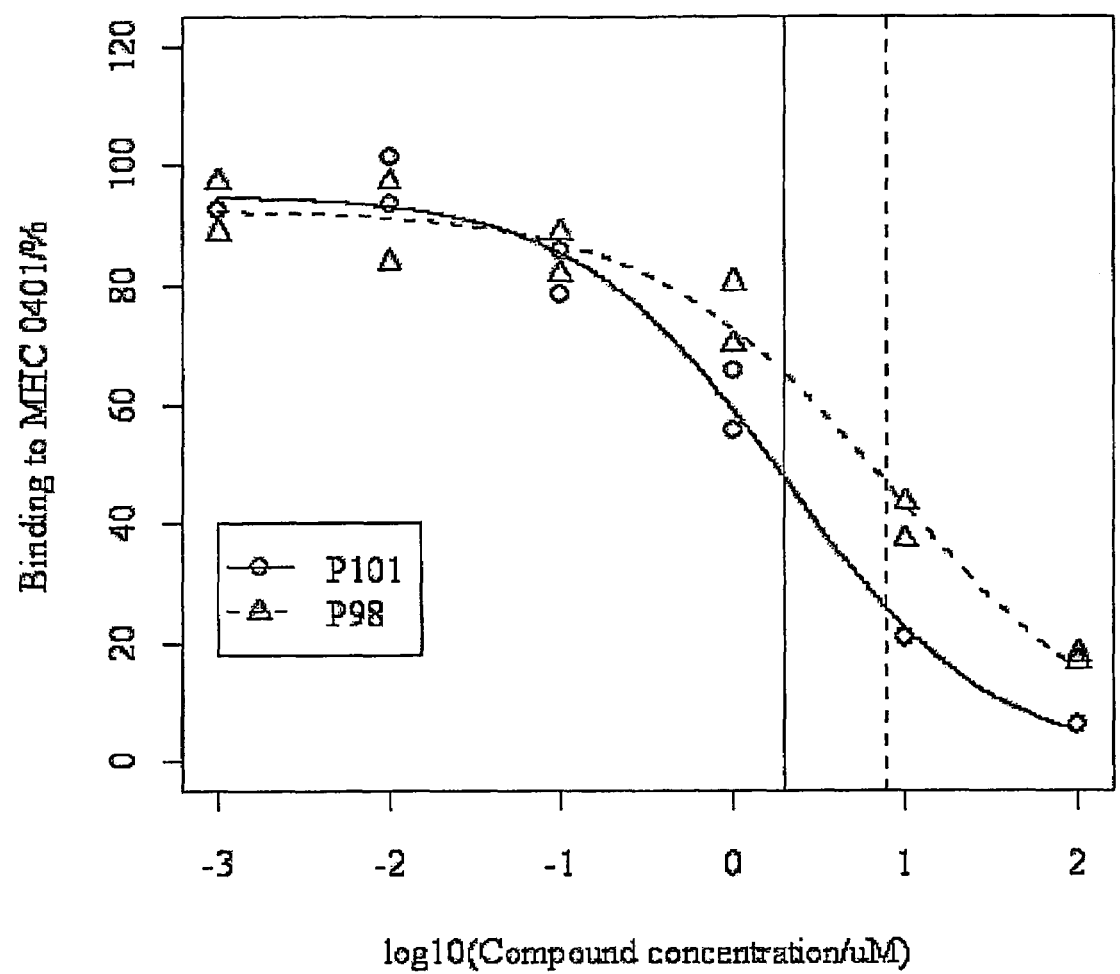
FIG. 5 Improved binding of a preferred Gpg (guanylpiperidyl glycine)-containing tetramer compound of the invention (P101) to MHC class II protein 0401 compared to the Arg-containing equivalent (P98). Using standard statistical software, non-linear logistic regression curves were fitted to replica data points generated according to Example 14. $IC_{50}s$ were estimated from the fitted curves and are represented by vertical lines of the appropriate line-type (P101 solid line, P98 dashed line) for the corresponding compound.

Table 3a shows (in bold) the improved affinity of Gpg-containing compounds of the invention to certain MHCII proteins as measured by IC50 according to this example. Table 3b shows the affinities of compounds according to Formula I to the same MHCII proteins. FIG. 1 shows the improved IC$_{50}$ of P53 (Gpg-containing) against MHCII 0401, a preferred heptamer compound of the invention, compared to the Arg-containing peptide (P51), and FIG. 3 shows the improved IC$_{50}$ of P74 (Gpg-containing) against MHCII 0101, a preferred tetramer compound of the invention, compared to the Arg-containing peptide (P71). FIG. 3 shows the improved IC$_{50}$ of P69 (Gpg-containing), a preferred tetramer compound of the invention, compared to the Arg-containing peptide CP82). FIG. 4 shows the improved IC$_{50}$ of P74 (Gpg-containing) against 0401, a preferred tetramer compound of the invention, compared to the Arg-containing peptide (P71). FIG. 5 shows the improved IC$_{50}$ of P101 (Gpg-containing), a preferred tetramer compound of the invention, compared to the Arg-containing peptide (P98).

Example 15

Competitive Binding of Compounds to MHC II Proteins Expressed on PRIESS and LG2 Cells Competitive binding of the peptidomimetic compounds (4 nM-400 µM) was tested on Priess (DR4Dw4: DRA1*0101 DRB1*0401) and LG2 (DR1: DRA1*0101 DRB1*0101) cells using 6-(biotinamido)-hexanoyl-Cha-Arg-Tic-Met-NH$_2$ as indicator peptide. The cells were cultured in RPMI 1640 (1×Gibco 42401-042) medium, supplemented with 10% heat-inactivated FCS (Biowhittaker), 2 mM L-Glutamine, 1% non-essential amino acids stock (Gibco 11140-035; 100×MEM), 1 mM sodium pyruvate, 0.1 mg/ml Canamycin and 3.4 ppm β-mercaptoethanol. For use in the binding assay the cells were re-suspended in medium containing 1% FCS at a density of 2.5×10$^6$ cells/ml.

The assay was performed in sterile 96 well polystyrene microtiter plates. A 10 fold dilution series of compounds (16 nM-1615 µM) in 1% FCS was prepared from 5 or 10 mM compound stock solutions in 10% DMSO/water. 50 µl of each compound dilution were added in duplicates to 50 µl of a 16 µM solution of indicator peptide in 1% FCS. Cell binding was initiated by adding 100 µl of 2.5×10$^6$ cells/ml 1% FCS to each well. Controls were included containing the DMSO concentration present in the solution with the highest compound concentration. The cells were incubated at 37° C., 6% CO$_2$. After 4 hours the cells were washed with 200 µl PBS and lysed in 200 µl lysis buffer (50 mM sodium phosphate, 150 mM sodium chloride, 1% (w/v) NP-40, 25 mM iodoacetamide, 1 mM PMSF, 3.1% protease inhibitor cocktail: 0.32 g/l of Chymostatin, Antipain, Pepstatin A, Soybean trypsin inhibitor and Leupeptin each, pH 7.5) for 10 min.

High binding capacity black FIA plates (Greiner, capture plates) were previously coated overnight at 4° C. with 100 µl/well mAb LB3.1 (0.01 g/l) in 50 mM sodium phosphate, 150 mM sodium chloride, pH 7.5 (PBS), and subsequently blocked with 200 µl/well 1% (w/v) BSA/PBS for 1 h at room temperature. After washing with PBS, 190 µl of cell lysate were transferred to the appropriate wells of the capture plate and incubated for 2 h at 4° C. The wells were washed six times with 200 µl/well cooled (4 to 8° C.) of 1×DELFIA wash (Wallac-ADL-GmbH, Freiburg), incubated with 100 µl of cooled Europium-streptavidin conjugate (Wallac-ADL-GmbH, Freiburg; diluted 1/1000 with DELFIA assay buffer) for 30 minutes at 4° C., again washed six times with cooled 1×DELFIA wash and, finally, incubated with 200 µl cooled DELFIA enhancement solution (Wallac-ADL-GmbH, Freiburg) for one hour at room temperature before reading the time-resolved europium fluorescence at $\lambda_{ex}$ Eu$^{3+}$: 340 nm and $\lambda_{em}$ Eu$^{3+}$: 613 (615) nm (Wallac Victor$^2$ 1420 Multilabel Counter, Wallac-ADL-GmbH, Freiburg).

Figure 6:
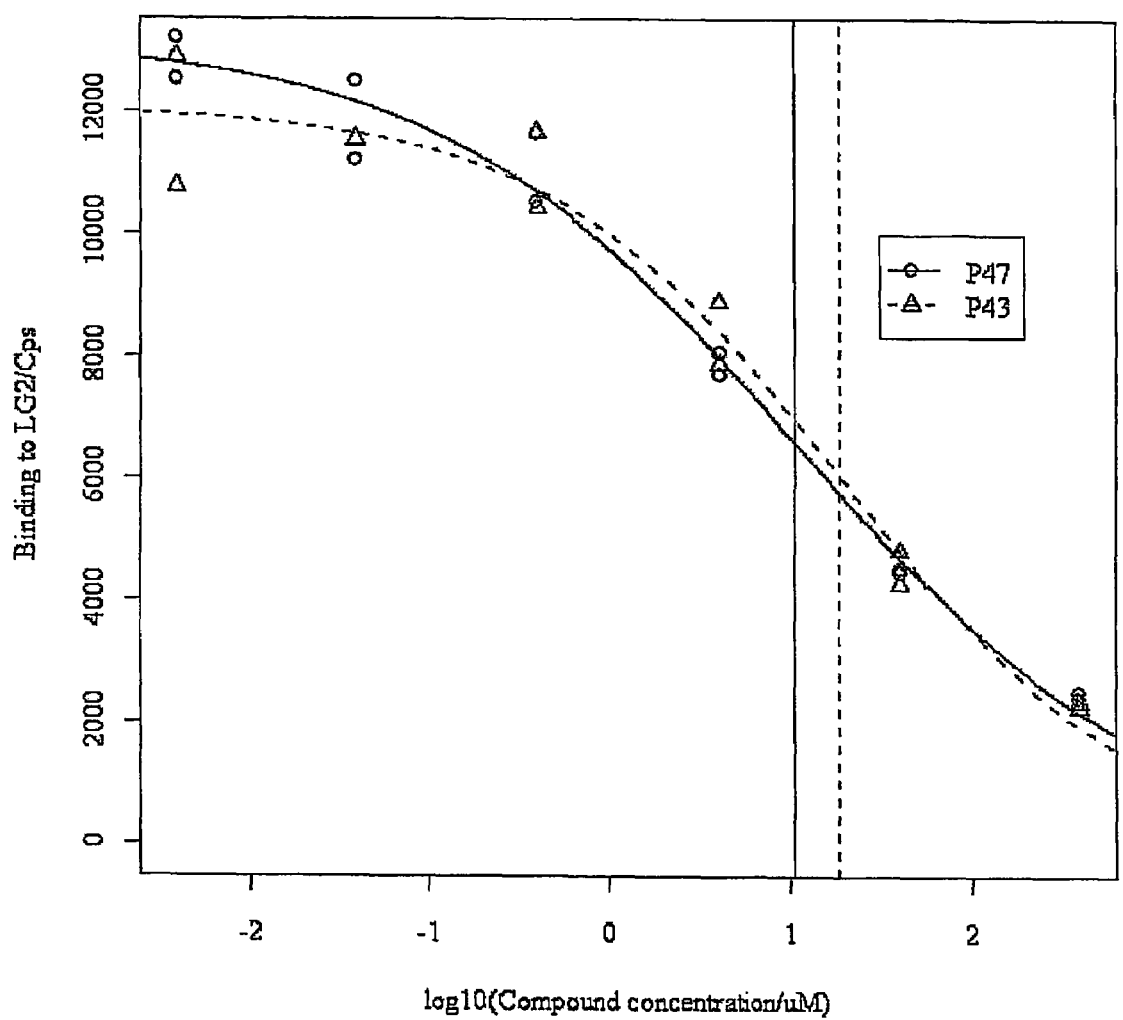
FIG. 6 Improved binding of a Gpg-containing heptamer compound of the invention (P47) to MHC class II protein expressed on the surface of LG2 cells compared to the Arg-containing equivalent (P43). Using standard statistical software, non-linear logistic regression curves were fitted to replica data points generated according to Example 15. $IC_{50}s$ were estimated from the fitted curves and are represented by vertical lines of the appropriate line-type (P47 solid line, P43 dashed line) for the corresponding compound.
Figure 7:
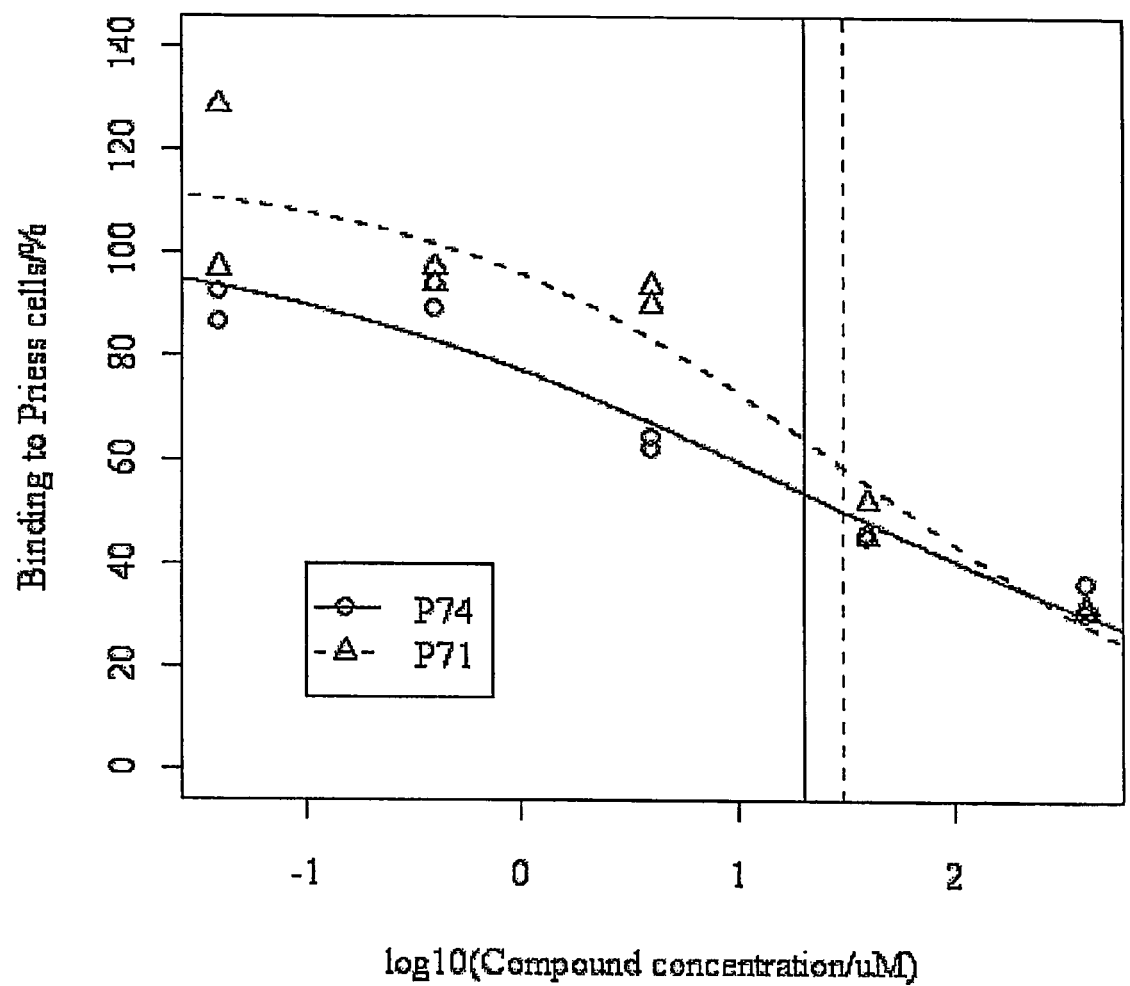
FIG. 7 Improved binding of a Gpg-containing tetramer compound of the invention CP74) to MHC class II protein expressed on the surface of Priess cells compared to the Arg-containing equivalent (P71). Using standard statistical software, non-linear logistic regression curves were fitted to replica data points generated according to Example 15. $IC_{50}s$ were estimated from the fitted curves and are represented by vertical lines of the appropriate line-type (P74 solid line, P71 dashed line) for the corresponding compound FIG. 8 Improved stability (arbitrary units) of Gpg-containing heptamer and tetramer compounds of the invention in rat plasma after 24 hours compared to the A rg-containing equivalent. Data for the corresponding G pg/Arg compounds are shown as adjacent bars.

Table 3a shows the improved affinity of Gpg-containing compounds of the invention to certain MHCII proteins expressed on the surface of cells sa measured by IC$_{50}$ according to this example. Table 3b shows the affinity of compounds of Formula I towards the same protreins expressed on said cells. FIG. 6 shows the improved IC$_{50}$ for inhibition of peptide binding to MHC protein expressed on LG2 cells of P47 (Gpg-containing), a preferred heptamer compound of the invention, compared to the Arg-containing peptide (P43). FIG. 7 shows the improved IC$_{50}$ for inhibition of peptide binding to MHC protein expressed on Priess cells of P74 (Gpg-containing), a preferred tetramer compound of the invention, compared to the Arg-containing peptide (P71).

Example 16

Stability of Compounds in Blood Plasma

The stability of the peptidomimetic compounds was determined in rat (Charles River Laboratories, Sulzfeld), mouse (Charles River Laboratories, Sulzfeld) and human (Bayerisches Rotes Kreuz, München) blood plasma (E. R. Garrett and M. R. Gardner, J Pharmaceutical Sciences 71 (1982) 14-25).

Figure 8:
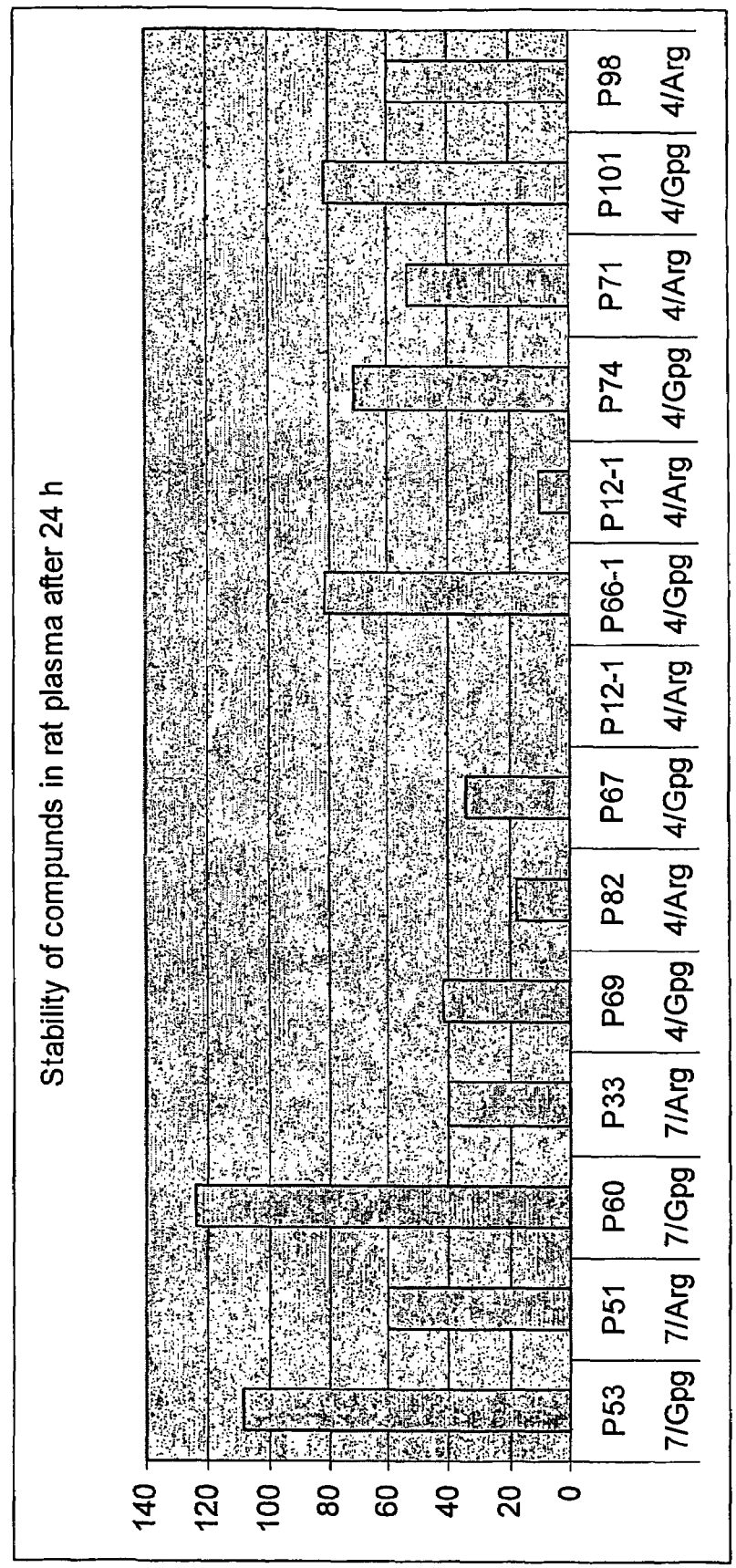

Table 3a shows the improved stability (in bold) of Gpg-containing compounds of the invention in blood plasma, and FIG. 8 displays improved stability (arbitrary units) of: a Gpg-containing heptamer compound of the invention (P53) in rat plasma after 24 hours compared to the Arg-containing equivalent (P51); a Gpg-containing tetramer compound of the invention (P66-1) compared to the Arg-containing equivalent (P12-1); a Gpg-containing tetramer compound of the invention (P69 compared to the Arg-containing equivalent (P82); other preferred compounds of the invention compared to their Arg-containing equivilent. Table 3b shows improved stability (in bold) of compounds according to Formula I compared to compounds with an NH$_2$ terminating group.

Compound stock solutions were diluted into blood plasma to give a final compound concentration of 5 µM and the mixtures were incubated at 37° C. At 0, 6 and 24 hours 1 ml samples were drawn and the plasma proteins were precipitated by the addition of 3 ml acetonitrile p.a. and whirlmixing. The precipitate was pelleted by centrifugation at 2000 g for 5 minutes. The supernatant was evaporated off to dryness and the residue was reconstituted in 400 µl 50% acetonitrile, 0.1% TFA in water.

After filtration (0.2 µm) 200 µl of the solutions were analysed by reverse phase HPLC (PerSeptive Biosystems; Nucleosil 100-5 C18, 12.5×0.46 cm; 20-50% acetonitrile in 0.1% aqueous TFA in 30 minutes), and the amount of compound remaining was estimated by integration of the appropriate peak. PBS controls were prepared for unstable compounds accordingly.

Example 17

Stability of Compounds Towards Degradation by Cathiepsin B1 and D

The stability of the peptidomimetic compounds towards lysosomal degradation was examined by incubation with Cathepsin B1 (EC 3.4.22.1 from bovine spleen; Sigma-Aldrich, Taufkirchen; dissolved at 10000 U/l in ddH$_2$O) and D (EC 3.4.23.5 from bovine spleen; Sigma-Aldrich, Taufkirchen; dissolved at 10000 U/l in ddH$_2$O) for four hours at 37° C. using a compound concentration of 50 µM and an enzyme/substrate ratio of 0.4 U/µmol. The samples contained 25 ppm 4-isopropyl benzyl alcohol (IPBA; Sigma-Aldrich, Taufkirchen) as internal standard.

Assay buffer was prepared by adding 35 µl of a 1% IPBA in DMSO solution and 28 µl of a 10000 U/l Cathepsin B1 or Cathepsin D stock solution to 14 ml of 100 mM sodium acetate, 1 mM EDTA, 1 mM DTT, pH 5.00 or 100 mM sodium acetate, pH 4.50, respectively. 8.8 µl of a 5 mM (or 4.4 µl of a 10 mM) compound stock solution (in 10% DMSO/water) were placed into a 1.5 ml Eppendorf tube. The reaction was started by adding 875 µl fully supplemented assay buffer to each tube, whirlmixing and incubation at 37° C. At 0 and 4 hours 400 µl samples were taken and the enzyme was inactivated by addition of 40 µl 150% TFA aq. The samples were kept frozen at –20° C. until analysis by RP-HPLC (200 µl injection volume; Nucleosil 100-5 C18, 12.5×4.6 cm; Gradient: 20-50% acetonitrile in 30 min).

The enzyme activity of Cathepsin B1 and Cathepsin D was controlled by incubation of Ac-Cha-RAMASL-NH$_2$ and QYIKANSLFIGITELK, respectively, which both were completely degraded within 4 hours.

Compounds co-eluting with the internal standard during RP-HPLC analysis were tested without the standard as Example 16.

Table 3 (a, b and c) shows the stability of compounds of the invention against certain Cathepsin enzymes.

Example 18

In Vivo Inhibition of T Cell Activation from 0401(DR4) and 0404(DR14) chimeric MHCII-Mice by co-Immunisation Mouse strains DR4 and DR14 carry chimeric MHC-II transgenes that encode the N-terminal domains of the respective DR molecules (forming the peptide binding site) and the remaining (2nd extracellular domains, transmembrane and intracytoplasmic domains) of the murine class II molecule I Ed. These strains are deficient of other murine class II, and thus, all helper T cell responses are triggered by peptides presented in the respective human MHC-II binding site. As an initial in vivo test of subject inhibitors designed to bind to DR, DR-transgenic mice were co-immunized with a pre-defined dose of protein antigen and different amounts of the compound antagonist to be tested. In this set-up, both antigen and compound were emulsified together in complete Freund's adjuvant (CFA), and thus, a direct competition between the two components for presentation by DR was tested. Readout of the assay is ex vivo antigen-specific activation of T cells from regional lymph nodes explanted 9 days after co-immunization. In a typical experiment, antigen dose-response was investigated, and the curves from mice immunized with antigen were compared to those from mice co-immunized with antigen+compound. The dose response curves were generated using lymph node cells pooled at equal numbers from 2-3 mice per experimental group. The experimental system also permits assessment of inherent antigenicity of the compound antagonist. This was done by setting up a dose-response study from the same cell pool using different concentrations of the compund under investigation instead of the antigen. As a specificity control, the response to Purified Protein Derivative (PPD), the major protein component of CFA, was tested in the same cell pool.

Figure 14:
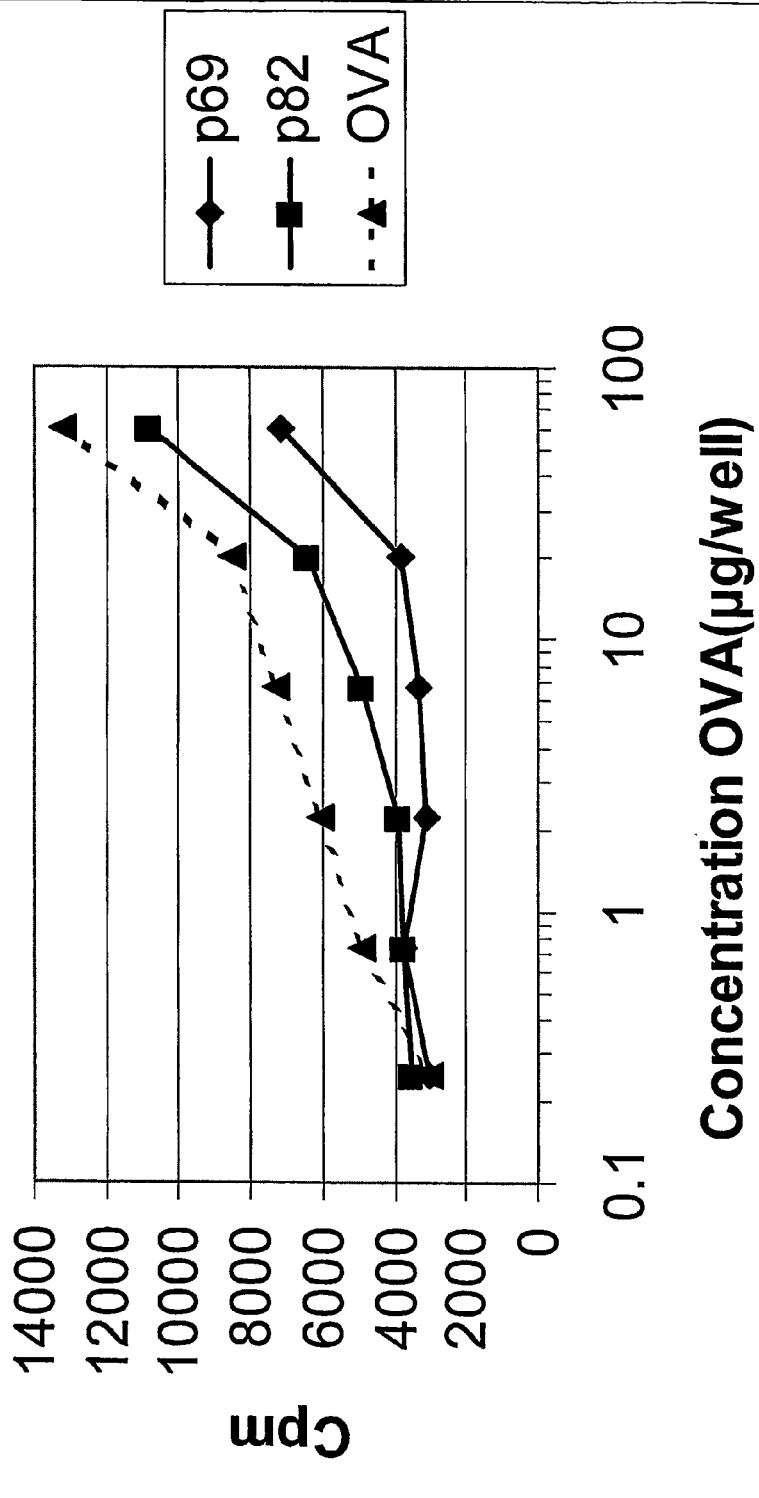
FIG. 14 Superior in-vivo immunosuppressive properties of P69 (Gpg-containing) a preferred tetramer compound of the invention following co-imunisation with antigen as measured by T-cell proliferation, compared to the Arg-containing equivilent (P82).
Figure 15:
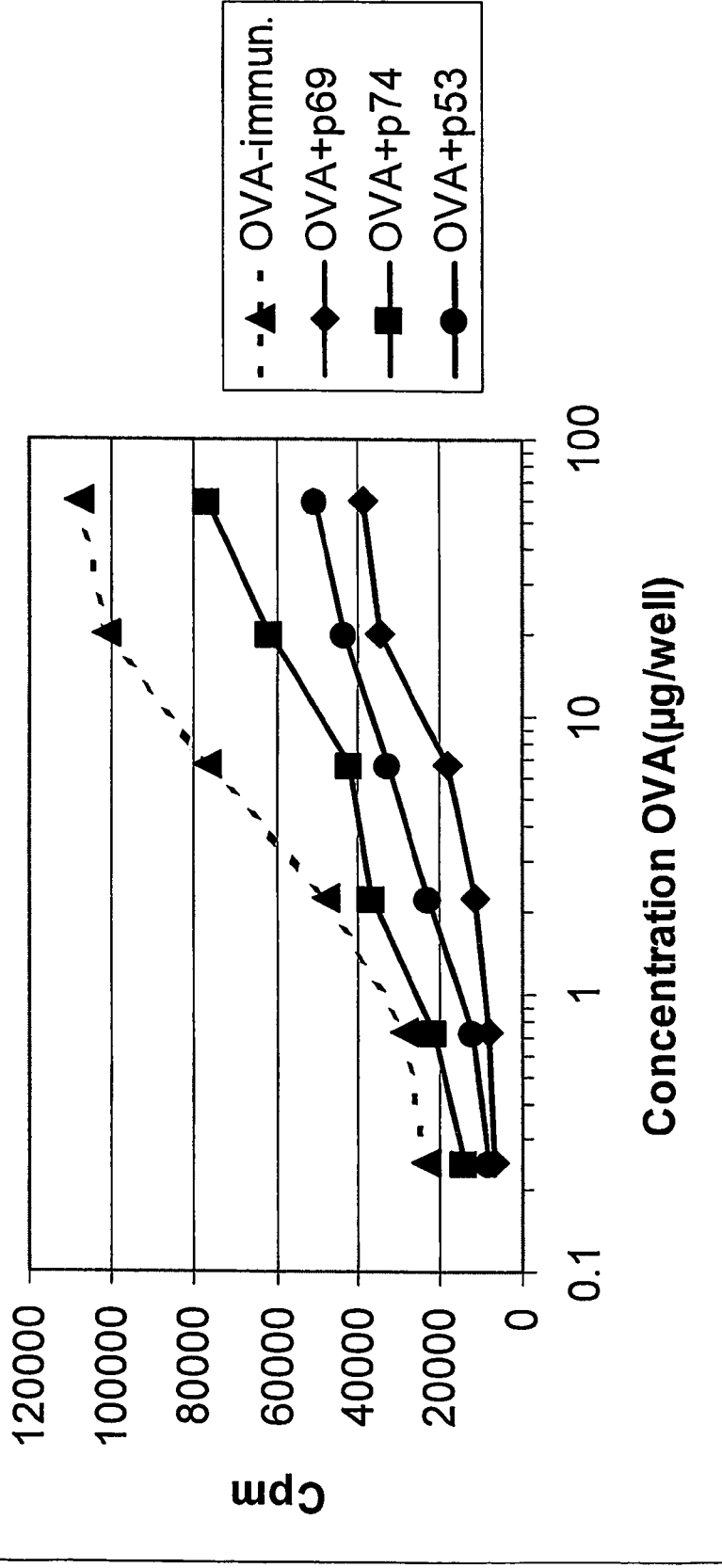
FIG. 15 In-vivo immunosuppressive properties of preferred tetramer and heptamer compounds of the invention following co-imunisation with antigen as measured by T-cell proliferation.

FIG. 14 shows improved in-vivo inhibitory effect of a preferred tetramer compound of the invention (P69) compared to the Arg-contaiing equivilent (p82). FIG. 15 shows the in-vivo inhibitory effect of a preferred tetramer and heptamer compounds of the invention.

An estimate of overall inhibitory potential for a compund under investigation was taken by calculating the mean % inhibition from the control over 3 concentrations of antigen; 6.7, 20 and 60 ug. Table 4 shows these estimates of overall inhibitory potential of certain compounds of the invention, together with certain Arg-containing equivalents. All Gpg conataining compounds have significant immunosupressive properties in one or both of the in-vivo models. Gpg-containing compounds also show improved activity or improved specificity over the Arg-containing equivilent. Further, compounds according to Formula I show activity in this assay.

18.1 Preparation of Compounds for Co-Immunisation

Compounds of the invention were injected as an Emulsion prepared using CFA (Bacto Adjuvant Complete H37 Ra, Difco, Order-No. 3113-60); proteins 10 mg/ml in PBS, inhibitors 5 µM in 10% DMSO. CFA, PBS, antigen, and inhibitor were placed in the barrel of a 5-ml syringe (total volume not more than 1 mL). The mixture was sonicated at an amplitude less than 40% (30-35%) for two separated 15 s periods. The emulsion should seem to be hard and not liquid at this point. A drop of emulsion placed on the surface of water should not melt. The resulting emulsion was pushed through the needle into a 1 ml syringe with a needle (Gr.18, 26G×1"), and air bubbles were removed. Mice were co-immunized with 50 µg protein and 210 nM compound antagonist in final 100 µl emulsion into the tail base. Antigen+ Compound and CFA are mixed 1:1 vol/vol. The best results are obtained using DR 4 mice immunised with HEL and DR 14 mice immunized with OVA.

18.2 Immunisation of Mice

Mice were injected at the tail-base as follows: Holding the tail of a mouse with thumb and middle finger, the index finger was placed under the base of the mouse's tail. The needle of the syringe was inserted about 1.5 cm from the tail base (hairy end) under the skin and pushed about 1 cm into the tail. 100 µl emulsion was injected into the mouse. After 9 days, mice were killed and lymph nodes removed.

18.3 T Cell Proliferation Assay After Co-Immunisation

The inhibitory effect of the candidate compounds on T-cell activation was tested using T-cells and antigen-presenting cells isolated from the lymph nodes of chimeric DR4-IE transgenic mice (Taconic, USA) previously co-immunized with hen egg lysozyme plus compound, or DR14-IE transgenic mice co-immunized with ovalbumin plus compound according to standard procedures (Adorini et al., 1988, Mueller et al., 1990; *Current Protocols in Immunology*, Vol. 2, 7.21; Ito et al., 1996).

About 9 days (e.g., 8-10 days) after immunisation, mice were killed and lymph nodes removed, a T cell proliferation assay was performed according to Example 19.1, using increasing amounts of antigen on lymph node cells from mice that had been co-immunised with protein antigen and compound antagonist. The control line was immunised without compound.

Antigen dilutions were prepared and distributed on a 96-U-Well-MTP according to the assay plan below. PPD serves as a positive control for T-cell proliferation.

Medium (negative control)

100 µl HL-1
100 µl cells (2.5 × 10$^5$ cells)
PPD (positive control)

100 µl PPD solution (100 µg/ml))
100 µl cells (2.5 × 105 cells)
Inhibitor control 100 µl Compound solution (100-3.125 µM)
100 µl cells (2.5 × 105 cells)

-continued

Antigen-Titration (600 μg/ml-0.82 μg/ml)

100 μl antigen solution
100 μl cells (2.5 × 105 cells)
Wash medium 97.5% RPMI
1.5% FCS
1% Kanamycin (Stock solution 10 mg/ml → final 0.1 mg/ml)
HL-1 medium 98% HL-1 Medium (BioWittaker Europe Order-no. 77201)
1% L-Glutamin (Stocksolution 200 mM → final 2 mM)
1% Kanamycin (Stocksolution 10 mg/ml → final 0.1 mg/ml)
no serum
Stock solutions HEL (Lysozyme Grade III: From Chicken Egg White; Sigma L-7011) 10 mg/ml PBS
OVA (Albumine, Chicken Egg; Sigma A-2512) 4 mg/ml PBS
PPD (Tuberculin PPD; Statens Serum Institut; Order-no. 2391) 1 mg/ml (ready for use)
Solutions for use HEL: Dilute stock solution 1:83 with HL-1 medium (120 μg/ml) → final concentration in well 30 μg/ml.
OVA: Dilute stock solution 1:48 with HL-1 medium (84 μg/ml) → final 21 μg/ml.
PPD: Dilute stock solution 1:10 with HL-1 medium (100 μg/ml) → final 25 μg/ml.

Example 19

In Vitro Inhibition of T Cell Activation by Compounds of the Invention

Figure 9:
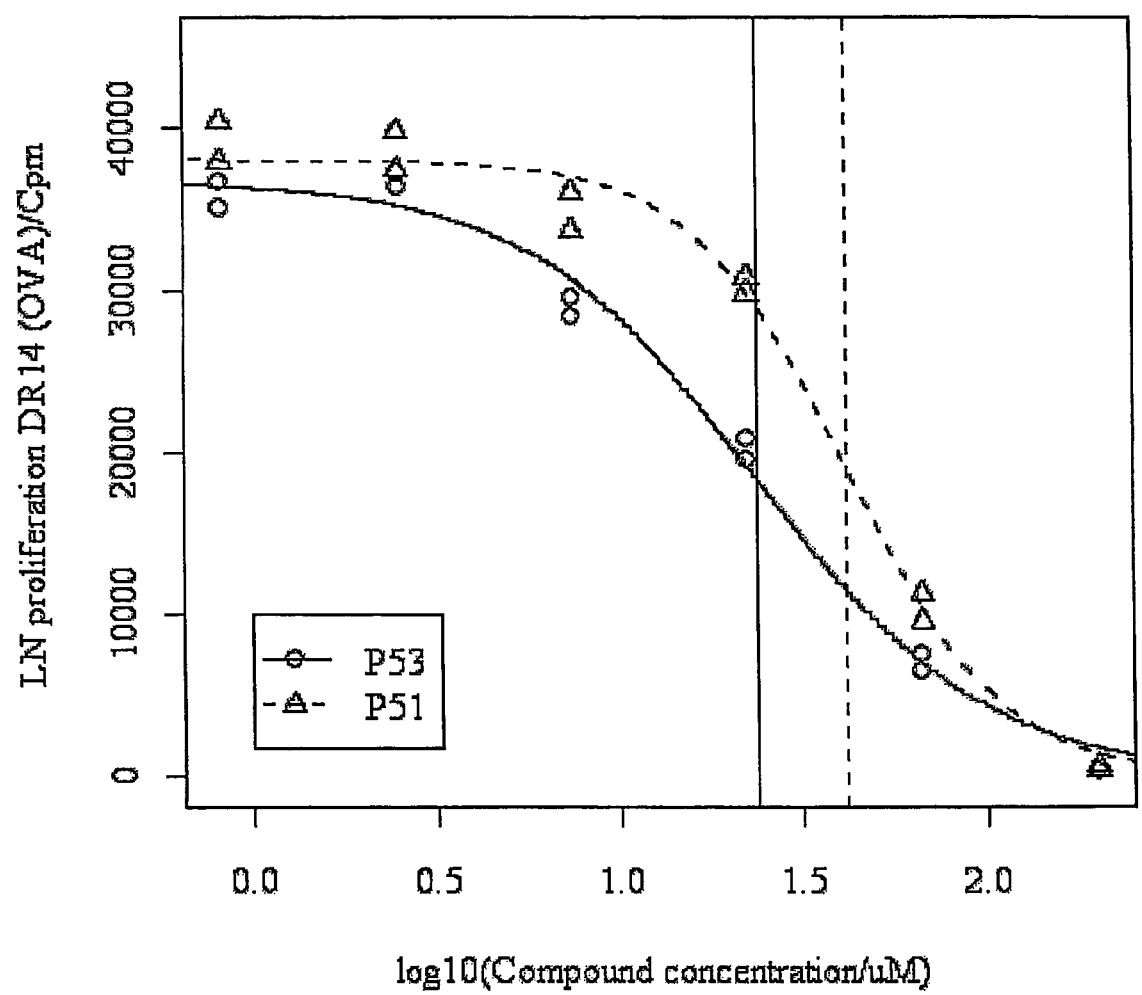
FIG. 9 A dose-respose curve demonstrating improved immunosuppressive properties as measured by a T-cell activation assay of P53 (Gpg-containing) a preferred heptamer compound of the invention, compared to the Arg-containing peptide (P51). Using standard statistical software, non-linear logistic regression curves were fitted to replica data points generated according to Example 19. $IC_{50}s$ were estimated from the fitted curves and are represented by vertical lines of the appropriate line-type (P53 solid line, P51 dashed line) for the corresponding compound.
Figure 10:
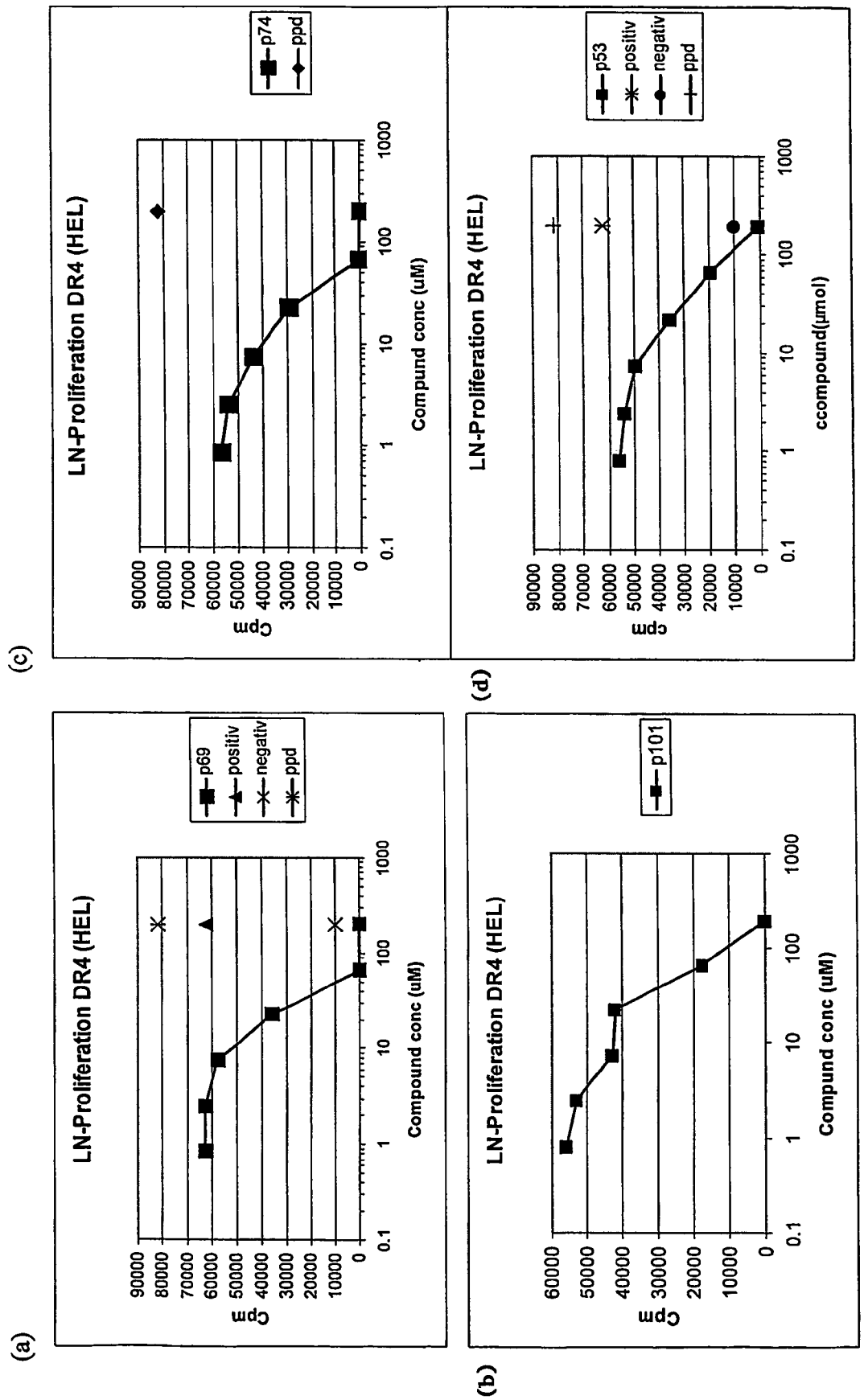
FIG. 10 Dose-respose curves demonstrating immunosuppressive properties as measured by a T-cell activation assay of preferred compounds of the invention (a) P69, (b) P101, (c) P74 and (d) P53.

Immunomodulatory properties of compounds under investigation were tested using an assay that measures T cell proliferation. Table 3 (a and b) shows the IC50 (uM) and maximal inhibition (%) of certain compounds. FIG. 9 displays a dose-response curve demonstrating improved immunosuppressive properties as measured by a T-cell activation assay of P53 (Gpg-containing), a preferred heptamer compound of the invention, compared to the Arg-containing peptide (P51). A dose-response curve of another compound of the invention (P41-1) is also shown. FIG. 10 displays a dose-response curves demonstrating the immunosuppressive properties as measured by a T-cell activation assay of various preferred compounds of the invention; P69, P74, P101 and P53.

The compounds were tested as follows to inhibit the proliferative T cell response of antigen-primed lymph node cells from mice carrying a chimeric mouse-human class II transgene with an RA-associated peptide binding site, and lack murine class II molecules (Muller et al., 1990; Woods et al., 1994; Current Protocols in Immunology, Vol. 2, 7.21; Ito et al., 1996). Here, the immunization takes place in vivo, but the inhibition and readout are ex vivo. Transgenic mice expressing MHC class II molecules with binding sites of the RA associated molecule, DRB*0401 were commercially obtained. These mice lack murine MHC class II, and thus, all Th responses are channelled through a single human RA-associated MHC class II molecule (Ito et al. 1996). These transgenic mice represent a model for testing human class II antagonists.

19.1 T Cell Proliferation Assay

The inhibitory effect of the compounds under investigation were tested on T-cell proliferation measured using chimeric T-cells and antigen presenting cells isolated from the lymph nodes of chimeric 0401-IE transgenic mice (Taconic, USA) previously immunized with hen egg ovalbumin (Ito et al. 1996) according to standard procedures. $1.5 \times 10^5$ cells are incubated in 0.2 ml wells of 96-well tissue culture plates in the presence of ovalbumin (30 μg per well—half-maximal stimulatory concentration) and a dilution series of the compound under test (from around 0.1 to 200 uM) in serum free HL-1 medium containing 2 mM L-glutamine and 0.1 g/l Kanamycin for three days. Antigen specific proliferation is measured by 3H-methyl-thymidine (1 μCi/well) incorporation during the last 16 h of culture (Falcioni et al., 1999). Cells are harvested, and 3H incorporation measured using a scintillation counter (TopCount, Wallac Finland). Inhibition of T-cell proliferation on treatment with the compound may be observed by comparison to control wells containing antigen.

Example 20

Figure 11:
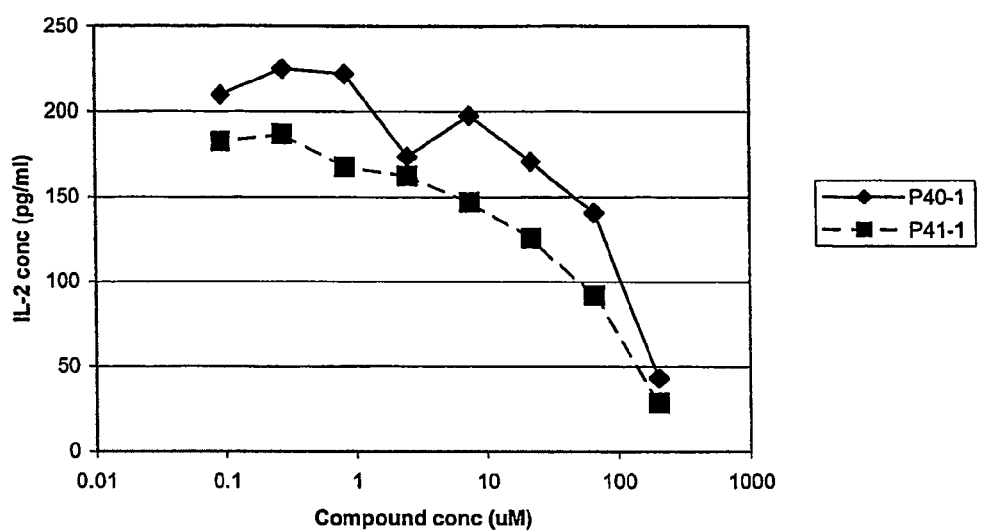
FIG. 11 A dose-response curve demonstrating the improved immunosuppressive properties as measured by IL-2 secretion of P41-1 (Gpg-containing) (squares and dashed line), a heptamer compound of the invention, compared to the Arg-containing peptide (P40-1) (diamonds and solid line).
Figure 12:
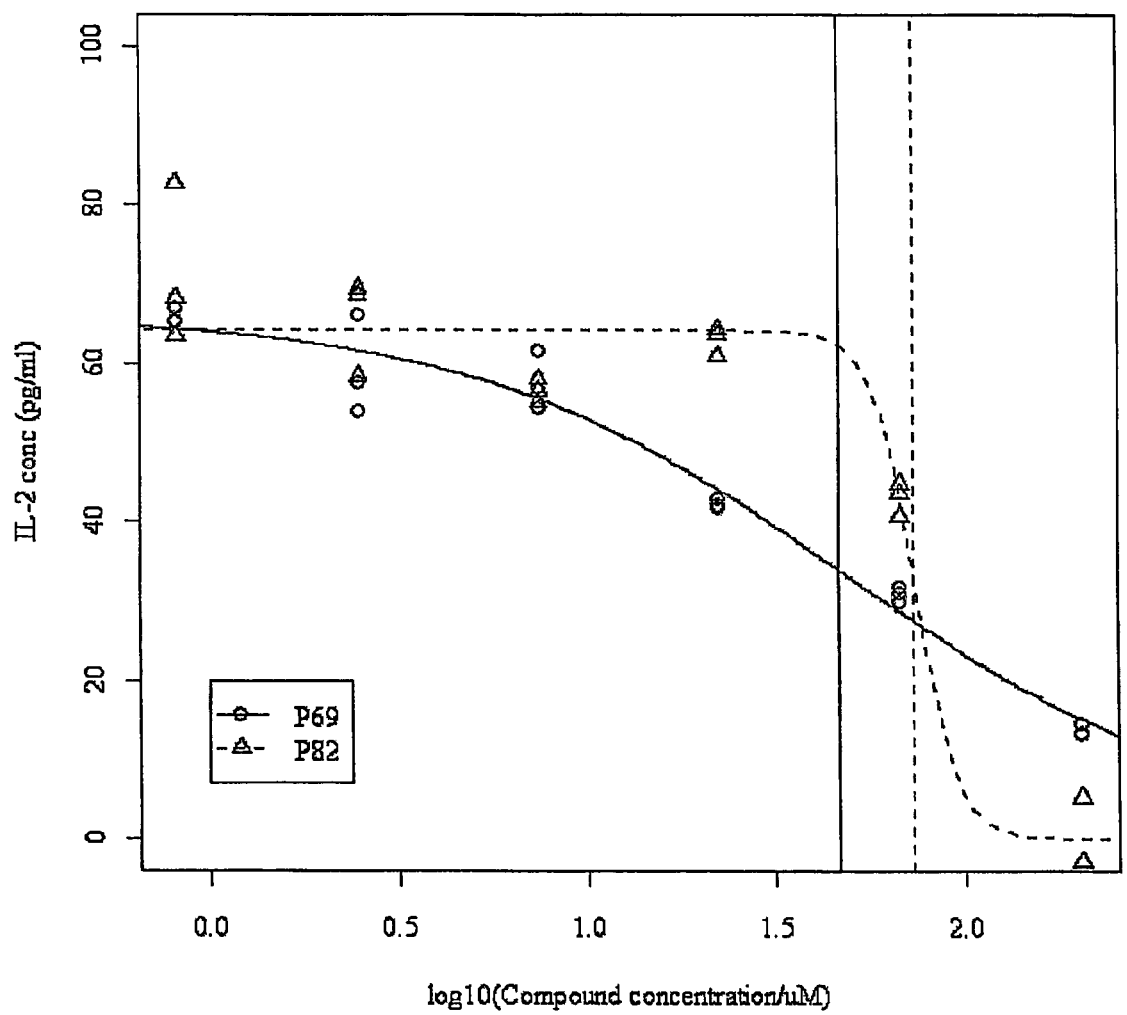
FIG. 12 A dose-response curve demonstrating the improved immunosuppressive properties as measured by IL-2 secretion of P69 (Gpg-containing, a preferred tetramer compound of the invention, compared to the Arg-containing peptide (P82). Using standard statistical software, non-linear logistic regression curves were fitted to replica data points generated according to Example 20. $IC_{50}s$ were estimated from the fitted curves and are represented by vertical lines of the appropriate line-type (P69 solid line, P82 dashed line) for the corresponding compound FIG. 13 The immunosuppressive properties of P53 (Gpg-containing) as measured by IL-2 secretion (squares and solid line), a preferred heptamer compound of the invention, compared to a DMSO control (diamonds and dotted line).
Figure 13:
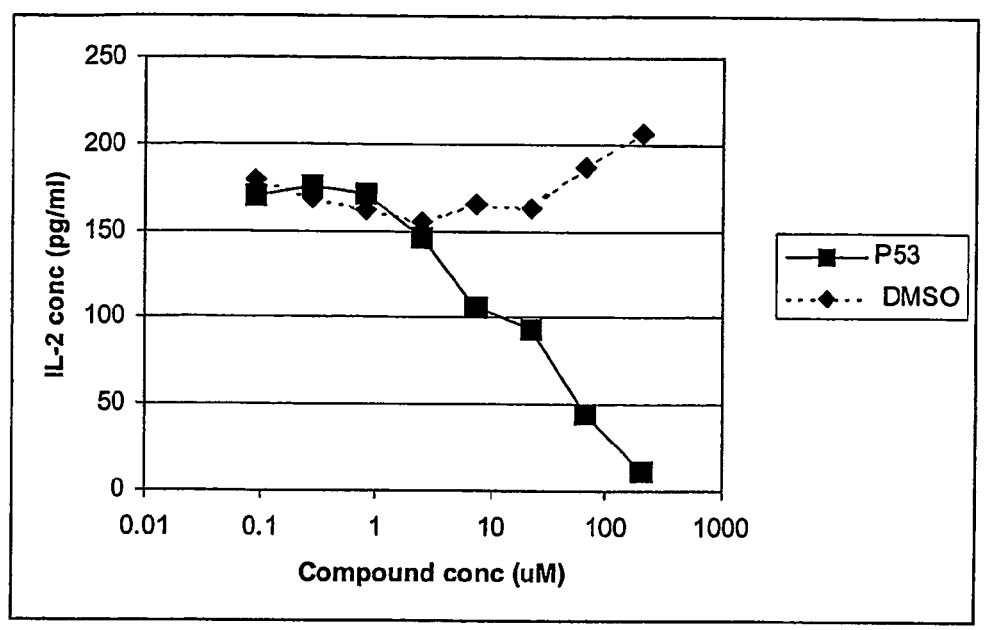

Inhibition of IL-2 Secretion Front T-Cell Hybridoma Cells by Compounds of the Invention The Gpg-containing compounds of the invention displayed substantial immunomodulatory properties within an assay measuring IL-2 secretion from immortalized T-cells. Table 3a shows the $IC_{50}$ (uM) and maximal inhibition (%) of Gpg compounds in this assay. Table 3b shows improved activity (in bold) of tetramer compounds according to Formula I compared to those containing an $NH_2$ terminating group. FIG. 11 displays a dose-response curve demonstrating the improved immunosuppressive properties as measured by IL-2 secretion of P41-1 (Gpg-containing), a heptamer compound of the invention, compared to the Arg-containing peptide (P40-1), and FIG. 12 displays a dose-response curve demonstrating the improved immunosuppressive properties as measured by IL-2 secretion of P69 (Gpg-containing), a tetramer compound of the invention, compared to the Arg-containing peptide (P82). FIG. 13 shows the immunosuppressive properties of P53 (Gpg-containing), a preferred heptamer compound of the invention, compared to a DMSO control.

The immunomodulatory properties of the compounds under investigation was investigated by measuring IL-2 secretion from the hybridoma cell line T-Hyb 1 stimulated using DR-transgenic antigen presenting cells (APC) under conditions of half-maximal antigen stimulation. IL-2 secretion was detected and measured using a standard ELISA method provided by the OptiEIA mouse IL-2 kit of Pharmingen (Torrey Pine, Calif., USA). APCs were isolated from the spleen of unimmunized chimeric 0401-IE transgenic mice ato et al. 1996) according to standard procedures. $1.5 \times 10^5$ APCs were added to 0.2 ml wells of 96-well in RPMI medium containing the following additives (all from Gibco BRL and PAA): 10% FCS, 2 mM L-glutamine, 1% non-essential amino acids, 1 mM sodium pyruvate and 0.1 g/l kanamycin. Hen egg ovalbumin was added to a final concentration of 200 μg/ml in a final volume of 100 μl of the above medium, the cells incubated with this antigen for 30 m in at 37° C. under 6% $CO_2$. Compounds were added to each well at various concentrations (typically in a range from 0.1 to 200 μM), the plate incubated for 1 h at 37° C./6% $CO_2$ and $2 \times 10^5$ T-Hyb 1 cells added to give a final volume of 200 μl in the above medium. After incubation for 24 h, 100 μl of supernatant was transferred to an ELISA plate (Nunc-Immuno Plate MaxiSorp surface, Nunc, Roskilde, DK) previously coated with IL-2 Capture Antibody (BD Pharmingen, Torrey Pine, Calif., USA), the amount of IL-2 was quantified according to the manufacturer's directions using the OptiEIA Mouse IL-2 kit and the plate read using a Victor V reader (Wallac, Finland). Secreted IL-2 in pg/ml was calibrated using the IL-2 standards provided in the kit.

The T-cell hybridoma line T-Hyb1 was established by fusion of a T-cell receptor negative variant of the thymoma line BW 5147 (ATCC) and lymph node cells from chimeric 0401-IE transgenic mice previously immunized with hen egg ovalbumin (Ito et al. 1996). The clone T-Hyb1 was selected for the assay since it responded to antigen specific stimulation with high IL-2 secretion.

Example 21

Immunomodulatory Activity of Compounds of the Invention Within Mouse Disease Models Compounds showing the best profile (binding affinity, protease stability, T cell inhibition in vitro and in vivo) are tested for their therapeutic potential in MHC-II transgenic mouse models of autoimmune diseases, namely collagen induced arthritis (CIA)—a model for rheumatoid arthritis; and experimental autoimmune encephalomyelitis (EAE)—a model for multiple sclerosis.

CIA is induced by immunization with type II collagen in HLA-DR1 transgenic mice as described by Rosloniec et al (J. Exp. Med. 1997; 185: 113). After disease onset, mice are treated with compounds at the maximal tolerated dose s.c. for two weeks, and the disease development compared to that in mice treated with solvent only as follows:

| Day | Treatment |
| --- | --- |
| 1 | Immunization (bovine C-II + CFA) |
| 19-40 | Compound injected s.c. starting at disease onset 5× per week for 3 weeks |

Figure 16:
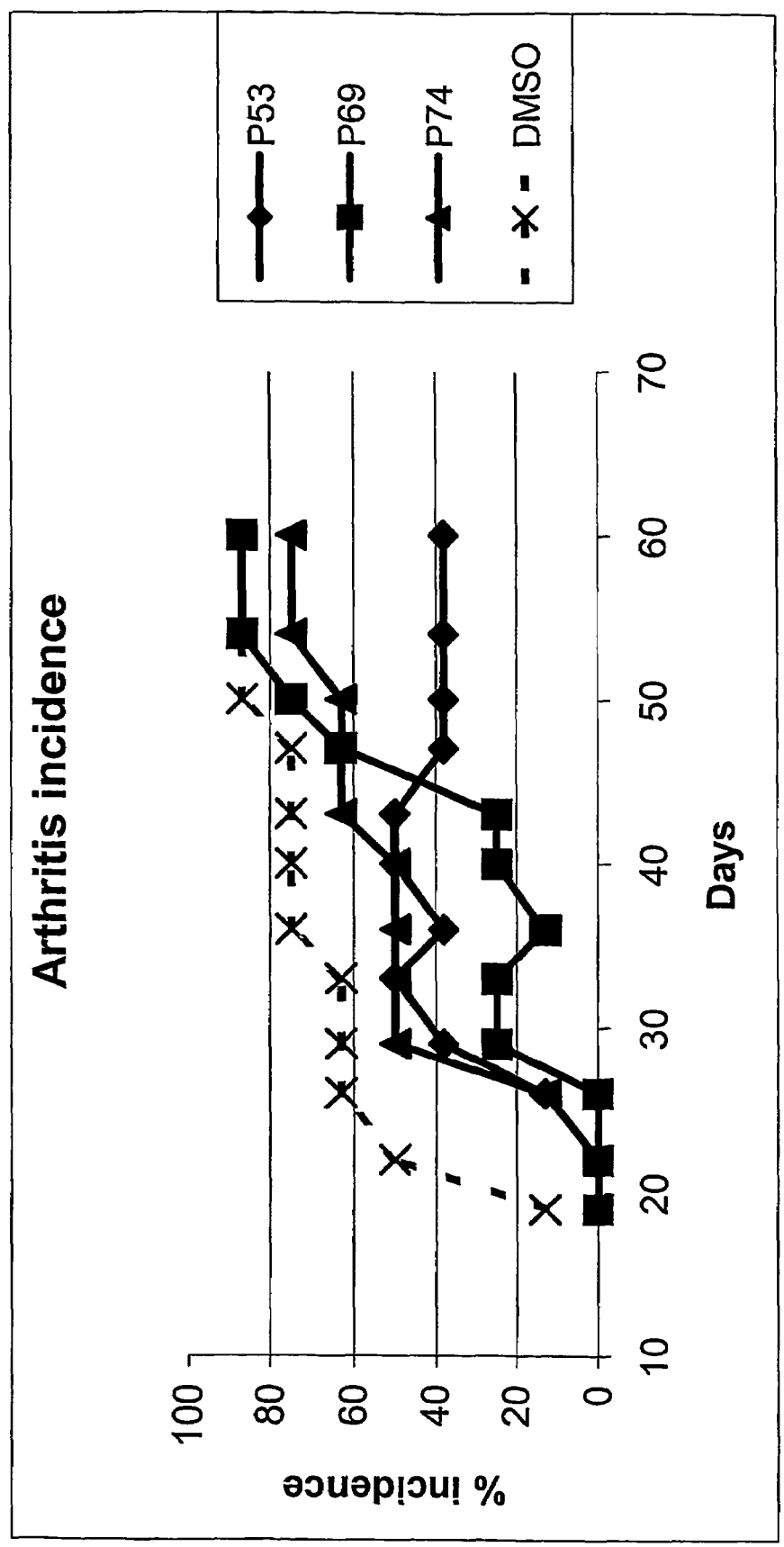
FIG. 16 Efficacy of preferred tetramer and heptamer compounds of the invention (P69, P53 and P74) in the CIA mouse model for rheumatoid arthritis compared to solvent as control.

Disease Severity Score
1. Erythema and mild swelling confined to the tarsals or ankle joint
2. Erythema and mild swelling extending from the ankle to the tarsals
3. Erythema and moderate swelling extending from the ankle to the metatarsal joints
4. Erythema and severe swelling encompass the ankle, foot, and digits FIG. 16 shows the efficacy of preferred compounds of the invention (P96, P53 and P74) in the CIA mouse model for rheumatoid arthritis compared to solvent as control.

EAE is induced in DR4 transgenic mice by injection of myelin oligodendrocyte glycoprotein (MOG) as described by Ito et al. (1996). After disease onset, mice are treated with compounds and studied as below:

| Day | Treatment |
| --- | --- |
| 0 | Immunization (MOG + CFA) |
| 14-36 | Compound injected s.c. starting at disease induction or onset 5× per week |

Figure 17:
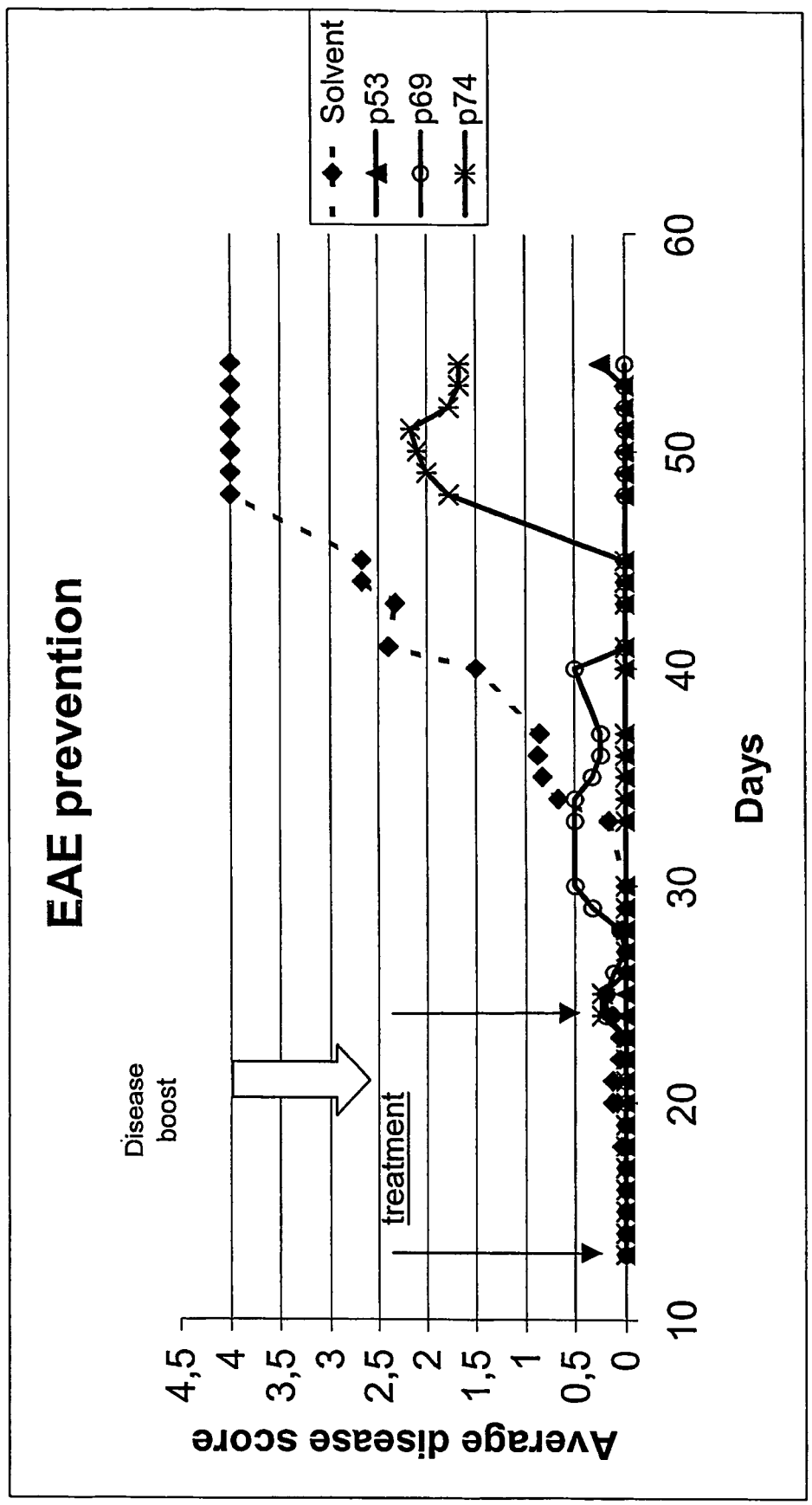
FIG. 17 Efficacy of preferred tetramer and heptamer compounds of the invention (P69, P53 and P74) in the EAE mouse model for multiple sclerosis prevention compared to solvent as control.

Disease Score
1. Tail atony
2. Hind limb weakness
3. Hind limb paralysis
4. Hind limb paralysis and fore limb weakness or paralysis
5. Moribund FIG. 17 shows the efficacy of preferred compounds of the invention (P69, P53 and P74) in the EAE mouse model for multiple sclerosis prevention compared to solvent as control.

Figure 18:
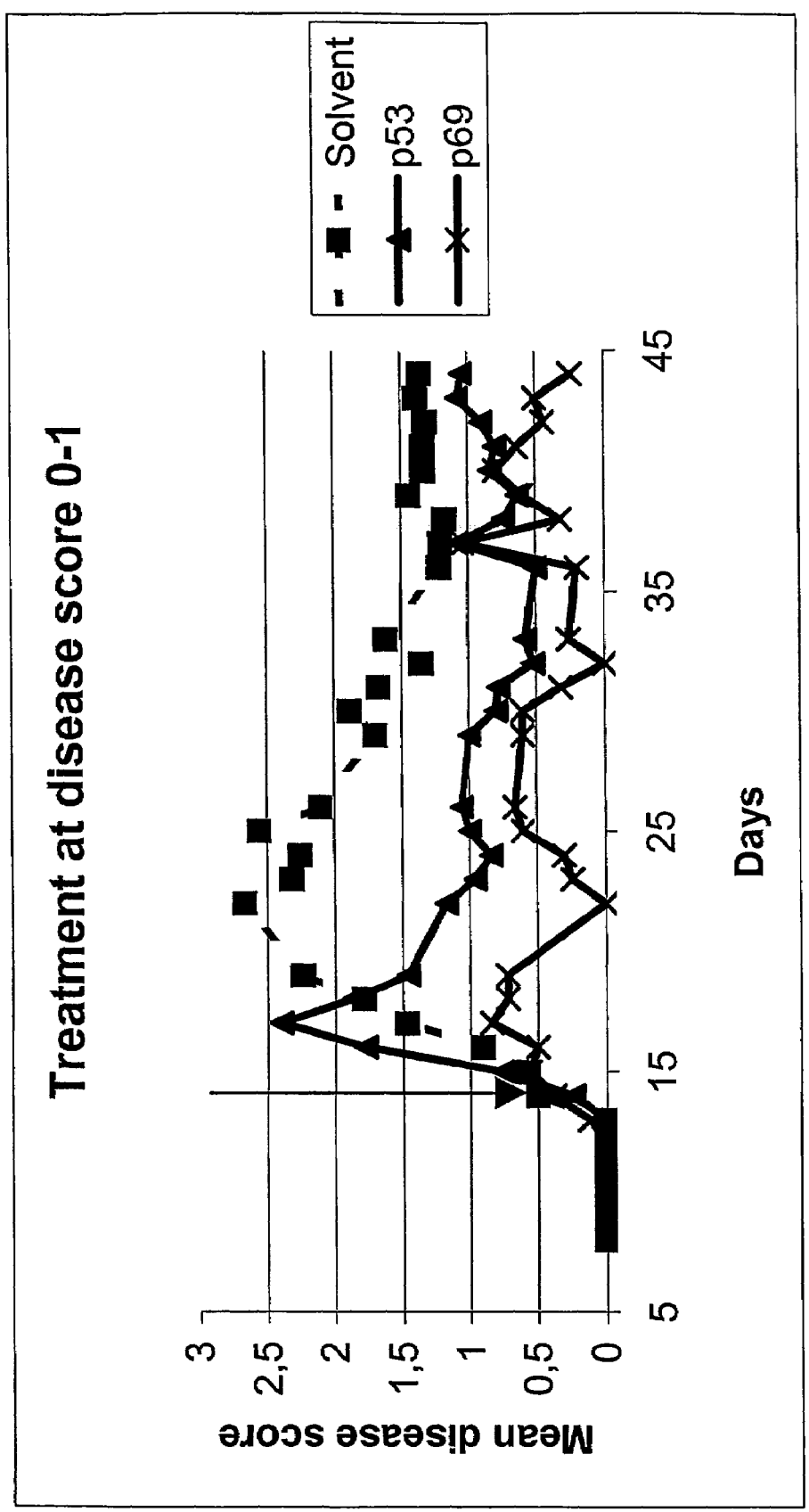
FIG. 18 Efficacy of preferred tetramer and heptamer compounds of the invention (P69 and P53) in the EAE mouse model for multiple sclerosis treatment compared to solvent as control.

FIG. 18 shows the efficacy of preferred compounds of the invention (P69 and P53) in the EAE mouse model for multiple sclerosis treatment compared to solvent as control.

Figure 19:
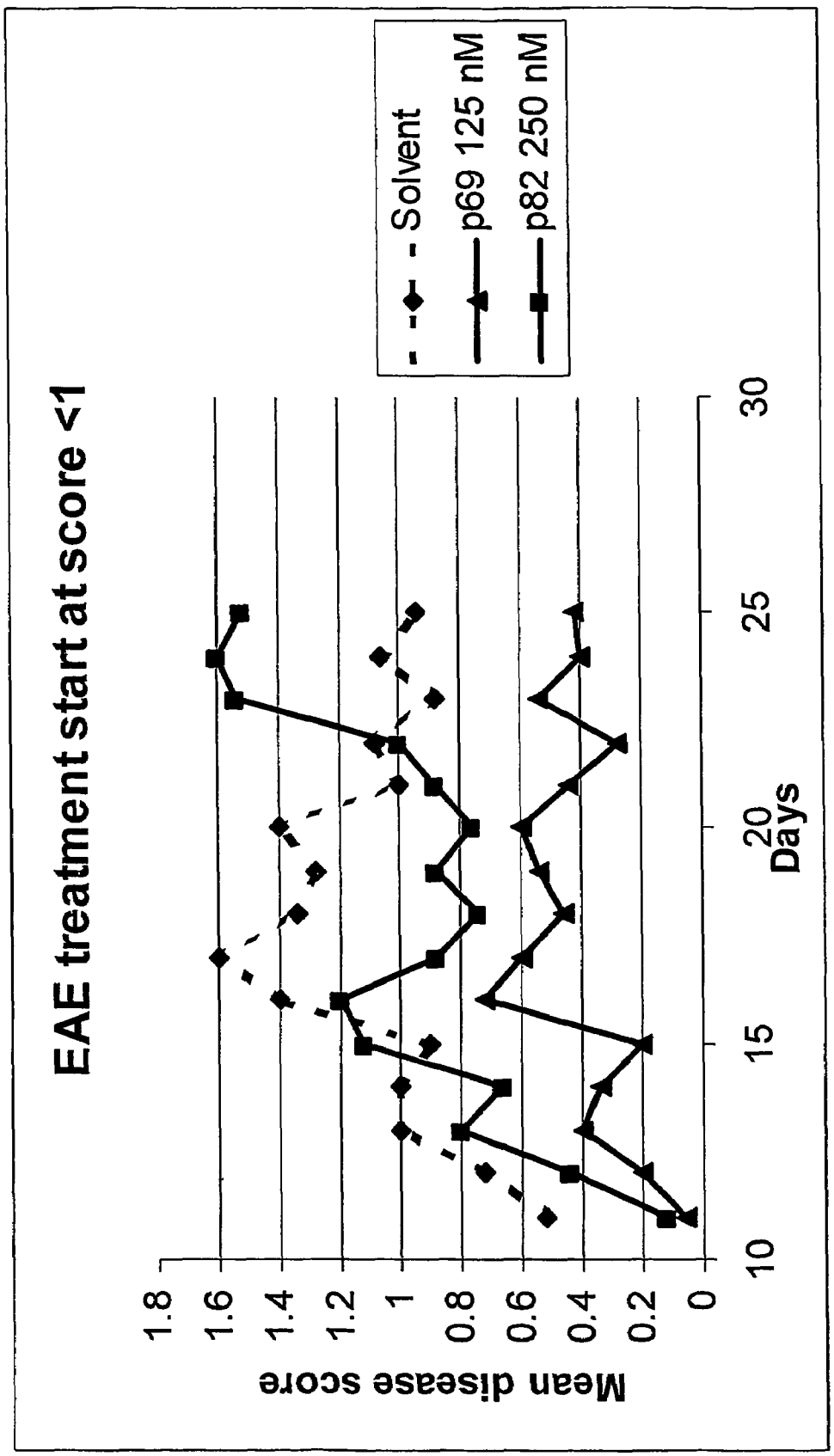
FIG. 19 Superior efficacy of a preferred Gpc-containing compound of the invention (P69) compared to the equivilent Arg containing compound (P82) in the EAE mouse model of multiple sclerosis.

FIG. 19 shows the efficacy of a preferred Gpc-containing compound of the invention (P69) compared to equivilent Arg containing compound (P82) in the EAE mouse model of multiple sclerosis. The efficacy of the Gpg compound is superior in terms of disease treatment than the Arg compound, despite being treated at half concentration (125 nM) of the Arg compound (250 nM).

Example 22

Pharmaceutical Compositions

In order to select the most appropriate compound of the invention to enter further experiments and to assess its suitability for use in a therapeutic composition for the treatment of diseases of the immune system, additional data are collected. Such data for each compund can include the affinity, reactivity, specificity, IC50-values, for inhibition of IL-2 secretion and of T-cell proliferation, as estimated in vitro, and DR-transgenic models of rheumatoid arthritis, and multiple sclerosis.

The activity of compounds of the invention may be compared against previously accepted therapies or theraputics for a given disorder. For example, a particular compound of the invention may be compared against Interferon-beta, an accepted therapy for multiple sclerosis.

The compound that shows appropriate affinity, best specificity and/or greatest inhibition of T-cell proliferation or IL-2 secretion, and high efficacy in inhibiting rheumatoid arthritis, and multiple sclerosis in appropriate models, might be chosen to enter further experiments. Such experiments may include, for example, therapeutic profiling and toxicology in animals and phase I clinical trials in humans.

The compounds of the invention may be administered for therapeutic or prophylactic use to warm-blooded animals such as humans in the form of conventional pharmaceutical compositions, a typical example of which includes the following: Injectable Solution: 0.01 to 100 mg of active ingredient is dissolved in up to 2 mL of an aqueous injection vehicle to give a concentration of active ingredient between 0.01 to 100 mg/mL. The aqueous injection vehicle is buffered to a pH between 5 and 8, as needed, using a pharmaceutically acceptable buffer (for example, phosphate or acetate) and contains a pharmaceutically acceptable tonicity adjustment agent (for example, NaCl or dextrose) added to achieve isotonicity. The vehicle may optionally also contain other pharmaceutically acceptable excipients such as solubilizing agents (for example, DMSO, ethanol, propylene glycol, polyethylene glycol, etc.) preservatives, and antioxidants. The active ingredient may typically be a compound described hereinabove and may conveniently be present as a pharmaceutically acceptable salt. The compound of the invention may be administered together with one or more other active ingredients. Such compositions may be a single package, pill, or application containing several such active ingredients, or such administration may comprise sequential or repeated administrations of the separate active ingredients that include a compound of the invention.

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims.

All patents, published patent applications, and publications cited herein are incorporated by reference as though set forth fully herein.

TABLE 1

Gpg-containing compounds of the invention

| # | Pos. 2 | Sequence |
|---|---|---|
| a. Preferred Gpg-containing compounds of the invention. | | |
| P41-1 | Gpg | Ac-Cha-Gpg-Disc-Met-βPhPro-[S(oxaz)L]-NMe2 |
| P41-2 | Gpg | Ac-Cha-Gpg-Disc-Met-βPhPro-[S(oxaz)L]-NMe2 |
| P45-1 | Gpg | Ac-Cha-Gpg-Disc-Met-βPhPro-OH |
| P45-2 | Gpg | Ac-Cha-Gpg-Disc-Met-βPhPro-OH |
| P47 | Gpg | Ac-Cha-Gpg-Tic-Met(O)-βPhPro-[S(oxaz)L]-NMe2 |
| P52 | Gpg | Ac-Phe-Gpg-Tic-Met(O)-βPhPro-[S(oxaz)L]-NMe2 |
| P53 | Gpg | Ac-Cha-Gpg-Tic-Nle-βPhPro-[S(oxaz)L]-NMe2 |
| P54 | Gpg | Ac-Cha-Gpg-Tic-Nle-βPhPro-N(Me)CH2CH2OH |
| P55 | Gpg | Ac-Phe-Gpg-Tic-Nle-βPhPro-[S(oxaz)L]-NMe2 |
| P56 | Gpg | Ac-Phe-Gpg-Tic-Nle-βPhPro-N(Me)CH2CH2OH |
| P57 | Gpg | Ac-Hfe-Gpg-Tic-Nle-βPhPro-[S(oxaz)L]-NMe2 |
| P58 | Gpg | Ac-Thi-Gpg-Tic-Nle-βPhPro-[S(oxaz)L]-NMe2 |
| P59 | Gpg | Ac-Cha-Gpg-Tic-Ile-βPhPro-[S(oxaz)L]-NMe2 |
| P60 | Gpg | Ac-Cha-Gpg-Tic-Met-βPhPro-[S(oxaz)L]-NMe2 |
| P61-1 | Gpg | Ac-Cha-Gpg-Disc-Nle-βPhPro-[S(oxaz)L]-NMe2 |
| P61-2 | Gpg | Ac-Cha-Gpg-Disc-Nle-βPhPro-[S(oxaz)L]-NMe2 |
| P62-1 | Gpg | Ac-Phe-Gpg-Disc-Met-βPhPro-[S(oxaz)L]-NMe2 |
| P62-2 | Gpg | Ac-Phe-Gpg-Disc-Met-βPhPro-[S(oxaz)L]-NMe2 |
| P63-1 | Gpg | Ac-Thi-Gpg-Disc-Met-βPhPro-[S(oxaz)L]-NMe2 |
| P63-2 | Gpg | Ac-Thi-Gpg-Disc-Met-βPhPro-[S(oxaz)L]-NMe2 |
| P64 | Gpg | Ac-Cha-Gpg-Disc-Met(O)-βPhPro-[S(oxaz)L]-NMe2 |
| P65 | Gpg | Ac-Thi-Gpg-Disc-Met(O)-βPhPro-[S(oxaz)L]-NMe2 |
| P66-1 | Gpg | Ac-Cha-Gpg-Disc-Met-NH2 |
| P66-2 | Gpg | Ac-Cha-Gpg-Disc-Met-NH2 |
| P67 | Gpg | Ac-Cha-Gpg-Tic-Met-NH2 |
| P68 | Gpg | Ac-Cha-Gpg-Tic-Nle-N(H)Bn |
| P69 | Gpg | Ac-Cha-Gpg-Tic-Nle-N(H)CH2CH2Ph |
| P70 | Gpg | Ac-Cha-Gpg-Tic-Nle-N(H)CH2CH2OCH2CH2OH |
| P74 | Gpg | Ac-Cha-Gpg-Tic-Nle-N(Me)Bn |
| P76-1 | Gpg | Ac-Cha-Gpg-Disc-Nle-N(Me)Bn |
| P76-2 | Gpg | Ac-Cha-Gpg-Disc-Nle-N(Me)Bn |
| P77 | Gpg | Ac-Cha-Gpg-Tic-Nle-tetrahydroisoquinoline |
| P78 | Gpg | Ac-Cha-Gpg-Tic-Nle-N(Bn)CH2CH2OH |
| P80 | Gpg | Ac-Cha-Gpg-Tic-Met-βPhProNH2 |

TABLE 1-continued

Gpg-containing compounds of the invention

| | | |
|---|---|---|
| P101 | Gpg | Ac-Cha-Gpg-Tic-Nle-N(Bn)CH2CH2OCH2CH2OH |
| P102 | Gpg | Ac-Cha-Gpg-Tic-Met-N(Bn)CH2CH2OCH2CH2OH |

Prefered substitutions
Lead peptide

| Ac | (Cha) | R | A | M | A | S | L | —NH$_2$ |
|---|---|---|---|---|---|---|---|---| b. Preferred mimetic substitutions of the lead natural peptide (Falcioni et al; 1999) according to Formula II.

| Ac | Cha | Gpg | Ala | Met | Ala | Ser | Leu | —NH$_2$ |
|---|---|---|---|---|---|---|---|---|
| 4-aminobutyryl | Nba | | C(Acm) | Nle | β-PhPro | | tLeu | |
| 3-aminopropyl | 4-MeCha | | C(Prm) | Chg | | --------N(H)CH(CH$_2$OH)$_2$-------- | | |
| | Coa | | MePhg | ---Haic--- | | --------N(CH$_3$)CH$_2$CH$_2$OH-------- | | |
| | Hfe | | C(Ac) | --Odapdc-- | | ---------N(H)CH$_2$CH$_2$OH--------- | | |
| | Phe | | Nva | Met(O) | | ----[S-Ψ(oxaz)-L]-N(CH$_3$)$_2$----- | | |
| | | | Tic | Ile | | ----[S-Ψ(imid)-L]-N(CH$_3$)$_2$----- | | |
| | | | Disc | | | ----------N(H)CH$_2$tBu---------- | | |
| | | | Thiq | | | ----------D-Leu-ol---------- | | |
| | | | azaTic | | | ----------D-Leu-ol---------- | | |
| | | | | | | ------------N(H)Bn------------ | | |
| | | | | | | ----------N(CH3)Bn----------- | | |
| | | | | | | ---------N(H)CH2CH2Ph--------- | | |
| | | | | | | --------N(CH3)CH2CH2Ph-------- | | |
| | | | | | | --------N(CH3)CH2CH2OH-------- | | |
| | | | | | | --------N(Bn)CH2CH2OH-------- | | |
| | | | | | | ------N(CH2CH2Ph)CH2CH2OH----- | | |
| | | | | | | -----N(H)CH2CH2OCH2CH2OH------ | | |
| | | | | | | -----N(Bn)CH2CH2OCH2CH2OH----- | | |
| | | | | | | --N(CH2CH2Ph)CH2CH2OCH2CH2OH-- | | |
| | | | | | | ----tetrahydroisoquinoline---- | | |
| | | | | | | ----------isoindoline--------- | | |

Prefered substitutions
Lead peptide

| Ac | (Cha) | R | A | M | A | S | L | —NH$_2$ |
|---|---|---|---|---|---|---|---|---| c. Preferred tetramer mimetic substitutions of the lead natural peptide (Falcioni et al; 1999) according to Formula I.

| Ac | Cha | Gpg | Ala | Met | | | | |
|---|---|---|---|---|---|---|---|---|
| Ac | Cha | Gpg | Ala | Met | ----------------N(H)Bn---------------- | | | |
| 4-aminobutyryl | Nba | Arg | C(Acm) | Nle | ---------------N(CH$_3$)Bn--------------- | | | |
| 3-aminopropyl | 4-MeCha | Orn | C(Prm) | Chg | -------------N(H)CH$_2$CH$_2$Ph-------------- | | | |
| | Coa | 4-Pya | MePhg | Ile | ------------N(CH$_3$)CH$_2$CH$_2$Ph------------- | | | |
| | Hfe | αMeOrn | C(Ac) | Met(O) | -------------N(CH$_3$)CH$_2$CH$_2$OH------------- | | | |
| | Phe | Cit | Nva | | -------------N(Bn)CH$_2$CH$_2$OH-------------- | | | |

TABLE 1-continued

Gpg-containing compounds of the invention

| | | |
|---|---|---|
| alle | Tic | ----------N(CH$_2$CH$_2$Ph)CH$_2$CH$_2$OH---------- |
| Val | Disc | ----------N(H)CH$_2$CH$_2$OCH$_2$CH$_2$OH---------- |
| 3-Pya | Thiq | ---------N(Bn)CH$_2$CH$_2$OCH$_2$CH$_2$OH---------- |
| ---Odapdc--- | | --------N(CH$_2$CH$_2$Ph)CH$_2$CH$_2$OCH$_2$CH$_2$OH-------- |
| | azaTic | ---------tetrahydroisoquinoline--------- |
| | | -------------isoindoline--------------- |

TABLE 2

Other compounds investigated with the assays described herein

| # | Pos. 2 | Sequence |
|---|---|---|
| | Arg | Ac-Cha-Arg-Tic-Haic-[S(oxaz)L]-N(CH3)2 |
| | Arg | Ac-Cha-Arg-Tic-Haic-NH2 |
| | Arg | Ac-Cha-Arg-Tic-Haic-Ser-MeLeu-NH2 |
| | Arg | Ac-Cha-Arg-Tic-Met-βPhPro-Ser-tLeu-NH2 |
| P1 | Arg | Ac-Cha-Arg-Tic-Met-NH2 |
| P3 | Arg | Ac-Cha-RAMASL-NH2 |
| P6 | Arg | Ac-Cha-Arg-Thiq-Met-NH2 |
| P8 | Orn | Ac-Cha-Orn-Tic-Met-NH2 |
| P9 | Orn | Ac-Cha-Orn-Thiq-Met-NH2 |
| P10 | Val | Ac-Cha-Val-Tic-Met-NH2 |
| P11 | Val | Ac-Cha-Val-Thiq-Met-NH2 |
| P12-1 | Arg | Ac-Cha-Arg-Disc-Met-NH2 |
| P12-2 | Arg | Ac-Cha-Arg-Disc-Met-NH2 |
| P13 | alle | Ac-Cha-alle-Tic-Met-NH2 |
| P14 | alle | Ac-Cha-alle-Thiq-Met-NH2 |
| P15-1 | Val | Ac-Cha-Val-Disc-Met-NH2 |
| P15-2 | Val | Ac-Cha-Val-Disc-Met-NH2 |
| P16-1 | Orn | Ac-Cha-Orn-Disc-Met-NH2 |
| P16-2 | Orn | Ac-Cha-Orn-Disc-Met-NH2 |
| P17-1 | alle | Ac-Cha-alle-Disc-Met-NH2 |
| P17-2 | alle | Ac-Cha-alle-Disc-Met-NH2 |
| P18-1 | Orn | Ac-Cha-Orn-azaTic-Met(O)-NH2 |
| P18-2 | Orn | Ac-Cha-Orn-azaTic-Met-NH2 |
| P20 | Arg | Ac-Cha-Arg-azaTic-Met-NH2 |
| P21 | Arg | Ac-Cha-Arg-D-Tic-Met-NH2 |
| P22 | Cit | Ac-Cha-Cit-Disc-Met-NH2 |
| P24 | Cit | Ac-Cha-Cit-D-Tic-Met-NH2 |
| P25 | Cit | Ac-Cha-Cit-Tic-Met-NH2 |

TABLE 2-continued

Other compounds investigated with the assays described herein

| # | Pos. 2 | Sequence |
|---|---|---|
| P26 | Orn | Ac-Cha-Orn-D-Tic-Met-NH2 |
| P28 | "Arg" | Ac-YGRKKRRQRRR-(ACS)Cha-R-Tic-M-NH2 |
| P30 | Arg | Ac-Cha-Arg-Tic-Met-βPhPro-OH |
| P31 | Arg | Ac-Cha-Arg-Tic-Met-βPhPro-NH2 |
| P32 | 3Pya | Ac-Cha-3Pya-Tic-Met-NH2 |
| P33 | Arg | Ac-Cha-Arg-Tic-Met-βPhPro-[S(oxaz)L]-NMe2 |
| P34 | 4Pya | Ac-Cha-4Pya-Tic-Met-NH2 |
| P35-1 | aMeOrn | Ac-Cha-αMeOrn-Tic-Met-NH2 |
| P35-2 | aMeOrn | Ac-Cha-αMeOrn-Tic-Met-NH2 |
| P36 | Arg | Ac-Cha-Arg-(N,N'-Et2)-Tic-Met-NH2 |
| P38-2 | Arg | Ac-Cha-Arg-(Et2)-Disc-Met-NH2 |
| P39 | Orn | Ac-Cha-Orn-Tic-Met-βPhPro-[S(oxaz)L]NMe2 |
| P40-1 | Arg | Ac-Cha-Arg-Disc-Met-βPhPro-[S(oxaz)L]NMe2 |
| P40-2 | Arg | Ac-Cha-Arg-Disc-Met-βPhPro-[S(oxaz)L]-NMe2 |
| P42 | Arg | H-Cha-Arg-Tic-Met-NH2 |
| P43 | Arg | Ac-Cha-Arg-Tic-Met(O)-βPhPro-[S(oxaz)L]-NMe2 |
| P44-1 | Arg | Ac-Cha-Arg-Disc-Met-βPhPro-N(Me)CH2CH2OH |
| P44-2 | Arg | Ac-Cha-Arg-Disc-Met-βPhPro-N(Me)CH2CH2OH |
| P48 | N/A | O,O'-Bis-(CH2-CH2-NH-CO-Cha-Arg-Tic-Met-NH2)-PEG 3400 |
| P49 | Arg | Ac-Phe-Arg-Tic-Met-NH2 |
| P50 | Arg | Ac-Cha-Arg-Tic-Ile-NH2 |
| P51 | Arg | Ac-Cha-Arg-Tic-Nle-βPhPro-[S(oxaz)L]-NMe2 |
| P71 | Arg | Ac-Cha-Arg-Tic-Nle-N(Me)Bn |
| P72-1 | Arg | Ac-Cha-Arg-Disc-Nle-N(Me)Bn |
| P72-2 | Arg | Ac-Cha-Arg-Disc-Nle-N(Me)Bn |
| P73 | Arg | H-Cha-Arg-Tic-Nle-NMe2 |
| P75-1 | Arg | Ac-Cha-Arg-Hbc-Nle-N(Me)Bn |
| P75-2 | Arg | Ac-Cha-Arg-Hbc-Nle-N(Me)Bn |
| P79 | Arg | Ac-Cha-Arg-Phe-Nle-N(Me)Bn |
| P81 | Arg | Ac-Cha-Arg-Tic-Nle-N(CH2CH2OH)CH2CH2Ph |
| P82 | Arg | Ac-Cha-Arg-Tic-Nle-N(H)CH2CH2Ph |
| P83 | Arg | Ac-Cha-Arg-Tic-Nle-N(Me)CH2CH2Ph |
| P84 | Arg | Ac-Cha-Arg-Tic-Met-N(Me)CH2CH2Ph |
| P85 | Arg | Ac-Cha-Arg-Tic-Met-N(CH2CH2OH)CH2CH2Ph |
| P86 | Arg | Ac-Cha-Arg-Tic-Nle-N(CH2CH2Ph)CH2CH2OCH2CH2OH |
| P89 | Arg | Ac-Cha-Arg-Tic-NBu2 |
| P90 | Arg | Ac-Cha-Arg-Tic-Gly-N(Me)Bn |

TABLE 2-continued

Other compounds investigated with the assays described herein

| # | Pos. 2 | Sequence |
|---|---|---|
| P91 | Arg | Ac-Cha-Arg-Tic-Aib-N(Me)Bn |
| P92 | Arg | Ac-Cha-Arg-Tic-Nle-N(Me)CH2CH2OH |
| P93 | Arg | Z-Cha-Arg-N(Me)Bn |
| P94 | Arg | Ac-Cha-Arg-Tic-Aib-N(Bn)CH2CH2OH |
| P95 | Arg | Ac-Cha-Arg-Tic-Gly-N(Bn)CH2CH2OH |
| P96 | Arg | Ac-Cha-Arg-Tic-Met-N(CH2CH2Ph)CH2CH2OCH2CH2OH |
| P97 | Arg | Ac-Cha-Arg-Tic-N(H)Bu |
| P98 | Arg | Ac-Cha-Arg-Tic-Nle-N(Bn)CH2CH2OCH2CH2OH |
| P99 | Arg | Ac-Cha-Arg-Tic-Met-N(Bn)CH2CH2OCH2CH2OH |
| P100 | Arg | Ac-Cha-Arg-Tic-NH(C5H11) |

TABLE 3 a. Biological properties of certain compounds of the invention with reference to Formula II

| | | | Protein binding IC50 (nM) | | | Cell binding IC50 (uM) | |
|---|---|---|---|---|---|---|---|
| Number | Pos. 2 | Sequence | 0401 | 0101 | 0404 | Priess (0401) | LG2 (0101) |
| P33 | Arg | Ac-Cha-Arg-Tic-Met-βPhPro-[SΨ(oxaz)L]-NMe$_2$ | 300 | 190 | 220 | 3.2 | 4.6 |
| P60 | Gpg | Ac-Cha-Gpg-Tic-Met-βPhPro-[SΨ(oxaz)L]-NMe$_2$ | 230 | 250 | 190 | 2.1 | 1.5 |
| P51 | Arg | Ac-Cha-Arg-Tic-Nle-βPhPro-[SΨ(oxaz)L]-NMe$_2$ | 670 | 400 | 210 | NT | 3 |
| P53 | Gpg | Ac-Cha-Gpg-Tic-Nle-βPhPro-[SΨ(oxaz)L]-NMe$_2$ | 410 | 340 | 180 | 3 | 3.5 |
| P43 | Arg | Ac-Cha-Arg-Tic-Met(O)-βPhPro-[SΨ(oxaz)L]-NMe$_2$ | 320 | 380 | 1,700 | 3.1 | 13 |
| P47 | Gpg | Ac-Cha-Gpg-Tic-Met(O)-βPhPro-[SΨ(oxaz)L]-NMe$_2$ | 180 | 330 | 580 | 6.9 | 4.6 |
| P40-1 | Arg | Ac-Cha-Arg-Disc-Met-βPhPro-[SΨ(oxaz)L]-NMe$_2$ | 270 | 140 | 98 | 3 | 8 |
| P41-1 | Gpg | Ac-Cha-Gpg-Disc-Met-βPhPro-[SΨ(oxaz)L]-NMe$_2$ | 200 | 160 | 110 | 3.7 | 3.8 |
| P82 | Arg | Ac-Cha-Arg-Tic-Nle-N(H)CH$_2$CH$_2$Ph | 18,000 | 3,100 | 14,000 | NT | NT |
| P69 | Gpg | Ac-Cha-Gpg-Tic-Nle-N(H)CH$_2$CH$_2$Ph | 3,600 | 690 | 4,500 | 11 | 8.2 |
| P12-1 | Arg | Ac-Cha-Arg-Disc-Met-NH$_2$ | 370 | 430 | 860 | 6.7 | 9.6 |
| P66-1 | Gpg | Ac-Cha-Gpg-Disc-Met-NH$_2$ | 290 | 290 | 590 | 7.8 | 6 |
| P72-1 | Arg | Ac-Cha-Arg-Disc-Nle-N(Me)Bn | 5,200 | 1,200 | 1,700 | 7.5 | 12 |
| P76-1 | Gpg | Ac-Cha-Gpg-Disc-Nle-N(Me)Bn | 2,300 | 550 | 1,400 | 9.8 | 4.6 |
| P1 | Arg | Ac-Cha-Arg-Tic-Met-NH$_2$ | 1,600 | 260 | 2,300 | 11 | 6.8 |
| P67 | Gpg | Ac-Cha-Gpg-Tic-Met-NH$_2$ | 410 | 120 | 1,060 | 4.5 | 4.5 |
| P71 | Arg | Ac-Cha-Arg-Tic-Nle-N(Me)Bn | 11,000 | 860 | 6,600 | 11 | 6.9 |
| P74 | Gpg | Ac-Cha-Gpg-Tic-Nle-N(Me)Bn | 3,400 | 360 | 2,200 | 9.2 | 6.1 |
| P31 | Arg | Ac-Cha-Arg-Tic-Met-βPhPro-NH$_2$ | 280 | 290 | 850 | 3.7 | 8.5 |
| P80 | Gpg | Ac-Cha-Gpg-Tic-Met-βPhProNH$_2$ | 670 | 550 | 470 | 2.7 | 2.7 |
| P98 | Arg | Ac-Cha-Arg-Tic-Nle-N(Bn)CH$_2$CH$_2$OCH$_2$CH$_2$OH | 4,700 | 640 | 1,300 | NT | NT |
| P101 | Gpg | Ac-Cha-Gpg-Tic-Nle-N(Bn)CH$_2$CH$_2$OCH$_2$CH$_2$OH | 1,500 | 500 | 650 | NT | NT |
| P99 | Arg | Ac-Cha-Arg-Tic-Met-N(Bn)CH2CH2OCH2CH2OH | 3,000 | 560 | 1,900 | NT | NT |
| P102 | Gpg | Ac-Cha-Gpg-Tic-Met-N(Bn)CH2CH2OCH2CH2OH | 1,700 | 580 | 2,100 | NT | NT |

| | Immunsupressive assays IC50 (uM) and Max % Inhibition) | | | | | | Stability (Arbitrary units) Rat, Mouse or Human plasma; Cathepsins | |
|---|---|---|---|---|---|---|---|---|
| Number | DR4-LN (IC50) | DR4-LN (Max) | DR14-LN (IC50) | DR14-LN (Max) | Thyb1 (IC50) | Thyb1 (Max) | Rat 6 h | Rat 24 h |
| P33 | NT | NT | NT | NT | 28 | 91 | 78 | 40 |
| P60 | 29 | 97 | 41 | 98 | 30 | 47 | 134 | 124 |
| P51 | 36 | 100 | 52 | 99 | 62 | 88 | 81 | 60 |
| P53 | 40 | 100 | 32 | 101 | 25 | 99 | 114 | 108 |
| P43 | NT | NT | NT | NT | 54 | 84 | 96 | 71 |
| P47 | 77 | 77 | NT | NT | 62 | 83 | 116 | 103 |
| P40-1 | NT | NT | NT | NT | 59 | 81 | 111 | 71 |
| P41-1 | 49 | 96 | 25 | 98 | 47 | 83 | 91 | 103 |
| P82 | 27 | 100 | NT | NT | 78 | 100 | 65 | 18 |
| P69 | 19 | 101 | 23 | 107 | 42 | 96 | 41 | 42 |
| P12-1 | >200 | 5 | NT | NT | NT | NT | 67 | 10 |
| P66-1 | 120 | 20 | NT | NT | 100 | 24 | 138 | 81 |

TABLE 3-continued

| Number | | | | | | | |
|---|---|---|---|---|---|---|---|
| P72-1 | 31 | 103 | 29 | 95 | 88 | 105 | 80 | 67 |
| P76-1 | 34 | 103 | NT | NT | 64 | 106 | 80 | 84 |
| P1 | 84 | 41 | NT | NT | >200 | NM | 11 | 0 |
| P67 | NT | NT | NT | NT | 115 | 33 | 10 | 34 |
| P71 | 19 | 102 | 15 | 96 | 78 | 101 | 89 | 53 |
| P74 | 18 | 102 | 14 | 97 | 47 | 103 | 91 | 71 |
| P31 | 18 | 64 | 98 | 89 | 55 | 64 | 42 | 5 |
| P80 | NT | NT | 94 | 88 | 13 | 100 | 102 | 39 |
| P98 | 69 | 67 | >200 | NM | 79 | 86 | 71 | 60 |
| P101 | 66 | 100 | 46 | 100 | 57 | 88 | 73 | 81 |
| P99 | 120 | 50 | 105 | 100 | 97 | 62 | 80 | 62 |
| P102 | 110 | 60 | 73 | 100 | 81 | 76 | 131 | 121 |

| | Stability (Arbitrary units) Rat, Mouse or Human plasma; Cathepsins | | | | | | |
|---|---|---|---|---|---|---|---|
| Number | Human 6 h | Human 24 h | Mouse 6 h | Mouse 24 h | Cath B 4 h | Cath D 4 h | Cath L 4 h |
| P33 | 97 | 94 | 97 | 69 | 98 | 97 | 107 |
| P60 | 88 | 120 | 111 | 95 | 98 | 108 | NT |
| P51 | 119 | 129 | 118 | 136 | 103 | 103 | NT |
| P53 | 110 | 122 | 117 | 115 | 97 | 99 | NT |
| P43 | 134 | 131 | 96 | 82 | 96 | 101 | NT |
| P47 | 126 | 140 | 126 | 111 | 100 | 99 | NT |
| P40-1 | 108 | 103 | NT | NT | 99 | 93 | NT |
| P41-1 | 59 | 115 | 100 | 111 | 104 | 103 | NT |
| P82 | 94 | 72 | 79 | 31 | 105 | 106 | NT |
| P69 | 105 | 93 | 115 | 85 | 92 | 100 | NT |
| P12-1 | 75 | 0 | 76 | 38 | 96 | 103 | 101 |
| P66-1 | 103 | 87 | 115 | 112 | 102 | 101 | NT |
| P72-1 | 99 | 99 | 97 | 75 | 98 | 101 | NT |
| P76-1 | 93 | 107 | 93 | 16 | 100 | 104 | NT |
| P1 | 94 | 85 | NT | 5 | 87 | 102 | 117 |
| P67 | 97 | 100 | 71 | 16 | 58 | 113 | NT |
| P71 | 107 | 90 | 117 | 87 | 97 | 104 | NT |
| P74 | 114 | 125 | 146 | 97 | 105 | 104 | NT |
| P31 | 93 | 86 | 86 | 56 | 102 | 95 | 103 |
| P80 | 139 | 134 | 106 | 123 | 90 | 84 | NT |
| P98 | 116 | 121 | 87 | 54 | 104 | 104 | NT |
| P101 | 106 | 107 | 107 | 94 | 100 | 106 | NT |
| P99 | 104 | 98 | 71 | 13 | 106 | 107 | NT |
| P102 | 110 | 116 | 105 | 101 | 116 | 120 | NT | b. Biological properties of certain compounds of the invention with reference to Formula I

| | | | | Protein binding IC50 (nM) | | |
|---|---|---|---|---|---|---|
| Number | Pos. 2 | | Sequence | 0401 | 0101 | 0404 |
| P67 | 4 | NH2 | Ac-Cha-Gpg-Tic-Met-NH$_2$ | 410 | 120 | 1,080 |
| P102 | 4 | N(Bn)CH2CH2OCH2CH2OH | Ac-Cha-Gpg-Tic-Met-N(Bn)CH2CH2OCH2CH2OH | 1,700 | 580 | 2,100 |
| P60 | 7 | NMe2 | Ac-Cha-Gpg-Tic-MetβPhPro-[SΨ(oxaz)L]-NMe$_2$ | 230 | 250 | 190 |
| P1 | 4 | NH2 | Ac-Cha-Arg-Tic-Met-NH$_2$ | 1,600 | 260 | 2,300 |
| P99 | 4 | N(Bn)CH2CH2OCH2CH2OH | Ac-Cha-Arg-Tic-Met-N(Bn)CH2CH2OCH2CH2OH | 3,000 | 690 | 1,900 |
| P85 | 4 | N(CH2CH2OH)CH2CH2Ph | Ac-Cha-Arg-Tic-Met-N(CH2CH2OH)CH2CH2Ph | 13,000 | 1,800 | 31,000 |
| P96 | 4 | N(CH2CH2Ph)CH2CH2OCH2CH2OH | Ac-Cha-Arg-Tic-Met-N(CH2CH2Ph)CH2CH2OCH2CH2OH | 5,900 | 1,000 | 7,400 |
| P84 | 4 | N(Me)CH2CH2Ph | Ac-Cha-Arg-Tic-Met-N(Me)CH2CH2Ph | 7,900 | 900 | 14,000 |
| P33 | 7 | NMe2 | Ac-Cha-Arg-Tic-Met-βPhPro-[SΨ(oxaz)L]-NMe$_2$ | 300 | 190 | 220 |
| P69 | 4 | N(H)CH2CH2Ph | Ac-Cha-Gpg-Tic-Nle-N(H)CH$_2$CH$_2$Ph | 3,600 | 690 | 4,500 |
| P101 | 4 | N(Bn)CH2CH2OCH2CH2OH | Ac-Cha-Gpg-Tic-Nle-N(Bn)CH$_2$CH$_2$OCH$_2$CH$_2$OH | 1,500 | 500 | 650 |
| P74 | 4 | N(Me)Bn | Ac-Cha-Gpg-Tic-Nle-N(Me)Bn | 3400 | 360 | 2,200 |
| P78 | 4 | N(Bn)CH2CH2OH | Ac-Cha-Gpg-Tic-Nle-N(Bn)CH2CH2OH | 2,600 | 430 | 1,200 |
| P68 | 4 | N(H)Bn | Ac-Cha-Gpg-Tic-Nle-N(H)Bn | 2,100 | 600 | 2,000 |
| P70 | 4 | N(H)CH2CH2OCH2CH2OH | Ac-Cha-Gpg-Tic-Nle-N(H)CH2CH2OCH2CH2OH | 440 | 90 | 290 |
| P77 | 4 | tetrahydroisoquinoline | Ac-Cha-Gpg-Tic-Nle-tetrahydroisoquinoline | 8,700 | 1,900 | 3,600 |

TABLE 3-continued

| | | | | | | |
|---|---|---|---|---|---|---|
| P53 | 7 | NMe2 | Ac-Cha-Gpg-Tic-Nle-βPhPro-[SΨ(oxaz)L]-NMe₂ | 410 | 340 | 180 |
| P82 | 4 | N(H)CH2CH2Ph | Ac-Cha-Argr-Tic-Nle-N(H)CH₂CH₂Ph | 18,000 | 3,100 | 14,000 |
| P98 | 4 | N(Bn)CH2CH2OCH2CH2OH | Ac-Cha-Arg-Tic-Nle-N(Bn)CH₂CH₂OCH₂CH₂OH | 4,700 | 640 | 1,300 |
| P71 | 4 | N(Me)Bn | Ac-Cha-Arg-Tic-Nle-N(Me)Bn | 11,000 | 880 | 6,600 |
| P81 | 4 | N(CH2CH2OH)CH2CH2Ph | Ac-Cha-Arg-Tic-Nle-N(CH2CH2OH)CH2CH2Ph | 22,000 | 3,300 | 20,000 |
| P88 | 4 | N(CH2CH2Ph)CH2CH2OCH2CH2OH | Ac-Cha-Arg-Tic-Nle-N(CH2CH2Ph)CH2CH2OCH2CH2OH | 10,000 | 2,000 | 5,700 |
| P83 | 4 | N(Me)CH2CH2Ph | Ac-Cha-Arg-Tic-Nle-N(Me)CH2CH2Ph | 24,000 | 1,300 | 11,000 |
| P51 | 7 | NMe2 | Ac-Cha-Arg-Tic-Nle-βPhPro-[SΨ(oxaz)L]-NMe₂ | 670 | 400 | 210 |
| P72-1 | 4 | N(Me)Bn | Ac-Cha-Arg-Disc-Nle-N(Me)Bn | 5,200 | 1,200 | 1,700 |
| P78-1 | 4 | N(Me)Bn | Ac-Cha-Gpg-Disc-Nle-N(Me)Bn | 2,300 | 550 | 1,400 |
| P81-1 | 7 | NMe2 | Ac-Cha-Gpg-Disc-Nle-βPhPro-[S(oxaz)L]-NMe2 | 260 | 220 | 90 |

| | Immunsupresssive assays IC50 (uM) and Max % inhibition) | | | | | | |
|---|---|---|---|---|---|---|---|
| | Cell binding IC50 (uM) | | DR4-LN | DR4-LN | DR14-LN | DR14-LN | Thyb1 | Thyb1 |
| Number | Priess (0401) | LG2 (0101) | (IC50) | (Max) | (IC50) | (Max) | (IC50) | (Max) |
| P67 | 4.5 | 4.5 | NT | NT | NT | NT | 115 | 33 |
| P102 | NT | NT | 110 | 60 | 73 | 100 | 81 | 76 |
| P60 | 2.1 | 1.5 | 29 | 97 | 41 | 98 | 30 | 47 |
| P1 | 11 | 8.8 | 64 | 41 | NT | NT | >200 | NM |
| P99 | NT | NT | 110 | 50 | 105 | 100 | 97 | 62 |
| P85 | NT | NT | NT | NT | NT | NT | 100 | 74 |
| P96 | NT | NT | NT | NT | NT | NT | NT | NT |
| P84 | NT | NT | NT | NT | NT | NT | 97 | 100 |
| P33 | 3.2 | 4.6 | 40 | 100 | 32 | 101 | 25 | 99 |
| P69 | 11 | 6.2 | 19 | 101 | 23 | 107 | 42 | 96 |
| P101 | NT | NT | 69 | 100 | 46 | 100 | 57 | 88 |
| P74 | 9.2 | 6.1 | 16 | 102 | 14 | 97 | 47 | 103 |
| P78 | NT | NT | 36 | 97 | 36 | 100 | 118 | 50 |
| P68 | 12 | 7.2 | 18 | 102 | 17 | 105 | 39 | 106 |
| P70 | 8.6 | 5.7 | 42 | 54 | NT | NT | 83 | 41 |
| P77 | NT | NT | 10 | 100 | 14 | 99 | 73 | 42 |
| P53 | 3 | 3.5 | 40 | 100 | 32 | 101 | 25 | 99 |
| P82 | NT | NT | 27 | 100 | NT | NT | 78 | 100 |
| P98 | NT | NT | 69 | 67 | >200 | NM | 79 | 66 |
| P71 | 11 | 6.9 | 19 | 102 | 15 | 98 | 78 | 101 |
| P81 | NT | NT | NT | NT | NT | NT | 39 | 96 |
| P88 | NT | NT | 105 | 100 | 37 | 100 | 14 | 100 |
| P83 | NT | NT | NT | NT | 13 | 100 | 46 | 100 |
| P51 | NT | 3 | 38 | 100 | 52 | 99 | 62 | 88 |
| P72-1 | 7.5 | 12 | 31 | 103 | 29 | 95 | 88 | 105 |
| P78-1 | 9.8 | 4.6 | 34 | 103 | NT | NT | 64 | 106 |
| P81-1 | 3.4 | 5 | 63 | 99 | 43 | 112 | 32 | 89 |

| | Stability (Arbitrary units) Rat, Mouse or Human plasma; Cathepsins | | | | | | |
|---|---|---|---|---|---|---|---|
| Number | Rat 6 h | Rat 24 h | Human 6 h | Human 24 h | Mouse 6 h | Mouse 24 h | Cath B 4 h | Cath D 4 h |
| P67 | 10 | 34 | 97 | 100 | 71 | 16 | 58 | 113 |
| P102 | 131 | 121 | 110 | 116 | 105 | 101 | 116 | 120 |
| P60 | 134 | 124 | 68 | 120 | 111 | 95 | 88 | 108 |
| P1 | 11 | 0 | 94 | 65 | NT | 5 | 87 | 102 |
| P99 | 80 | 62 | 104 | 96 | 71 | 13 | 106 | 107 |
| P85 | 111 | 71 | NT | 129 | 98 | 57 | 108 | 104 |
| P96 | 83 | 45 | 117 | 64 | 108 | 82 | 91 | 106 |
| P84 | 104 | 99 | 131 | 131 | 111 | 53 | 69 | 101 |
| P33 | 114 | 108 | 110 | 122 | 117 | 185 | 97 | 99 |
| P69 | 41 | 42 | 105 | 93 | 115 | 85 | 92 | 100 |
| P101 | 73 | 81 | 106 | 107 | 107 | 94 | 100 | 106 |
| P74 | 91 | 71 | 114 | 125 | 148 | 97 | 105 | 104 |
| P78 | 184 | 107 | 73 | 130 | 90 | 113 | 100 | 108 |
| P68 | 7 | 0 | 85 | 39 | 49 | 13 | 52 | 105 |
| P70 | 83 | 65 | 116 | 90 | 105 | 82 | 110 | 112 |
| P77 | 129 | 57 | 111 | 114 | 141 | 181 | 107 | 95 |
| P53 | 114 | 108 | 110 | 122 | 117 | 115 | 97 | 99 |
| P82 | 65 | 16 | 94 | 72 | 79 | 31 | 105 | 108 |
| P98 | 71 | 60 | 116 | 121 | 87 | 54 | 104 | 104 |

TABLE 3-continued

| | | | | | | | | |
|---|---|---|---|---|---|---|---|---|
| P71 | 89 | 53 | 107 | 90 | 117 | 67 | 97 | 104 |
| P81 | 88 | 76 | 104 | 109 | 107 | 70 | 99 | 99 |
| P88 | 77 | 55 | 133 | 123 | 125 | 128 | 94 | 101 |
| P83 | 69 | 85 | NT | NT | 93 | 58 | 100 | 98 |
| P51 | 81 | 60 | 119 | 129 | 116 | 136 | 103 | 103 |
| P72-1 | 80 | 67 | 99 | 99 | 97 | 75 | 98 | 101 |
| P78-1 | 80 | 84 | 93 | 107 | 93 | 18 | 100 | 104 |
| P81-1 | 151 | 112 | 151 | 162 | 87 | 84 | 105 | 106 |

TABLE 4

In vivo inhibition by co-immunisation of T cell activation of certain compounds of the invention and certain of their Arg-containing equivilents

| | | % Reduction of response to | | | |
|---|---|---|---|---|---|
| Compound | Pos. 2 | HEL | PPD(HEL) | OVA | PPD(OVA) |
| P51 | Arg | | | 43.1 | 3.5 |
| P53 | Gpg | 68.4 | 10.2 | 56.3 (59) | 26.8 (34.4) |
| P82 | Arg | | | 25 | 5 |
| P69 | Gpg | 59 (88) | 2 (32) | 65.3 (51.7) | 9 (15) |
| P71 | Arg | 78.1 | 62.1 | 48.8 | 21.8 |
| P74 | Gpg | 51.6 (52.6) | 12.8 (3.3) | 42.5 | 5.8 |
| P41-1 | Gpg | | | 50.1 | 21.6 |
| P57 | Gpg | | | 52.6 | 52.4 |
| P60 | Gpg | | | 50.3 | 28.1 |
| P61-1 | Gpg | 37.9 | 32.3 | 3.7 | 29.9 |
| P68 | Gpg | −3.2 | 25.1 | 95.3 | 65.9 |
| P70 | Gpg | | | 56.1 | 52.3 |
| P101 | Gpg | 49.7 (31.7) | 41.1 (21.8) | | |
| P102 | Gpg | 41.3 | 31.2 | | |

The invention claimed is:

1. A compound having a structure of Formula II:

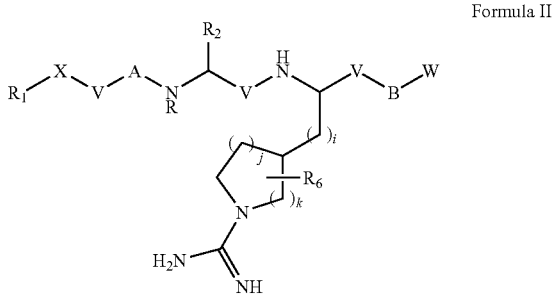

Formula II wherein, as valence and stability permit,

A is absent or represents a sequence of from one to four amino acid or amino acid analog residues;

B represents a sequence of from two to eight amino acid or amino acid analog residues and wherein the N-terminal residues of said sequence are Tic-Nle;

W represents $OR_7$ or $NR_8R_9$;

V is C=O;

X is absent or represents O, S, or NR;

R, independently for each occurrence, represents H or lower alkyl;

$R_1$ represents a substituted or unsubstituted alkyl, heteroalkyl, alkenyl, alkynyl, aryl, aralkyl, heteroaryl, heteroaralkyl, cycloalkyl, cycloalkylalkyl, hetaocyclyl, or heterocyclylalkyl moiety;

$R_2$ represents a substituted or unsubstituted alkyl, heteroalkyl, alkenyl, alkynyl, aryl, aralkyl, heteroaryl, heteroaralkyl, cycloalkyl, cycloalkylalkyl, hetaocyclyl, or heterocyclylalkyl moiety, or $R_2$ and R, taken together, form a ring having from 5 to 7 members, optionally being substituted with from 1 to 5 substituents and/or forming a polycyclic structure with one or more other rings;

i represents an integer from 0-1;

j is 1;

k is 2; and $R_6$ is absent or represents from 1-4 substituents on the nitrogen-containing ring to which it is attached, selected from substituted or unsubstituted lower alkyl, haloalkyl, halogen, hydroxyl, and amino.

$R_7$, $R_8$ and $R_9$ independently represent substituents selected from H and substituted or unsubstituted alkyl, heteroalkyl, aryl, aralkyl, heteroaralkyl, heteroaryl, cycloalkyl, cycloalkylalkyl, hetaocyclyl, and heterocyclylalkyl, or where $R_8$ and $R_9$ taken together, form a ring having from 5 to 7 members, optionally being substituted with from 1 to 5 substituents and/or forming a polycyclic structure with one or more other rings.

2. A compound of claim 1, wherein $R_6$ is absent.

3. A compound of claim 1, wherein at least one of $R_1$, $R_7$, $R_8$, and $R_9$ is a hydrophobic residue.

4. A compound of claim 1, wherein A represents 0 or 1 amino acid or amino acid analog residues.

5. A compound of claim 1, wherein B represents from 2 to 6 amino acid or amino acid analog residues.

6. A compound of claim 1, wherein B represents from 2 to 4 amino acid or amino acid analog residues.

7. A compound of claim 1, wherein the compound has an immunosuppressant activity.

8. A compound of claim 1, wherein the compound inhibits MHC-mediated activation of T cells.

9. A compound of claim 1, wherein the amino acid residues are alpha-amino acid residues.

10. A compound of claim I, wherein $R_1XV$, taken together, represent an acyl group.

11. A compound of claim 10, wherein the acyl group is an alkyl carbonyl group, an aryl carbonyl group, or an aminoalkyl carbonyl group.

12. A compound of claim 10, wherein the acyl group is a beuzoyl group, a lower alkanoyl group, or a lower aminoalkanoyl group.

13. A compound of claim 10, wherein the acyl group is an acetyl group.

14. The compound of claim 1, wherein the compound of formula (II) is selected from the group consisting of:
Ac-Cha-Gpg-Tic-Nle-βPhPro-N(Me)CH$_2$CH$_2$OH;
Ac-Phe-Gpg-Tic-Nle-βPhPro-N(Me)CH$_2$CH$_2$OH;
Ac-Cha-Gpg-Tic-Nle-N(H)Bn;
Ac-Cha-Gpg-Tic-Nle-N(H)CH$_2$CH$_2$Ph;
Ac-Cha-Gpg-Tic-Nle-N(H)CH$_2$CH$_2$OCH$_2$CH$_2$OH;
Ac-Cha-Gpg-Tic-Nle-N(Me)Bn;
Ac-Cha-Gpg-Tic-Nie-tetrahydroisoquinoline;
Ac-Cha-Gpg-Tic-Nle-N(Bn)CH$_2$CH$_2$OH;
Ac-Cha-Gpg-Tic-Nle-N(Bn)CH$_2$CH$_2$OCH$_2$CH$_2$OH;
Ac-Cha-Gpg-Tic-Nle-βPhPro-[Sψ(oxaz)L]-N(CH$_3$)$_2$;
Ac-Phe-Gpg-Tic-Nle-βPhPro-[Sψ(oxaz)L]-N(CH$_3$)$_2$;
Ac-Hfe-Gpg-Tic-Nle-βPhPro-[Sψ(oxaz)L]-N(CH$_3$)$_2$;
Ac-Thi-Gpg-Tic-Nle-βPhPro-[Sψ(oxaz)L]-N(CH$_3$)$_2$; and
X1-aa1-Gpg-Tic-Nle-X2,
wherein:
X1 is Ac, 4-aminobutyryl or 3-aminopropyl;
aa1 is Cha, Nba, 4-MeCha, Coa, Hfe or Phe;
X2 is: -aa2-Ser-aa3-NH$_2$,
-aa2-X3,
—N(H)Bn,
—N(CH$_3$)Bn,
—N(H)CH$_2$CH$_2$Ph,
—N(CH$_3$)CH$_2$CH$_2$Ph,
—N(CH$_3$)CH$_2$CH$_2$OH,
—N(Bn)CH$_2$CH$_2$OH,
—N(CH$_2$CH$_2$Ph)CH$_2$CH$_2$OH,
—N(H)CH$_2$CH$_2$OCH$_2$CH$_2$OH,
—N(Bn)CH$_2$CH$_2$OCH$_2$CH$_2$OH,
—N(CH$_2$CH$_2$Ph)CH$_2$CH$_2$OCH$_2$CH$_2$OH,
tetrahydroisoquinoline, or
isoindoline;
aa2 is Ala or β-PhPro;
aa3 is Leu or tLeu; and
X3 is: —N(H)CH(CH$_2$OH)$_2$,
—N(CH$_3$)CH$_2$CH$_2$OH,
—N(H)CH$_2$CH$_2$OH,
—[Sψ(oxaz)L]—N(CH$_3$)$_2$,
—[Sψ(imid)L]—N(CH$_3$)$_2$,
—N(H)CH$_2$tBu,
-D-Leu-ol, or
-D-Pro-ol.

15. The compound of claim 1, wherein said compound is selected from, Ac-Cha-Gpg-Tic-Nle-βPhPro-[SΨ(oxaz)L]-NMe$_2$, Ac-Cha-Gpg-Tic-Nle-NHCH$_2$CH$_2$Ph, Ac-Cha-Gpg-Tic-Nle-N(Me)Bn, and Ac-Cha-Gpg-Tic-Nle-N(Bn)CH$_2$CH$_2$OCH$_2$CH$_2$OH.

16. The compound of claim 1, wherein said compound binds to MHC class II protein.

17. The compound of claim 16, wherein said MHC class II protein is a DR molecule.

18. The compound of claim 16, wherein said MHC class II protein is selected from 0401, 0101 and 0404.

19. The compound of claim 16, wherein said compound binds to said MHC class II protein with an IC$_{50}$ of less than 4 μM, 2 μM, 1 μM, 500 nM, or 200 nM.

20. The compound of claim 1, wherein said compound shows stability in mouse serum after 24 hours of greater than at least 50%, 60%, 70%, 80%, or 90%.

21. The compound of claim 1, wherein said compound shows stability in rat serum after 24 hours of greater than at least 10%, 20%, 40%, 50%, 60%, 70%, 80%, or 90%.

22. A pharmaceutical composition comprising a compound of claim 1 and a pharmaceutically acceptable excipient.

23. A compound of claim 1, having the structure Ac-Cha-Gpg-Tic-Nle-NHCH$_2$CH$_2$Ph.

24. A compound of claim 1, having the structure Ac-Cha-Gpg-Tic-Nle-μPhPro-[Sψ(oxaz)L]-NMe$_2$.

* * * * *